United States Patent [19]

Baum

[11] Patent Number: 5,776,449

[45] Date of Patent: Jul. 7, 1998

[54] **RECOMBINANT *BACILLUS THURINGIENSIS* STRAINS, INSECTICIDAL COMPOSITIONS AND METHOD OF USE**

[75] Inventor: James A. Baum, Doylestown, Pa.

[73] Assignee: Ecogen Inc., Langhorne, Pa.

[21] Appl. No.: 717,312

[22] Filed: Sep. 20, 1996

Related U.S. Application Data

[63] Continuation-in-part of Ser. No. 266,408, Jun. 24, 1994, which is a continuation-in-part of Ser. No. 89,986, Jul. 8, 1993, Pat. No. 5,441,884.

[51] Int. Cl.$^6$ .............................. A01N 63/00; C12N 1/21
[52] U.S. Cl. .................................. 424/93.2; 424/93.461; 424/405; 435/170; 435/252.31; 435/832
[58] Field of Search ........................... 424/93.2, 93.461, 424/405; 435/252.31, 170, 832

[56] References Cited

U.S. PATENT DOCUMENTS

| | | | |
|---|---|---|---|
| 4,959,317 | 9/1990 | Sauer | 435/172.3 |
| 5,024,837 | 6/1991 | Donovan et al. | 424/93.2 |
| 5,080,897 | 1/1992 | Gonzalez et al. | 424/93.2 |
| 5,102,797 | 4/1992 | Tucker et al. | 435/172.3 |
| 5,187,091 | 2/1993 | Donovan et al. | 435/418 |
| 5,188,960 | 2/1993 | Payne et al. | 435/252.3 |
| 5,196,342 | 5/1993 | Donovan | 435/320.1 |
| 5,229,112 | 7/1993 | Obukowitz et al. | 424/93.2 |
| 5,650,308 | 7/1997 | Baum | 435/172.3 |

FOREIGN PATENT DOCUMENTS

| | | |
|---|---|---|
| 0 342 633 | 5/1989 | European Pat. Off. |
| 0 537 105 | 4/1993 | European Pat. Off. |
| WO91/18102 | 11/1991 | WIPO |
| WO 93/01283 | 1/1993 | WIPO |
| WO 93/02199 | 2/1993 | WIPO |

OTHER PUBLICATIONS

Hofte et al., Microbiol. Rev. 53 (2):242–255 (1989).
Baubonis et al., "Genomic Targeting With Purified Cre Recombinase," *Nucleic Acids Research*, 21:2025–2029 (1993).
Lereclus et al., "Expansion of Insecticidal Host Range of *Bacillus thuringiensis* By in vivo Genetic Recombination," *Bio/Technology*, 10:418–421 (1992).
Dale et al., "Gene Transfer with Subsequent Removal of the Selection Gene from the Host Genome," *Proc. Natl. Acad. USA*, 88:10558–10562 (1991).
Petit et al., "Tn10–Derived Transposons Active in *Bacillus subtilis*," *Journal of Bacteriology*, 172:6736–6740 (1990).
Mettus et al., "Expression of *Bacillus thuringiensis* δ-Endotoxin Genes During Vegetative Growth," *Applied and Environmental Microbiology*, 56:1128–1134 (1990).
Murphy, "Transposable Elements in Gram–Positive Bacteria," *Mobile DNA*, Am. Soc. Microb., Berg & Howe (eds.), Washington, DC, pp. 269–288 (1989).
Youngman et al., "Methods for Genetic Manipulation, Cloning, and Functional Analysis of Sporulation Genes in *Bacillus subtilis*," *Regulation of Procaryotic Development*, Smith (ed.), ASM, Washington, pp. 65–87 (1989).

Höfte et al., "Insecticidal Crystal Proteins of *Bacillus thuringiensis*," *Microbiological Reviews*, 53:242–255 (1989).
Craig, "The Mechanism of Conservative Site-Specific Recombination," *Annu. Rev. Genet.*, 22:77–105 (1988).
Mahillon et al., "Complete Nucleotide Sequence of pG12, a *Bacillus thuringiensis* Plasmid Containing Tn4430," *Nucleic Acids Research*, 16:11827–11828 (1988).
Mahillon et al. "Cloning and Partial Characterization of Three Small Cryptic Plasmids from *Bacillus thuringiensis*," *Plasmid*, 19:169–173 (1988).
Lereclus et al., "Characterization of two *Bacillus thuringiensis* Plasmids Whose Replication is Thermosensitive in *B. subtilis*," *FEMS Microbiology Letters*, 49:417–422 (1988).
Mahillon et al., "Structural and Functional Analysis of Tn4430: Identification of an Integrase–like Protein Involved in the Co–Integrate–Resolution Process," *The Embo Journal*, 7:1515–1526 (1988).
Youngman, "Plasmid Vectors for Recovering and Exploiting Tn917 Transpositions in Bacillus and Other Gram–Positive Bacteria," *Plasmid—A Practical Approach*, Hardy (ed.) IRL Press, Oxford, England, pp. 79–103 (1987).
Villafane et al., "Replication Control Genes of Plasmid pE194," *Journal of Bacteriology*, 169:4822–4829 (1987).
Lereclus et al., "Identification of Tn4430, a Transposon of *Bacillus thuringiensis* Functional in *Escherichia coli*," *Mol. Gen. Genet.*, 204:52–57 (1986).
Heffron, "Tn3 and Its Relatives," *Mobile Genetic Elements*, Shapiro (ed.), Academic Press, Orlando, FL, pp. 223–260 (1983).
Baum, "Tn5401, a New Class II Transposable Element from *Bacillus thuringiensis*," *J. Bacteriol.*, 176:2835–2845 (May 1994).
Malvar et al., "Tn5401 Disruption of the SpoOF Gene, Identified by Direct Chromosomal Sequencing. Results in CryIIIA Overproduction in *Bacillus thuringiensis*," *J. Bacteriol.*, 176:4750–4753 (Aug. 1994).
"Certain Companies: Applications to Register Pesticide Products," *Federal Register*, 59(163):43577 (Aug. 24, 1994).
Lewin, "Genes," John Wiley & Sons, Inc., NY, pp. 600–604 (1983).
Chiang et al., "Recombination Between Two TnA Transposon Sequences Oriented as Inverse Repeats is Found Less Frequently than Between Direct Repeats," *Mol. Gen. Genet.*, 185:169–175 (1982).
Specimen Label for "CRYMAX™ Bioinsecticide," EPA Reg.No. 55638-34 (one page).
Specimen Label for "LEPINOX™ wdg bioinsecticide," EPA Reg. No. 55638-37 (one page).

*Primary Examiner*—Johnny F. Railey, II
*Attorney, Agent, or Firm*—Panitch Schwarze Jacobs & Nadel, P.C.

[57] ABSTRACT

A transposable element, or transposon, isolated from *Bacillus thuringiensis* (*B.t.*) and designated as transposon Tn5401. The invention also includes a method of using this transposon in a site-specific recombination system for construction of recombinant *B.t.* strains that contain insecticidal *B.t.* toxin protein genes and that are free of DNA not native to *B.t.*, insecticidal compositions containing recombinant *B.t.* strains and their use in insect control methods.

21 Claims, 33 Drawing Sheets

FIGURE 1A

```
GGGGTATGTG TAGCAATGGA ACAGAATCAC GCAACAAGCA TTAGCGGACA TTATTCGCAC     60
                                                      Nsi I
ACAAAAAAGG AAGGTTCTTC GATTCAGAAG ACCTTTCTTT TAAAAATGCA TGTTTGCCTT    120
                                                           Nsp I
ATTTATAGAT GTCACCACGA TTTCCAATTG CTTGTATGTA TATGACTTTC TCATCATGAT    180
                                Cla I
TTATTTCAAA TAAAATTCGA AAGGTTCCAA TCCGTAATCG ATATAGTTCT GTGTAACCTT    240
TCATACTTTT AATATCTCCT TCAGGAGGAA TCTTAAGAAG TCCCTTCAAT CCTTCTGCAA    300
TTCTTTTTTG AATCCCTTTT TCTTGCTTTG CAATAAATTT CACCGCGGAC TTATGGTAAA    360
TCAATTTGTA GTCCGAATTC ACGTTTTGCG TCCTCCCCTG ATACATATCC TTCTTCACTG    420
TTTAACTGTT CTAACTCTTG TGTAGACAGC GGTTCATGAT CAGGATCTGC CATATCAATT    480
TTTTCCCATT CTTTAGGTTT TCTTCTTGAC CGTTGAACAA GAAATTCTAA AAAGTCAAAT    540
GCTGCTTTTT CATCTTGTTG ATCCAGGTGA TCAATTAACC GATACAATTC ATCTTTACGA    600
ATAGCCATGT GTTACACCTA CTTTCGAGAT AGTTTTAAAT GTCCACTAAT TAATATTAGT    660
GGACATGAAG TGTGGGAAAA TAAATGTTTG ATGTCCGCTA ACATAATTGA TAAGATTAAA    720
ATATCATGTC CGCTAATGTA AGTCAATAAA AGAGGAGGTA TTT ATG CAT TCC ACT      775
                                         Nsi I       Met His Ser Thr
                                                      1

AAA ACA ATT TCT ATA CAA GCA ACA TCT TTG ATT TCC GAT TTT ATT TCT     823
Lys Thr Ile Ser Ile Gln Ala Thr Ser Leu Ile Ser Asp Phe Ile Ser
 5                   10                  15                  20
```

FIGURE 1B

```
AGC TTA TCT CAA GAA GGA GAT TTG CAT ACA AAA ACA CTA AAA GAA TAT     871
Ser Leu Ser Gln Glu Gly Asp Leu His Thr Lys Thr Leu Lys Glu Tyr
         25                      30                      35

ACG AGT GAT TTA AAA GAT TTT GTA TTT TGG TTT GAA AAT GTG TGG GGA     919
Thr Ser Asp Leu Lys Asp Phe Val Phe Trp Phe Glu Asn Val Trp Gly
         40                      45                      50
    NspI
AAA CAT GCT GAG GAT ACT CTT TTT CAT CCA ATA GAA GTT ACC GCT CGC     967
Lys His Ala Glu Asp Thr Leu Phe His Pro Ile Glu Val Thr Ala Arg
         55                      60                      65

ACT ATT GCT CGA TAT CGA GGG CAT ATG CAA GTT ACA AGA TTA CTA AAA    1015
Thr Ile Ala Arg Tyr Arg Gly His Met Gln Val Thr Arg Leu Leu Lys
         70                      75                      80

CCT TCT ACG ATT AAC CGG CGC ATT AAT TCA ATC AAA CGT TAT TTT GAC    1063
Pro Ser Thr Ile Asn Arg Arg Ile Asn Ser Ile Lys Arg Tyr Phe Asp
         85                      90                      95                 100

TGG GCT AAG CAA AAA GGA CTG GTA CAA ACA AAT TAT TCA AAA TCA ATT    1111
Trp Ala Lys Gln Lys Gly Leu Val Gln Thr Asn Tyr Ser Lys Ser Ile
                105                     110                     115

AAG TTT GTA CCA ACA GAA AAA ACG AGT CCC AAA CGC ATG TCA GAT AAA    1159
Lys Phe Val Pro Thr Glu Lys Thr Ser Pro Lys Arg Met Ser Asp Lys
         120                     125                     130

GAA GCC GCT TTA ATG CAT GCC GTT GAA AAA TAC GGC TAC ACA CTA CGT    1207
Glu Ala Ala Leu Met His Ala Val Glu Lys Tyr Gly Tyr Thr Leu Arg
         135                     140                     145
```

FIGURE 1C

```
GAC AGG GCA ATG ATT TTT ATG CTT CAT ACT GGC CTT CGT TCA ATG          1255
Asp Arg Ala Met Ile Phe Met Leu His Thr Gly Leu Arg Ser Met
150                 155                 160

GAA GTG TGT GAT GTT CAA ATA GAG GAT GTT ATC ATG AGA AAA AGA GGC      1303
Glu Val Cys Asp Val Gln Ile Glu Asp Val Ile Met Arg Lys Arg Gly
165                 170                 175                 180

GGC TAT GTT GTT GTT CGA TCT GGA AAA AAT AAA CGA AGG GAA GAA GTG      1351
Gly Tyr Val Val Val Arg Ser Gly Lys Asn Lys Arg Gln Arg Glu Val
185                 190                 195

CCT TTG AAT AGT ACA GCT CGT TGT GCA CTA GAA GAA CAT ATC AGA TTA      1399
Pro Leu Asn Ser Thr Ala Arg Cys Ala Leu Glu Glu His Ile Arg Leu
200                 205                 210

AGT GAG ATT TCA CAG AGT TAT TTG TTT CCT TCT TCT AAA ACA GGA AAA      1447
Ser Glu Ile Ser Gln Ser Tyr Leu Phe Pro Ser Ser Lys Thr Gly Lys
215                 220                 225

CGC CTA CAA GAA AGA GCG ATC ATT CTT CAG AAG TAT ATT AGA              1495
Arg Leu Gln Glu Arg Ala Ile Ile Leu Gln Lys Tyr Ile Arg
230                 235                 240

CTT GCA AAG TTA GAA GGA TTT AGT GCC CAT GAT TTA AGG CAT CGC TTT      1543
Leu Ala Lys Leu Glu Gly Phe Ser Ala His Asp Leu Arg His Arg Phe
245                 250                 255                 260

GGT TAT GTG ATG GCT GAA CGC ACA CCA TTA CAT CGT CTT GCA CAA ATT      1591
Gly Tyr Val Met Ala Glu Arg Thr Pro Leu His Arg Leu Ala Gln Ile
265                 270                 275
```

FIGURE 1D

```
ATG GGA CAC GAT AAC TTG AAT ACC ACG ATG ATT TAT GTA AGA GCT ACA         1639
Met Gly His Asp Asn Leu Asn Thr Thr Met Ile Tyr Val Arg Ala Thr
            280                     285                     290

CAA GAA GAT TTA CAG GGA GAA GTA GAA AAG ATT GCC TGG AAC TAAAGAATGC      1691
Gln Glu Asp Leu Gln Gly Glu Val Glu Lys Ile Ala Trp Asn
        295                     300                 305

ACATTATCCT ACTCATTTGG TCATGTGATA CAAAATAAGA ATTGTAACAG GAGGAACAAG       1751

GGTT ATG CCT GTA GAT TTT TTA ACA CCT GAA CAA GAA GAA AAA TAT GGT        1800
     Met Pro Val Asp Phe Leu Thr Pro Glu Gln Glu Glu Lys Tyr Gly
      1                   5                      10              15

TGT TTT TGT GAC ACT CCA ACA TCA GAG CAG TTA GCA AAA TAT TTT TGG         1848
Cys Phe Cys Asp Thr Pro Thr Ser Glu Gln Leu Ala Lys Tyr Phe Trp
                    20                      25                  30

TTA GAT GAT ACA GAC AAA GAA CTG ATA TGG AAT CGT CGT GGA GAG CAT         1896
Leu Asp Asp Thr Asp Lys Glu Leu Ile Trp Asn Arg Arg Gly Glu His
                35                      40                      45

AAT CAA CTT GGT TTC GCT GTT CAA TTA GGA ACC GTT AGG TTC TTA GGA         1944
Asn Gln Leu Gly Phe Ala Val Gln Leu Gly Thr Val Arg Phe Leu Gly
            50                      55                  60

ACA TTT TTA TCT GAT CCT ACA AAT GTA CCA CAA TCG GTT ATT ACA TAT         1992
Thr Phe Leu Ser Asp Pro Thr Asn Val Pro Gln Ser Val Ile Thr Tyr
        65                      70                  75

ATG GCA AAT CAA CTT CAT CTA GAT GCT CAA AGC TTT TCT CGT TAT CGA         2040
Met Ala Asn Gln Leu His Leu Asp Ala Gln Ser Phe Ser Arg Tyr Arg
    80                      85                  90                  95
```

FIGURE 1E

```
AAT AAA CGA AGT CAG TGG GAT CAA ATG CAA GAG ATA CGT TCT GTT TAT     2088
Asn Lys Arg Ser Gln Trp Asp Gln Met Gln Glu Ile Arg Ser Val Tyr
            100                         105                 110

GGA TAT AAA AAC ACA GAT AAA TCA ACA CAT TGG CGA TTC ATC AGA         2136
Gly Tyr Lys Asn Thr Asp Lys Ser Thr His Trp Arg Phe Ile Arg
            115                         120                 125

TGG CTA TAT GCA CGT GCT TGG CTA TAT AAT GAA CGG CCA AGT GTC TTA     2184
Trp Leu Tyr Ala Arg Ala Trp Leu Tyr Asn Glu Arg Pro Ser Val Leu
            130                         135                 140

TTT GAT TTA GCA ACA GCA CGA TGT ATC GAA CAA AAA ATT TTA CTA CCT     2232
Phe Asp Leu Ala Thr Ala Arg Cys Ile Glu Gln Lys Ile Leu Leu Pro
            145                         150                 155

GGT GTA TCT GTA TTA ACA AGG CTA GTA TCA ACG GTT CGT GAT CGT TCA     2280
Gly Val Ser Val Leu Thr Arg Leu Val Ser Thr Val Arg Asp Arg Ser
            160                         165                 170                 175

GCA GAA AAT ATA TGG TCT CTT AGT CTC CTT CCG GAT AAT GTT CAG         2328
Ala Glu Asn Ile Trp Lys Leu Ser Ser Leu Pro Asp Asn Val Gln
            180                         185                 190

AAA AAA CAA TTA GAA AAC CTT CTT CAG ATA GAT CAA AAA ACA AAG AAA     2376
Lys Lys Gln Leu Glu Asn Leu Leu Gln Ile Asp Gln Lys Thr Lys Lys
            195                         200                 205

ACG TAT TTA GAG CGT CTA AGT AAT CCC CCT GTT CCG ATT AGT GTT ACG     2424
Thr Tyr Leu Glu Arg Leu Ser Asn Pro Pro Val Pro Ile Ser Val Thr
            210                         215                 220
```

FIGURE 1F

```
GGC ATT AAG AAT ACG CTG ATT CGT TTA CAA GAG CTT CGT CAA TTG AAC    2472
Gly Ile Lys Asn Thr Leu Ile Arg Leu Gln Glu Leu Arg Gln Leu Asn
225                 230                 235

ACT GAA AAT TGG GAT ATG TCT AGA ATT CCT TCG AAA AGA TTA CAA CAA    2520
Thr Glu Asn Trp Asp Met Ser Arg Ile Pro Ser Lys Arg Leu Gln Gln
240                 245                 250                 255

TTC GCG CGT CAC ACA GTC GCT GTT AGA TCA CAA ATT GCT AGA ATG        2568
Phe Ala Arg His Thr Val Ala Val Arg Ser Gln Ile Ala Arg Met
        260                 265                 270

CCC GAT CAA CGA CGT ATG GCT ATG TTA GTT GCA TTT GCT AAA ATG TAT    2616
Pro Asp Gln Arg Arg Met Ala Met Leu Val Ala Phe Ala Lys Met Tyr
        275                 280                 285

ACA CAA AGT GCT CAG GAT GAT GTC ATT GAT ATT TTT GAT AGA TAT TTA    2664
Thr Gln Ser Ala Gln Asp Asp Val Ile Asp Ile Phe Asp Arg Tyr Leu
        290                 295                 300

ACA GAT TTA TTT GCT AAG ACA TAT CGA AAG GAA CAA CAA AAA GAA CGT CTT 2712
Thr Asp Leu Phe Ala Lys Thr Tyr Arg Lys Glu Gln Lys Glu Arg Leu
        305                 310                 315
                                                    Bss HII
CGT ACA ATT AAG GAT TTA GAT AAG GCA GCG CGC CAA TTA CGG GAA GCT    2760
Arg Thr Ile Lys Asp Leu Asp Lys Ala Ala Arg Gln Leu Arg Glu Ala
320                 325                 330                 335

TGT GTA ATA TTA TTA GAA CAT ACG GAT CCT TCT GTC CAT CCA AAA ACG    2808
Cys Val Ile Leu Leu Glu His Thr Asp Pro Ser Val His Pro Lys Thr
        340                 345                 350
```

FIGURE 1G

```
GCA GTG TTT GAA AAA ATT TCA GAA AAG GAT TTA ATA CAA GCT GTC CAA    2856
Ala Val Phe Glu Lys Ile Ser Glu Lys Asp Leu Ile Gln Ala Val Gln
            355                 360                 365

ATT GTT GAT TCA CTC ACC TAT TCA CCA AAT CAA ACA CTA GCC TAT TCA    2904
Ile Val Asp Ser Leu Thr Tyr Ser Pro Asn Gln Thr Leu Ala Tyr Ser
            370                 375                 380

GGA TTG TTA CAA CAT TAT GGC ATA ATC CGA AAA TTT CCT TTA CTC        2952
Gly Leu Leu Gln His Tyr Gly Ile Ile Arg Lys Phe Pro Leu Leu
            385                 390                 395

ATG GAA GAA ATT GAA TTA CAA GCA ACG CCT GCT GGA TTA CCC ATC TTG    3000
Met Glu Glu Ile Glu Leu Gln Ala Thr Pro Ala Gly Leu Pro Ile Leu
            400                 405                 410             415

CAA GCA TGG AAT TTT GTA AAA GAG CAT GGG AAA TCC AAT GCA AAT AGA    3048
Gln Ala Trp Asn Phe Val Lys Glu His Gly Lys Ser Asn Ala Asn Arg
            420                 425                 430

TGG AAA AAT GCT CCT CTT GCC GGT TTG AAT GTA AAT CAT CGA GCA TAT ACG TTT    3096
Trp Lys Asn Ala Pro Leu Ala Gly Leu Asn Val Asn His Arg Ala Tyr Thr Phe
            435                 440                 445

GTA ATT GAT AAA GAT TCC GGA ACT GTA AAT CAT CGA GCA TAT ACG TTT    3144
Val Ile Asp Lys Asp Ser Gly Thr Val Asn His Arg Ala Tyr Thr Phe
            450                 455                 460

TGG ATG CTC GAA CAA GTA TTA GAA GCT TTG CAC CGA CAT GAT CTA TAT    3192
Trp Met Leu Glu Gln Val Leu Glu Ala Leu His Arg His Asp Leu Tyr
            465                 470                 475
```

FIGURE 1H

```
ATA GTA GGA AGT GAA AAA TAT GGG GAC CTT CGC GCA CAA TTA CAA           3240
Ile Val Gly Ser Glu Lys Tyr Gly Asp Leu Arg Ala Gln Leu Gln
480             485             490             495

GAC GAA GAA TGG AAA ACT TGG AGT ATT CTT CGC TCA TTA GAC              3288
Asp Glu Glu Trp Lys Thr Trp Ser Ile Leu Arg Ser Leu Asp
             500             505             510

TGG TCA ATA GAT TCT TAT GAA TCA TTG ACA CCG TTA AAA GAG TTA          3336
Trp Ser Ile Asp Ser Tyr Glu Ser Leu Thr Pro Leu Lys Glu Leu
515             520             525

GAC AAA ACT TAT CAT CAA GTC ATT GAG AAT TGG GAG AAT CCT GCG          3384
Asp Lys Thr Tyr His Gln Val Ile Glu Asn Trp Glu Asn Pro Ala
530             535             540

GTG CAA ATA GAC ACA TTT GCA GGT AAA GAG AGA ATT GTT TTG ACA CCT      3432
Val Gln Ile Asp Thr Phe Ala Gly Lys Glu Arg Ile Val Leu Thr Pro
545             550             555

TTA GAC AAA CAA CCA GAA CCT GAA TCA CTA CAA CTA AAA CAA CAA          3480
Leu Asp Lys Gln Pro Glu Pro Glu Ser Leu Gln Leu Lys Gln Gln
560             565             570             575

ATA CAT ACG ATG TTG CCA AAT ATA GAT ATT CCT CAA TTA TTA CTC GAA      3528
Ile His Thr Met Leu Pro Asn Ile Asp Ile Pro Gln Leu Leu Leu Glu
580             585             590

GTA AAT CGT TGG ACG GGA TTT ATG GAT GGT TTT CGA CAT ATT AGT GAG     3576
Val Asn Arg Trp Thr Gly Phe Met Asp Gly Phe Arg His Ile Ser Glu
595             600             605
```

FIGURE 11

```
GCT AAA TCT AGA ATT AAC GAG TTA CCT ATA AGT ATC TGT GCA TTG CTT   3624
Ala Lys Ser Arg Ile Asn Glu Leu Pro Ile Ser Ile Cys Ala Leu Leu
610             615                 620

ATA TCT CAA GCA TGC AAT ATT GGG TTA AGA CCT TTA CAA GAT GGG       3672
Ile Ser Gln Ala Cys Asn Ile Gly Leu Arg Pro Leu Val Gln Asp Gly
    625                 630                 635

GTT CCT TCA TTA GAA CGT GAT CGT CTT ACA TGG ATT GAA CAA AAT TAT   3720
Val Pro Ser Leu Glu Arg Asp Arg Leu Thr Trp Ile Glu Gln Asn Tyr
640             645                 650                 655

TTT CGT GCA GAA ACA CTT TCA GAA TCA AAC GCG AAA CTT GTA GAT TTT   3768
Phe Arg Ala Glu Thr Leu Ser Glu Ser Asn Ala Lys Leu Val Asp Phe
        660                 665                 670

CAT AGC CAA TTA CAG CTG GCT AAA ATG TGG GGT GGA GAA ATT GCT       3816
His Ser Gln Leu Gln Leu Ala Lys Met Trp Gly Gly Glu Ile Ala
    675                 680                 685

TCA GCT GAT GGA TTA CGT TTC ATC ACA CCA GTA AAA TCC GTA CAC ACT   3864
Ser Ala Asp Gly Leu Arg Phe Ile Thr Pro Val Lys Ser Val His Thr
690             695                 700

GGT CCA AAT CCT AAA TAT TTC GGT TCT GGT CGT GGT GTT ACG TAT TAC   3912
Gly Pro Asn Pro Lys Tyr Phe Gly Ser Gly Arg Gly Val Thr Tyr Tyr
705             710                 715

AAC TAT ACG AGC GAT CAA TTT ACC GGA CTC CAC GGT TTG GTG ATT CCA   3960
Asn Tyr Thr Ser Asp Gln Phe Thr Gly Leu His Gly Leu Val Ile Pro
720             725                 730                 735
```

FIGURE 1J

```
GGC ACA ATT CGT GAT TCA TTA TAC CTT CAA TGT GTG TTA GAA CAA         4008
Gly Thr Ile Arg Asp Ser Leu Tyr Leu Gln Cys Val Leu Glu Gln
                740                 745                 750

AAT ACG AAC TTA CAG CCA AAA GAA ATT ATG ACA GAT ACA GCT GGG TAT     4056
Asn Thr Asn Leu Gln Pro Lys Glu Ile Met Thr Asp Thr Ala Gly Tyr
            755                 760                 765

AGT GAT ATT TTT GGG CTC TTT GGA TTA TTA GGA TAT CAA TTT AGT         4104
Ser Asp Ile Phe Gly Leu Phe Gly Leu Leu Gly Tyr Gln Phe Ser
        770                 775                 780

CCT CGT TTA GCT GAT ATC AGT GAA TCA CGT CTT TGG CGT TTT GAT GCG     4152
Pro Arg Leu Ala Asp Ile Ser Glu Ser Arg Leu Trp Arg Phe Asp Ala
    785                 790                 795

AAC TCA GAT TAT AGC ATG AAT TTG TCT AAT AAT TTG TCT AAA AGT CGC ATT CGT  4200
Asn Ser Asp Tyr Ser Met Ser Met Leu Asn Asn Leu Ser Lys Ser Arg Ile Arg
800                 805                 810                 815

GAA CTC ATA CAT CGT CAT TGG GAA GAC ATG CTT CGT GTT GCC GGA         4248
Glu Leu Ile His Arg His Trp Glu Asp Met Leu Arg Val Ala Gly
        820                 825                 830

TCT TTG AAA CTA AAT GCA AAT ATA AAT GCA ACA CAT CTT ATC CAA GCA CTT 4296
Ser Leu Lys Leu Asn Ala Asn Ile Asn Ala Thr His Leu Ile Gln Ala Leu
    835                 840                 845

CAG TAT AAT GGG AAA CCA ACT ATG ACC CCA TTA GGG CGA GCA ATT GGA GAA TTG  4344
Gln Tyr Asn Gly Lys Pro Thr Met Thr Pro Leu Gly Arg Ala Ile Gly Glu Leu
850                 855                 860
```

FIGURE 1K

```
GGG AGA CTC TTT AAA ACA CGT TAT TTA CTC TTA TAT TTA CAT GAT GAA    4392
Gly Arg Leu Phe Lys Thr Arg Tyr Leu Leu Leu Tyr Leu His Asp Glu
865                 870                 875

AAT TAT CGT CGT AAA ATT TTA AAT CAA CTC AAT AGA GGG GAA GCA AGG    4440
Asn Tyr Arg Arg Lys Ile Leu Asn Gln Leu Asn Arg Gly Glu Ala Arg
880                 885                 890                 895

CAT AGT TTA GCG AGG GCT GTA TTT TAC GGC AAA CGT GGA GAA CTT CAT    4488
His Ser Leu Ala Arg Ala Val Phe Tyr Gly Lys Arg Gly Glu Leu His
        900                 905                 910

CAA TCC TAT CGA GAA GGA CAA GAG GAA CGT TTA GGT GCA TTA GGT TTA    4536
Gln Ser Tyr Arg Glu Gly Gln Glu Glu Arg Leu Gly Ala Leu Gly Leu
915                 920                 925

GTA GTA AAT GCA ATT ATT GTA TGG AAT ACA CGA TAT ATA GAA TCT GCG    4584
Val Val Asn Ala Ile Ile Val Trp Asn Thr Arg Tyr Ile Glu Ser Ala
        930                 935                 940

TTA CAA GTA CTC CGA AAT CGC GGT CAT ACA ATT GAT AAT GAT GAT ATA    4632
Leu Gln Val Leu Arg Asn Arg Gly His Thr Ile Asp Asn Asp Asp Ile
945                 950                 955

TCT AGA CTT TCA CCA TTA GGC CAT AAA CAC ATT AAC ATA GTA GGT CGG    4680
Ser Arg Leu Ser Pro Leu Gly His Lys His Ile Asn Ile Val Gly Arg
        960                 965                 970                 975

TAT TCA TTT GTT CTC CCA GAA GTA AAA GAT GGG CAA TTA CGT ACA        4728
Tyr Ser Phe Val Leu Pro Glu Val Lys Asp Gly Gln Leu Arg Thr
980                 985                 990
```

FIGURE 1L

```
CTA ACA TAT GAA GAA ACA AAC AAA AAG GAA CCT GAT TCT TTA TAAGAATAGG    4780
Leu Thr Tyr Glu Glu Thr Asn Lys Lys Glu Pro Asp Ser Leu
        995                 1000                 1005

TTCCTAATGT CCGCTAATGC TTGTTGCGTG ATTTTGTTCC ATTGCTACAC ATACCCC        4837
```

Tn5401

4837 bp pEG911-1 pEG911-3

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 4837 base pairs
        ( B ) TYPE: nucleic acid
        ( C ) STRANDEDNESS: double
        ( D ) TOPOLOGY: circular ( i i ) MOLECULE TYPE: DNA (genomic)

( i x ) FEATURE:
        ( A ) NAME/KEY: transposon
        ( B ) LOCATION: 1..4837

( i x ) FEATURE:
        ( A ) NAME/KEY: CDS
        ( B ) LOCATION: 764..1684

( i x ) FEATURE:
        ( A ) NAME/KEY: CDS
        ( B ) LOCATION: 1756..4773

( i x ) FEATURE:
        ( A ) NAME/KEY: CDS
        ( B ) LOCATION: complement (351..608)

( x i ) SEQUENCE DESCRIPTION: SEQ ID NO:1:

```
GGGGTATGTG  TAGCAATGGA  ACAGAATCAC  GCAACAAGCA  TTAGCGGACA  TTATTCGCAC      60

ACAAAAAGG   AAGGTTCTTC  GATTCAGAAG  ACCTTTCTTT  TAAAAATGCA  TGTTTGCCTT     120
```

-continued

```
ATTTATAGAT GTCACCACGA TTTCCAATTG CTTGTATGTA TATGACTTTC TCATCATGAT        180

TTATTTCAAA TAAAATTCGA AAGGTTCCAA TCCGTAATCG ATATAGTTCT GTGTAACCTT        240

TCATACTTTT AATATCTCCT TCAGGAGGAA TCTTAAGAAG TCCCTTCAAT CCTTCTGCAA        300

TTCTTTTTTG AATCCCTTTT TCTTGCTTTG CAATAAATTT CACCGCGGAC TTATGGTAAA        360

TCAATTTGTA GTCCGAATTC ACGTTTGCG TCCTCCCCTG ATACATATCC TTCTTCACTG         420

TTTAACTGTT CTAACTCTTG TGTAGACAGC GGTTCATGAT CAGGATCTGC CATATCAATT        480

TTTTCCCATT CTTTAGGTTT TCTTCTTGAC CGTTGAACAA GAAATTCTAA AAAGTCAAAT        540

GCTGCTTTTT CATCTTGTTG ATCCAGGTGA TCAATTAACC GATACAATTC ATCTTTACGA        600

ATAGCCATGT GTTACACCTA CTTTCGAGAT AGTTTTAAAT GTCCACTAAT TAATATTAGT        660

GGACATGAAG TGTGGGAAAA TAAATGTTTG ATGTCCGCTA ACATAATTGA TAAGATTAAA        720

ATATCATGTC CGCTAATGTA AGTCAATAAA AGAGGAGGTA TTT ATG CAT TCC ACT         775
                                                Met His Ser Thr
                                                1
```

| | | | | | | | | | | | | | | | | |
|---|---|---|---|---|---|---|---|---|---|---|---|---|---|---|---|---|
| AAA | ACA | ATT | TCT | ATA | CAA | GCA | ACA | TCT | TTG | ATT | TCC | GAT | TTT | ATT | TCT | 823 |
| Lys | Thr | Ile | Ser | Ile | Gln | Ala | Thr | Ser | Leu | Ile | Ser | Asp | Phe | Ile | Ser | |
| 5 | | | | 10 | | | | | 15 | | | | | | 20 | |
| AGC | TTA | TCT | CAA | GAA | GGA | GAT | TTG | CAT | ACA | AAA | ACA | CTA | AAA | GAA | TAT | 871 |
| Ser | Leu | Ser | Gln | Glu | Gly | Asp | Leu | His | Thr | Lys | Thr | Leu | Lys | Glu | Tyr | |
| | | | | 25 | | | | | 30 | | | | | 35 | | |
| ACG | AGT | GAT | TTA | AAA | GAT | TTT | GTA | TTT | TGG | TTT | GAA | AAT | GTG | TGG | GGA | 919 |
| Thr | Ser | Asp | Leu | Lys | Asp | Phe | Val | Phe | Trp | Phe | Glu | Asn | Val | Trp | Gly | |
| | | | 40 | | | | | 45 | | | | 50 | | | | |
| AAA | CAT | GCT | GAG | GAT | ACT | CTT | TTT | CAT | CCA | ATA | GAA | GTT | ACC | GCT | CGC | 967 |
| Lys | His | Ala | Glu | Asp | Thr | Leu | Phe | His | Pro | Ile | Glu | Val | Thr | Ala | Arg | |
| | | 55 | | | | | 60 | | | | | 65 | | | | |
| ACT | ATT | GCT | CGA | TAT | CGA | GGG | CAT | ATG | CAA | GTT | ACA | AGA | TTA | CTA | AAA | 1015 |
| Thr | Ile | Ala | Arg | Tyr | Arg | Gly | His | Met | Gln | Val | Thr | Arg | Leu | Leu | Lys | |
| | 70 | | | | | 75 | | | | | 80 | | | | | |
| CCT | TCT | ACG | ATT | AAC | CGG | CGC | ATT | AAT | TCA | ATC | AAA | CGT | TAT | TTT | GAC | 1063 |
| Pro | Ser | Thr | Ile | Asn | Arg | Arg | Ile | Asn | Ser | Ile | Lys | Arg | Tyr | Phe | Asp | |
| 85 | | | | 90 | | | | | 95 | | | | | 100 | | |
| TGG | GCT | AAG | CAA | AAA | GGA | CTG | GTA | CAA | ACA | AAT | TAT | TCA | AAA | TCA | ATT | 1111 |
| Trp | Ala | Lys | Gln | Lys | Gly | Leu | Val | Gln | Thr | Asn | Tyr | Ser | Lys | Ser | Ile | |
| | | | | 105 | | | | | 110 | | | | | 115 | | |
| AAG | TTT | GTA | CCA | ACA | GAA | AAA | ACG | AGT | CCC | AAA | CGC | ATG | TCA | GAT | AAA | 1159 |
| Lys | Phe | Val | Pro | Thr | Glu | Lys | Thr | Ser | Pro | Lys | Arg | Met | Ser | Asp | Lys | |
| | | | 120 | | | | | 125 | | | | 130 | | | | |
| GAA | GAA | GCC | GCT | TTA | ATG | CAT | GCC | GTT | GAA | AAA | TAC | GGC | ACA | CTA | CGT | 1207 |
| Glu | Glu | Ala | Ala | Leu | Met | His | Ala | Val | Glu | Lys | Tyr | Gly | Thr | Leu | Arg | |
| | | 135 | | | | | 140 | | | | | 145 | | | | |
| GAC | AGG | GCA | ATG | ATT | ATT | TTT | ATG | CTT | CAT | ACT | GGC | CTT | CGT | TCA | ATG | 1255 |
| Asp | Arg | Ala | Met | Ile | Ile | Phe | Met | Leu | His | Thr | Gly | Leu | Arg | Ser | Met | |
| | | 150 | | | | 155 | | | | | 160 | | | | | |
| GAA | GTG | TGT | GAT | GTT | CAA | ATA | GAG | GAT | GTT | ATC | ATG | AGA | AAA | AGA | GGC | 1303 |
| Glu | Val | Cys | Asp | Val | Gln | Ile | Glu | Asp | Val | Ile | Met | Arg | Lys | Arg | Gly | |
| 165 | | | | | 170 | | | | | 175 | | | | | 180 | |
| GGC | TAT | GTT | GTT | GTT | CGA | TCT | GGA | AAA | CGA | AAT | AAA | CAG | AGG | GAA | GTG | 1351 |
| Gly | Tyr | Val | Val | Val | Arg | Ser | Gly | Lys | Arg | Asn | Lys | Gln | Arg | Glu | Val | |
| | | | | 185 | | | | | 190 | | | | | 195 | | |
| CCT | TTG | AAT | AGT | ACA | GCT | CGT | TGT | GCA | CTA | GAA | GAA | CAT | ATC | AGA | TTA | 1399 |
| Pro | Leu | Asn | Ser | Thr | Ala | Arg | Cys | Ala | Leu | Glu | Glu | His | Ile | Arg | Leu | |
| | | | 200 | | | | 205 | | | | | 210 | | | | |
| AGT | GAG | ATT | TCA | CAG | AGT | TAT | TTG | TTT | CCT | TCT | TCT | AAA | ACA | GGA | AAA | 1447 |
| Ser | Glu | Ile | Ser | Gln | Ser | Tyr | Leu | Phe | Pro | Ser | Ser | Lys | Thr | Gly | Lys | |
| | | 215 | | | | | 220 | | | | | 225 | | | | |

```
CGC CTA CAA GAA AGA GCG ATC CGC CAT ATT CTT CAG AAG TAT ATT AGA      1495
Arg Leu Gln Glu Arg Ala Ile Arg His Ile Leu Gln Lys Tyr Ile Arg
    230                 235                 240

CTT GCA AAG TTA GAA GGA TTT AGT GCC CAT GAT TTA AGG CAT CGC TTT      1543
Leu Ala Lys Leu Glu Gly Phe Ser Ala His Asp Leu Arg His Arg Phe
245             250                 255                 260

GGT TAT GTG ATG GCT GAA CGC ACA CCA TTA CAT CGT CTT GCA CAA ATT      1591
Gly Tyr Val Met Ala Glu Arg Thr Pro Leu His Arg Leu Ala Gln Ile
                265                 270                 275

ATG GGA CAC GAT AAC TTG AAT ACC ACG ATG ATT TAT GTA AGA GCT ACA      1639
Met Gly His Asp Asn Leu Asn Thr Thr Met Ile Tyr Val Arg Ala Thr
            280                 285                 290

CAA GAA GAT TTA CAG GGA GAA GTA GAA AAG ATT GCC TGG AAC TAAAGAATGC   1691
Gln Glu Asp Leu Gln Gly Glu Val Glu Lys Ile Ala Trp Asn
        295                 300                 305

ACATTATCCT ACTCATTTGG TCATGTGATA CAAAATAAGA ATTGTAACAG GAGGAACAAG    1751

GGTT ATG CCT GTA GAT TTT TTA ACA CCT GAA CAA GAA GAA AAA TAT GGT     1800
     Met Pro Val Asp Phe Leu Thr Pro Glu Gln Glu Glu Lys Tyr Gly
     1                5                   10                  15

TGT TTT TGT GAC ACT CCA ACA TCA GAG CAG TTA GCA AAA TAT TTT TGG      1848
Cys Phe Cys Asp Thr Pro Thr Ser Glu Gln Leu Ala Lys Tyr Phe Trp
                20                  25                  30

TTA GAT GAT ACA GAC AAA GAA CTG ATA TGG AAT CGT CGT GGA GAG CAT      1896
Leu Asp Asp Thr Asp Lys Glu Leu Ile Trp Asn Arg Arg Gly Glu His
            35                  40                  45

AAT CAA CTT GGT TTC GCT GTT CAA TTA GGA ACC GTT AGG TTC TTA GGA      1944
Asn Gln Leu Gly Phe Ala Val Gln Leu Gly Thr Val Arg Phe Leu Gly
        50                  55                  60

ACA TTT TTA TCT GAT CCT ACA AAT GTA CCA CAA TCG GTT ATT ACA TAT      1992
Thr Phe Leu Ser Asp Pro Thr Asn Val Pro Gln Ser Val Ile Thr Tyr
    65                  70                  75

ATG GCA AAT CAA CTT CAT CTA GAT GCT CAA AGC TTT TCT CGT TAT CGA      2040
Met Ala Asn Gln Leu His Leu Asp Ala Gln Ser Phe Ser Arg Tyr Arg
80                  85                  90                  95

AAT AAA CGA AGT CAG TGG GAT CAA ATG CAA GAG ATA CGT TCT GTT TAT      2088
Asn Lys Arg Ser Gln Trp Asp Gln Met Gln Glu Ile Arg Ser Val Tyr
                100                 105                 110

GGA TAT AAA AAC TTT ACA GAT AAA TCA ACA CAT TGG CGA TTC ATC AGA      2136
Gly Tyr Lys Asn Phe Thr Asp Lys Ser Thr His Trp Arg Phe Ile Arg
            115                 120                 125

TGG CTA TAT GCA CGT GCT TGG CTA TAT AAT GAA CGG CCA AGT GTC TTA      2184
Trp Leu Tyr Ala Arg Ala Trp Leu Tyr Asn Glu Arg Pro Ser Val Leu
        130                 135                 140

TTT GAT TTA GCA ACA GCA CGA TGT ATC GAA CAA AAA ATT TTA CTA CCT      2232
Phe Asp Leu Ala Thr Ala Arg Cys Ile Glu Gln Lys Ile Leu Leu Pro
    145                 150                 155

GGT GTA TCT GTA TTA ACA AGG CTA GTA TCA ACG GTT CGT GAT CGT TCA      2280
Gly Val Ser Val Leu Thr Arg Leu Val Ser Thr Val Arg Asp Arg Ser
160                 165                 170                 175

GCA GAA AAT ATA TGG AAA AAG CTC TCT AGT CTT CCG GAT AAT GTT CAG      2328
Ala Glu Asn Ile Trp Lys Lys Leu Ser Ser Leu Pro Asp Asn Val Gln
                180                 185                 190

AAA AAA CAA TTA GAA AAC CTT CTT CAG ATA GAT CAA AAA ACA AAG AAA      2376
Lys Lys Gln Leu Glu Asn Leu Leu Gln Ile Asp Gln Lys Thr Lys Lys
            195                 200                 205

ACG TAT TTA GAG CGT CTA AGT AAT CCC CCT GTT CCG ATT AGT GTT ACG      2424
Thr Tyr Leu Glu Arg Leu Ser Asn Pro Pro Val Pro Ile Ser Val Thr
        210                 215                 220

GGC ATT AAG AAT ACG CTG ATT CGT TTA CAA GAG CTT CGT CAA TTG AAC      2472
```

-continued

| | | | | | | | | | | | | | | | | |
|---|---|---|---|---|---|---|---|---|---|---|---|---|---|---|---|---|
| Gly | Ile | Lys | Asn | Thr | Leu | Ile | Arg | Leu | Gln | Glu | Leu | Arg | Gln | Leu | Asn | |
| | 225 | | | | 230 | | | | | 235 | | | | | | |
| ACT | GAA | AAT | TGG | GAT | ATG | TCT | AGA | ATT | CCT | TCG | AAA | AGA | TTA | CAA | CAA | 2520 |
| Thr | Glu | Asn | Trp | Asp | Met | Ser | Arg | Ile | Pro | Ser | Lys | Arg | Leu | Gln | Gln | |
| 240 | | | | | 245 | | | | | 250 | | | | | 255 | |
| TTC | GCG | CGT | CAC | ACA | GTC | GCT | GTT | AGA | TCA | CAA | GCA | ATT | GCT | AGA | ATG | 2568 |
| Phe | Ala | Arg | His | Thr | Val | Ala | Val | Arg | Ser | Gln | Ala | Ile | Ala | Arg | Met | |
| | | | | 260 | | | | | 265 | | | | | 270 | | |
| CCC | GAT | CAA | CGA | CGT | ATG | GCT | ATG | TTA | GTT | GCA | TTT | GCT | AAA | ATG | TAT | 2616 |
| Pro | Asp | Gln | Arg | Arg | Met | Ala | Met | Leu | Val | Ala | Phe | Ala | Lys | Met | Tyr | |
| | | | 275 | | | | | 280 | | | | | 285 | | | |
| ACA | CAA | AGT | GCT | CAG | GAT | GAT | GTC | ATT | GAT | ATT | TTT | GAT | AGA | TAT | TTA | 2664 |
| Thr | Gln | Ser | Ala | Gln | Asp | Asp | Val | Ile | Asp | Ile | Phe | Asp | Arg | Tyr | Leu | |
| | | 290 | | | | | 295 | | | | | 300 | | | | |
| ACA | GAT | TTA | TTT | GCT | AAG | ACA | TAT | CGA | AAG | GAA | CAA | AAA | GAA | CGT | CTT | 2712 |
| Thr | Asp | Leu | Phe | Ala | Lys | Thr | Tyr | Arg | Lys | Glu | Gln | Lys | Glu | Arg | Leu | |
| | 305 | | | | | 310 | | | | | 315 | | | | | |
| CGT | ACA | ATT | AAG | GAT | TTA | GAT | AAG | GCA | GCG | CGC | CAA | TTA | CGG | GAA | GCT | 2760 |
| Arg | Thr | Ile | Lys | Asp | Leu | Asp | Lys | Ala | Ala | Arg | Gln | Leu | Arg | Glu | Ala | |
| 320 | | | | | 325 | | | | | 330 | | | | | 335 | |
| TGT | GTA | ATA | TTA | TTA | GAA | CAT | ACG | GAT | CCT | TCT | GTC | CAT | CCA | AAA | ACG | 2808 |
| Cys | Val | Ile | Leu | Leu | Glu | His | Thr | Asp | Pro | Ser | Val | His | Pro | Lys | Thr | |
| | | | | 340 | | | | | 345 | | | | | 350 | | |
| GCA | GTG | TTT | GAA | AAA | ATT | TCA | GAA | AAG | GAT | TTA | ATA | CAA | GCT | GTC | CAA | 2856 |
| Ala | Val | Phe | Glu | Lys | Ile | Ser | Glu | Lys | Asp | Leu | Ile | Gln | Ala | Val | Gln | |
| | | | 355 | | | | | 360 | | | | | 365 | | | |
| ATT | GTT | GAT | TCA | CTC | ACC | TAT | TCA | CCA | AAT | CAA | ACA | CTA | GCC | TAT | TCA | 2904 |
| Ile | Val | Asp | Ser | Leu | Thr | Tyr | Ser | Pro | Asn | Gln | Thr | Leu | Ala | Tyr | Ser | |
| | | 370 | | | | | 375 | | | | | 380 | | | | |
| GGA | TTG | TTA | CAA | CAT | TAT | GGC | ATA | ATC | CGA | AAA | TTT | CTT | CCT | TTA | CTC | 2952 |
| Gly | Leu | Leu | Gln | His | Tyr | Gly | Ile | Ile | Arg | Lys | Phe | Leu | Pro | Leu | Leu | |
| | 385 | | | | | 390 | | | | | 395 | | | | | |
| ATG | GAA | GAA | ATT | GAA | TTA | CAA | GCA | ACG | CCT | GCT | GGA | TTA | CCC | ATC | TTG | 3000 |
| Met | Glu | Glu | Ile | Glu | Leu | Gln | Ala | Thr | Pro | Ala | Gly | Leu | Pro | Ile | Leu | |
| 400 | | | | | 405 | | | | | 410 | | | | | 415 | |
| CAA | GCA | TGG | AAT | TTT | GTA | AAA | GAG | CAT | GGG | AAA | TCC | AAT | AAG | AAA | AGA | 3048 |
| Gln | Ala | Trp | Asn | Phe | Val | Lys | Glu | His | Gly | Lys | Ser | Asn | Lys | Lys | Arg | |
| | | | | 420 | | | | | 425 | | | | | 430 | | |
| TGG | AAA | AAT | GCT | CCT | CTT | GCC | GGT | TTG | AAT | GCA | AAT | TGG | TCT | AAG | GTT | 3096 |
| Trp | Lys | Asn | Ala | Pro | Leu | Ala | Gly | Leu | Asn | Ala | Asn | Trp | Ser | Lys | Val | |
| | | | 435 | | | | | 440 | | | | | 445 | | | |
| GTA | ATT | GAT | AAA | GAT | TCC | GGA | ACT | GTA | AAT | CAT | CGA | GCA | TAT | ACG | TTT | 3144 |
| Val | Ile | Asp | Lys | Asp | Ser | Gly | Thr | Val | Asn | His | Arg | Ala | Tyr | Thr | Phe | |
| | | 450 | | | | | 455 | | | | | 460 | | | | |
| TGG | ATG | CTC | GAA | CAA | GTA | TTA | GAA | GCT | TTG | CAC | CGA | CAT | GAT | CTA | TAT | 3192 |
| Trp | Met | Leu | Glu | Gln | Val | Leu | Glu | Ala | Leu | His | Arg | His | Asp | Leu | Tyr | |
| | 465 | | | | | 470 | | | | | 475 | | | | | |
| ATA | GTA | GGA | AGT | GAA | AAA | TAT | GGG | GAC | CTT | CGC | GCA | CAA | TTA | TTA | CAA | 3240 |
| Ile | Val | Gly | Ser | Glu | Lys | Tyr | Gly | Asp | Leu | Arg | Ala | Gln | Leu | Leu | Gln | |
| 480 | | | | | 485 | | | | | 490 | | | | | 495 | |
| GAC | GAA | GAA | TGG | AAA | AGT | ATT | CGT | CCT | AGT | ATT | CTT | CGC | TCA | TTA | GAC | 3288 |
| Asp | Glu | Glu | Trp | Lys | Ser | Ile | Arg | Pro | Ser | Ile | Leu | Arg | Ser | Leu | Asp | |
| | | | | 500 | | | | | 505 | | | | | 510 | | |
| TGG | TCA | ATA | GAT | TCT | TAT | GAA | TCA | TTG | ACA | CCG | TTA | AAA | GAA | GAG | TTA | 3336 |
| Trp | Ser | Ile | Asp | Ser | Tyr | Glu | Ser | Leu | Thr | Pro | Leu | Lys | Glu | Glu | Leu | |
| | | | 515 | | | | | 520 | | | | | 525 | | | |
| GAC | AAA | ACT | TAT | CAT | CAA | GTC | ATT | GAG | AAT | TGG | GAG | AAT | AAT | CCT | GCG | 3384 |
| Asp | Lys | Thr | Tyr | His | Gln | Val | Ile | Glu | Asn | Trp | Glu | Asn | Asn | Pro | Ala | |
| | | 530 | | | | | 535 | | | | | 540 | | | | |
| GTG | CAA | ATA | GAC | ACA | TTT | GCA | GGT | AAA | GAG | AGA | ATT | GTT | TTG | ACA | CCT | 3432 |

```
        Val Gln Ile Asp Thr Phe Ala Gly Lys Glu Arg Ile Val Leu Thr Pro
            545                 550                 555

TTA GAC AAA CAA CCA GAA CCT GAA TCA CTA CAA AAA CTA AAA CAA CAA      3480
        Leu Asp Lys Gln Pro Glu Pro Glu Ser Leu Gln Lys Leu Lys Gln Gln
        560                 565                 570                 575

ATA CAT ACG ATG TTG CCA AAT ATA GAT ATT CCT CAA TTA TTA CTC GAA      3528
        Ile His Thr Met Leu Pro Asn Ile Asp Ile Pro Gln Leu Leu Leu Glu
                            580                 585                 590

GTA AAT CGT TGG ACG GGA TTT ATG GAT GGT TTT CGA CAT ATT AGT GAG      3576
        Val Asn Arg Trp Thr Gly Phe Met Asp Gly Phe Arg His Ile Ser Glu
                        595                 600                 605

GCT AAA TCT AGA ATT AAC GAG TTA CCT ATA AGT ATC TGT GCA TTG CTT      3624
        Ala Lys Ser Arg Ile Asn Glu Leu Pro Ile Ser Ile Cys Ala Leu Leu
                    610                 615                 620

ATA TCT CAA GCA TGC AAT ATT GGG TTA AGA CCT TTA GTT CAA GAT GGG      3672
        Ile Ser Gln Ala Cys Asn Ile Gly Leu Arg Pro Leu Val Gln Asp Gly
                625                 630                 635

GTT CCT TCA TTA GAA CGT GAT CGT CTT ACA TGG ATT GAA CAA AAT TAT      3720
        Val Pro Ser Leu Glu Arg Asp Arg Leu Thr Trp Ile Glu Gln Asn Tyr
        640                 645                 650                 655

TTT CGT GCA GAA ACA CTT TCA GAA TCA AAC GCG AAA CTT GTA GAT TTT      3768
        Phe Arg Ala Glu Thr Leu Ser Glu Ser Asn Ala Lys Leu Val Asp Phe
                            660                 665                 670

CAT AGC CAA TTA CAG CTG GCT AAA ATG TGG GGT GGT GGA GAA ATT GCT      3816
        His Ser Gln Leu Gln Leu Ala Lys Met Trp Gly Gly Gly Glu Ile Ala
                        675                 680                 685

TCA GCT GAT GGA TTA CGT TTC ATC ACA CCA GTA AAA TCC GTA CAC ACT      3864
        Ser Ala Asp Gly Leu Arg Phe Ile Thr Pro Val Lys Ser Val His Thr
                    690                 695                 700

GGT CCA AAT CCT AAA TAT TTC GGT TCT GGT CGT GGT GTT ACG TAT TAC      3912
        Gly Pro Asn Pro Lys Tyr Phe Gly Ser Gly Arg Gly Val Thr Tyr Tyr
                705                 710                 715

AAC TAT ACG AGC GAT CAA TTT ACC GGA CTC CAC GGT TTG GTG ATT CCA      3960
        Asn Tyr Thr Ser Asp Gln Phe Thr Gly Leu His Gly Leu Val Ile Pro
        720                 725                 730                 735

GGC ACA ATT CGT GAT TCA TTA TAC TTA CTT CAA TGT GTG TTA GAA CAA      4008
        Gly Thr Ile Arg Asp Ser Leu Tyr Leu Leu Gln Cys Val Leu Glu Gln
                            740                 745                 750

AAT ACG AAC TTA CAG CCA AAA GAA ATT ATG ACA GAT ACA GCT GGG TAT      4056
        Asn Thr Asn Leu Gln Pro Lys Glu Ile Met Thr Asp Thr Ala Gly Tyr
                        755                 760                 765

AGT GAT ATT ATT TTT GGG CTC TTT GGA TTA TTA GGA TAT CAA TTT AGT      4104
        Ser Asp Ile Ile Phe Gly Leu Phe Gly Leu Leu Gly Tyr Gln Phe Ser
                    770                 775                 780

CCT CGT TTA GCT GAT ATC AGT GAA TCA CGT CTT TGG CGT TTT GAT GCG      4152
        Pro Arg Leu Ala Asp Ile Ser Glu Ser Arg Leu Trp Arg Phe Asp Ala
                785                 790                 795

AAC TCA GAT TAT AGC ATG TTA AAT AAT TTG TCT AAA AGT CGC ATT CGT      4200
        Asn Ser Asp Tyr Ser Met Leu Asn Asn Leu Ser Lys Ser Arg Ile Arg
        800                 805                 810                 815

GAA GAA CTC ATA CAT CGT CAT TGG GAA GAC ATG CTT CGT GTT GCG GGA      4248
        Glu Glu Leu Ile His Arg His Trp Glu Asp Met Leu Arg Val Ala Gly
                            820                 825                 830

TCT TTG AAA CTA AAT AAA ATA AAT GCA ACA CAT CTT ATC CAA GCA CTT      4296
        Ser Leu Lys Leu Asn Lys Ile Asn Ala Thr His Leu Ile Gln Ala Leu
                        835                 840                 845

CAG TAT AAT GGG AAA CCA ACT ATG TTA GGG CGA GCA ATT GGA GAA TTG      4344
        Gln Tyr Asn Gly Lys Pro Thr Met Leu Gly Arg Ala Ile Gly Glu Leu
                    850                 855                 860

GGG AGA CTC TTT AAA ACA CGT TAT TTA CTC TTA TAT TTA CAT GAT GAA      4392
```

|  |  |  |  |  |  |  |  |  |  |  |  |  |  |  |  |  |
|---|---|---|---|---|---|---|---|---|---|---|---|---|---|---|---|---|
| Gly | Arg | Leu | Phe | Lys | Thr | Arg | Tyr | Leu | Leu | Leu | Tyr | Leu | His | Asp | Glu | |
|  | 865 |  |  |  | 870 |  |  |  |  | 875 |  |  |  |  |  | |

| AAT | TAT | CGT | CGT | AAA | ATT | TTA | AAT | CAA | CTC | AAT | AGA | GGG | GAA | GCA | AGG | 4440 |
|---|---|---|---|---|---|---|---|---|---|---|---|---|---|---|---|---|
| Asn | Tyr | Arg | Arg | Lys | Ile | Leu | Asn | Gln | Leu | Asn | Arg | Gly | Glu | Ala | Arg | |
| 880 |  |  |  |  | 885 |  |  |  |  | 890 |  |  |  |  | 895 | |

| CAT | AGT | TTA | GCG | AGG | GCT | GTA | TTT | TAC | GGC | AAA | CGT | GGA | GAA | CTT | CAT | 4488 |
|---|---|---|---|---|---|---|---|---|---|---|---|---|---|---|---|---|
| His | Ser | Leu | Ala | Arg | Ala | Val | Phe | Tyr | Gly | Lys | Arg | Gly | Glu | Leu | His | |
|  |  |  |  | 900 |  |  |  |  | 905 |  |  |  |  | 910 |  | |

| CAA | TCC | TAT | CGA | GAA | GGA | CAA | GAA | GAG | CAA | TTA | GGT | GCA | TTA | GGT | TTA | 4536 |
|---|---|---|---|---|---|---|---|---|---|---|---|---|---|---|---|---|
| Gln | Ser | Tyr | Arg | Glu | Gly | Gln | Glu | Glu | Gln | Leu | Gly | Ala | Leu | Gly | Leu | |
|  |  |  | 915 |  |  |  |  | 920 |  |  |  |  | 925 |  |  | |

| GTA | GTA | AAT | GCA | ATT | ATT | GTA | TGG | AAT | ACA | CGA | TAT | ATA | GAA | TCT | GCG | 4584 |
|---|---|---|---|---|---|---|---|---|---|---|---|---|---|---|---|---|
| Val | Val | Asn | Ala | Ile | Ile | Val | Trp | Asn | Thr | Arg | Tyr | Ile | Glu | Ser | Ala | |
|  |  | 930 |  |  |  |  | 935 |  |  |  |  | 940 |  |  |  | |

| TTA | CAA | GTA | CTC | CGA | AAT | CGC | GGT | CAT | ACA | ATT | GAT | AAT | GAT | GAT | ATA | 4632 |
|---|---|---|---|---|---|---|---|---|---|---|---|---|---|---|---|---|
| Leu | Gln | Val | Leu | Arg | Asn | Arg | Gly | His | Thr | Ile | Asp | Asn | Asp | Asp | Ile | |
|  | 945 |  |  |  |  | 950 |  |  |  |  | 955 |  |  |  |  | |

| TCT | AGA | CTT | TCA | CCA | TTA | GGC | CAT | AAA | CAC | ATT | AAC | ATA | GTA | GGT | CGG | 4680 |
|---|---|---|---|---|---|---|---|---|---|---|---|---|---|---|---|---|
| Ser | Arg | Leu | Ser | Pro | Leu | Gly | His | Lys | His | Ile | Asn | Ile | Val | Gly | Arg | |
| 960 |  |  |  |  | 965 |  |  |  |  | 970 |  |  |  |  | 975 | |

| TAT | TCA | TTT | GTT | CTC | CCA | GAA | GAA | GTA | AAA | GAT | GGG | CAA | TTA | CGT | ACA | 4728 |
|---|---|---|---|---|---|---|---|---|---|---|---|---|---|---|---|---|
| Tyr | Ser | Phe | Val | Leu | Pro | Glu | Glu | Val | Lys | Asp | Gly | Gln | Leu | Arg | Thr | |
|  |  |  | 980 |  |  |  |  | 985 |  |  |  |  | 990 |  |  | |

| CTA | ACA | TAT | GAA | GAA | ACA | AAC | AAA | AAG | GAA | CCT | GAT | TCT | TTA | TAAGAATAGG | | 4780 |
|---|---|---|---|---|---|---|---|---|---|---|---|---|---|---|---|---|
| Leu | Thr | Tyr | Glu | Glu | Thr | Asn | Lys | Lys | Glu | Pro | Asp | Ser | Leu |  | | |
|  |  | 995 |  |  |  |  | 1000 |  |  |  |  | 1005 |  |  | | |

TTCCTAATGT CCGCTAATGC TTGTTGCGTG ATTTGTTCC ATTGCTACAC ATACCCC  4837

( 2 ) INFORMATION FOR SEQ ID NO:2:

( i ) SEQUENCE CHARACTERISTICS:
        ( A ) LENGTH: 306 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Met | His | Ser | Thr | Lys | Thr | Ile | Ser | Ile | Gln | Ala | Thr | Ser | Leu | Ile | Ser |
|---|---|---|---|---|---|---|---|---|---|---|---|---|---|---|---|
| 1 |  |  |  | 5 |  |  |  |  | 10 |  |  |  |  | 15 |  |

| Asp | Phe | Ile | Ser | Ser | Leu | Ser | Gln | Glu | Gly | Asp | Leu | His | Thr | Lys | Thr |
|---|---|---|---|---|---|---|---|---|---|---|---|---|---|---|---|
|  |  |  | 20 |  |  |  |  | 25 |  |  |  |  | 30 |  |  |

| Leu | Lys | Glu | Tyr | Thr | Ser | Asp | Leu | Lys | Asp | Phe | Val | Phe | Trp | Phe | Glu |
|---|---|---|---|---|---|---|---|---|---|---|---|---|---|---|---|
|  |  | 35 |  |  |  |  | 40 |  |  |  |  | 45 |  |  |  |

| Asn | Val | Trp | Gly | Lys | His | Ala | Glu | Asp | Thr | Leu | Phe | His | Pro | Ile | Glu |
|---|---|---|---|---|---|---|---|---|---|---|---|---|---|---|---|
|  | 50 |  |  |  |  | 55 |  |  |  |  | 60 |  |  |  |  |

| Val | Thr | Ala | Arg | Thr | Ile | Ala | Arg | Tyr | Arg | Gly | His | Met | Gln | Val | Thr |
|---|---|---|---|---|---|---|---|---|---|---|---|---|---|---|---|
| 65 |  |  |  |  | 70 |  |  |  |  | 75 |  |  |  |  | 80 |

| Arg | Leu | Leu | Lys | Pro | Ser | Thr | Ile | Asn | Arg | Arg | Ile | Asn | Ser | Ile | Lys |
|---|---|---|---|---|---|---|---|---|---|---|---|---|---|---|---|
|  |  |  |  | 85 |  |  |  |  | 90 |  |  |  |  | 95 |  |

| Arg | Tyr | Phe | Asp | Trp | Ala | Lys | Gln | Lys | Gly | Leu | Val | Gln | Thr | Asn | Tyr |
|---|---|---|---|---|---|---|---|---|---|---|---|---|---|---|---|
|  |  |  | 100 |  |  |  |  | 105 |  |  |  |  | 110 |  |  |

| Ser | Lys | Ser | Ile | Lys | Phe | Val | Pro | Thr | Glu | Lys | Thr | Ser | Pro | Lys | Arg |
|---|---|---|---|---|---|---|---|---|---|---|---|---|---|---|---|
|  |  | 115 |  |  |  |  | 120 |  |  |  |  | 125 |  |  |  |

| Met | Ser | Asp | Lys | Glu | Glu | Ala | Ala | Leu | Met | His | Ala | Val | Glu | Lys | Tyr |
|---|---|---|---|---|---|---|---|---|---|---|---|---|---|---|---|
|  | 130 |  |  |  |  | 135 |  |  |  |  | 140 |  |  |  |  |

| Gly | Thr | Leu | Arg | Asp | Arg | Ala | Met | Ile | Ile | Phe | Met | Leu | His | Thr | Gly |
|---|---|---|---|---|---|---|---|---|---|---|---|---|---|---|---|
| 145 |  |  |  |  | 150 |  |  |  |  | 155 |  |  |  |  | 160 |

| Leu | Arg | Ser | Met | Glu | Val | Cys | Asp | Val | Gln | Ile | Glu | Asp | Val | Ile | Met |
|---|---|---|---|---|---|---|---|---|---|---|---|---|---|---|---|

|   |   |   | 165 |   |   |   | 170 |   |   |   | 175 |   |   |
|---|---|---|---|---|---|---|---|---|---|---|---|---|---|

Arg Lys Arg Gly Gly Tyr Val Val Arg Ser Gly Lys Arg Asn Lys
            180                 185             190

Gln Arg Glu Val Pro Leu Asn Ser Thr Ala Arg Cys Ala Leu Glu Glu
        195                 200             205

His Ile Arg Leu Ser Glu Ile Ser Gln Ser Tyr Leu Phe Pro Ser Ser
    210                 215                 220

Lys Thr Gly Lys Arg Leu Gln Glu Arg Ala Ile Arg His Ile Leu Gln
225                     230                 235                     240

Lys Tyr Ile Arg Leu Ala Lys Leu Glu Gly Phe Ser Ala His Asp Leu
                245                 250                 255

Arg His Arg Phe Gly Tyr Val Met Ala Glu Arg Thr Pro Leu His Arg
            260                 265                 270

Leu Ala Gln Ile Met Gly His Asp Asn Leu Asn Thr Thr Met Ile Tyr
        275                 280                 285

Val Arg Ala Thr Gln Glu Asp Leu Gln Gly Glu Val Glu Lys Ile Ala
    290                 295                 300

Trp Asn
305

( 2 ) INFORMATION FOR SEQ ID NO:3:

( i ) SEQUENCE CHARACTERISTICS:
        ( A ) LENGTH: 1005 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

Met Pro Val Asp Phe Leu Thr Pro Glu Gln Glu Glu Lys Tyr Gly Cys
1               5                   10                  15

Phe Cys Asp Thr Pro Thr Ser Glu Gln Leu Ala Lys Tyr Phe Trp Leu
            20                  25                  30

Asp Asp Thr Asp Lys Glu Leu Ile Trp Asn Arg Arg Gly Glu His Asn
        35                  40                  45

Gln Leu Gly Phe Ala Val Gln Leu Gly Thr Val Arg Phe Leu Gly Thr
    50                  55                  60

Phe Leu Ser Asp Pro Thr Asn Val Pro Gln Ser Val Ile Thr Tyr Met
65                  70                  75                      80

Ala Asn Gln Leu His Leu Asp Ala Gln Ser Phe Ser Arg Tyr Arg Asn
                85                  90                  95

Lys Arg Ser Gln Trp Asp Gln Met Gln Glu Ile Arg Ser Val Tyr Gly
            100                 105                 110

Tyr Lys Asn Phe Thr Asp Lys Ser Thr His Trp Arg Phe Ile Arg Trp
        115                 120                 125

Leu Tyr Ala Arg Ala Trp Leu Tyr Asn Glu Arg Pro Ser Val Leu Phe
    130                 135                 140

Asp Leu Ala Thr Ala Arg Cys Ile Glu Gln Lys Ile Leu Leu Pro Gly
145                 150                 155                 160

Val Ser Val Leu Thr Arg Leu Val Ser Thr Val Arg Asp Arg Ser Ala
                165                 170                 175

Glu Asn Ile Trp Lys Lys Leu Ser Ser Leu Pro Asp Asn Val Gln Lys
            180                 185                 190

Lys Gln Leu Glu Asn Leu Leu Gln Ile Asp Gln Lys Thr Lys Lys Thr
        195                 200                 205

| | | | | | | | | | | | | | | |
|---|---|---|---|---|---|---|---|---|---|---|---|---|---|---|
| Tyr | Leu 210 | Glu | Arg | Leu | Ser | Asn 215 | Pro | Pro | Val | Pro 220 | Ile | Ser | Val | Thr | Gly |
| Ile 225 | Lys | Asn | Thr | Leu | Ile 230 | Arg | Leu | Gln | Glu | Leu 235 | Arg | Gln | Leu | Asn | Thr 240 |
| Glu | Asn | Trp | Asp | Met 245 | Ser | Arg | Ile | Pro | Ser 250 | Lys | Arg | Leu | Gln | Gln 255 | Phe |
| Ala | Arg | His | Thr 260 | Val | Ala | Val | Arg | Ser 265 | Gln | Ala | Ile | Ala | Arg 270 | Met | Pro |
| Asp | Gln | Arg 275 | Arg | Met | Ala | Met | Leu 280 | Val | Ala | Phe | Ala | Lys 285 | Met | Tyr | Thr |
| Gln | Ser 290 | Ala | Gln | Asp | Asp | Val 295 | Ile | Asp | Ile | Phe | Asp 300 | Arg | Tyr | Leu | Thr |
| Asp 305 | Leu | Phe | Ala | Lys | Thr 310 | Tyr | Arg | Lys | Glu | Gln 315 | Lys | Glu | Arg | Leu | Arg 320 |
| Thr | Ile | Lys | Asp | Leu 325 | Asp | Lys | Ala | Ala | Arg 330 | Gln | Leu | Arg | Glu | Ala 335 | Cys |
| Val | Ile | Leu | Leu 340 | Glu | His | Thr | Asp | Pro 345 | Ser | Val | His | Pro | Lys 350 | Thr | Ala |
| Val | Phe | Glu 355 | Lys | Ile | Ser | Glu | Lys 360 | Asp | Leu | Ile | Gln | Ala 365 | Val | Gln | Ile |
| Val | Asp 370 | Ser | Leu | Thr | Tyr | Ser 375 | Pro | Asn | Gln | Thr | Leu 380 | Ala | Tyr | Ser | Gly |
| Leu 385 | Leu | Gln | His | Tyr | Gly 390 | Ile | Ile | Arg | Lys | Phe 395 | Leu | Pro | Leu | Leu | Met 400 |
| Glu | Glu | Ile | Glu | Leu 405 | Gln | Ala | Thr | Pro | Ala 410 | Gly | Leu | Pro | Ile | Leu 415 | Gln |
| Ala | Trp | Asn | Phe 420 | Val | Lys | Glu | His | Gly 425 | Lys | Ser | Asn | Lys | Lys 430 | Arg | Trp |
| Lys | Asn | Ala 435 | Pro | Leu | Ala | Gly | Leu 440 | Asn | Ala | Asn | Trp | Ser 445 | Lys | Val | Val |
| Ile | Asp 450 | Lys | Asp | Ser | Gly | Thr 455 | Val | Asn | His | Arg | Ala 460 | Tyr | Thr | Phe | Trp |
| Met 465 | Leu | Glu | Gln | Val | Leu 470 | Glu | Ala | Leu | His | Arg 475 | His | Asp | Leu | Tyr | Ile 480 |
| Val | Gly | Ser | Glu | Lys 485 | Tyr | Gly | Asp | Leu | Arg 490 | Ala | Gln | Leu | Leu | Gln 495 | Asp |
| Glu | Glu | Trp | Lys 500 | Ser | Ile | Arg | Pro | Ser 505 | Ile | Leu | Arg | Ser | Leu 510 | Asp | Trp |
| Ser | Ile | Asp 515 | Ser | Tyr | Glu | Ser | Leu 520 | Thr | Pro | Leu | Lys | Glu 525 | Glu | Leu | Asp |
| Lys | Thr 530 | Tyr | His | Gln | Val | Ile 535 | Glu | Asn | Trp | Glu | Asn 540 | Asn | Pro | Ala | Val |
| Gln 545 | Ile | Asp | Thr | Phe | Ala 550 | Gly | Lys | Glu | Arg | Ile 555 | Val | Leu | Thr | Pro | Leu 560 |
| Asp | Lys | Gln | Pro | Glu 565 | Pro | Glu | Ser | Leu | Gln 570 | Lys | Leu | Lys | Gln | Gln 575 | Ile |
| His | Thr | Met | Leu 580 | Pro | Asn | Ile | Asp | Ile 585 | Pro | Gln | Leu | Leu | Leu 590 | Glu | Val |
| Asn | Arg | Trp 595 | Thr | Gly | Phe | Met | Asp 600 | Gly | Phe | Arg | His | Ile 605 | Ser | Glu | Ala |
| Lys | Ser 610 | Arg | Ile | Asn | Glu | Leu 615 | Pro | Ile | Ser | Ile | Cys 620 | Ala | Leu | Leu | Ile |
| Ser 625 | Gln | Ala | Cys | Asn | Ile 630 | Gly | Leu | Arg | Pro | Leu 635 | Val | Gln | Asp | Gly | Val 640 |

Pro Ser Leu Glu Arg Asp Arg Leu Thr Trp Ile Glu Gln Asn Tyr Phe
            645                 650                 655

Arg Ala Glu Thr Leu Ser Glu Ser Asn Ala Lys Leu Val Asp Phe His
            660                 665                 670

Ser Gln Leu Gln Leu Ala Lys Met Trp Gly Gly Gly Glu Ile Ala Ser
            675                 680                 685

Ala Asp Gly Leu Arg Phe Ile Thr Pro Val Lys Ser Val His Thr Gly
            690                 695                 700

Pro Asn Pro Lys Tyr Phe Gly Ser Gly Arg Gly Val Thr Tyr Tyr Asn
705                 710                 715                 720

Tyr Thr Ser Asp Gln Phe Thr Gly Leu His Gly Leu Val Ile Pro Gly
            725                 730                 735

Thr Ile Arg Asp Ser Leu Tyr Leu Leu Gln Cys Val Leu Glu Gln Asn
            740                 745                 750

Thr Asn Leu Gln Pro Lys Glu Ile Met Thr Asp Thr Ala Gly Tyr Ser
            755                 760                 765

Asp Ile Ile Phe Gly Leu Phe Gly Leu Leu Gly Tyr Gln Phe Ser Pro
            770                 775                 780

Arg Leu Ala Asp Ile Ser Glu Ser Arg Leu Trp Arg Phe Asp Ala Asn
785                 790                 795                 800

Ser Asp Tyr Ser Met Leu Asn Asn Leu Ser Lys Ser Arg Ile Arg Glu
            805                 810                 815

Glu Leu Ile His Arg His Trp Glu Asp Met Leu Arg Val Ala Gly Ser
            820                 825                 830

Leu Lys Leu Asn Lys Ile Asn Ala Thr His Leu Ile Gln Ala Leu Gln
            835                 840                 845

Tyr Asn Gly Lys Pro Thr Met Leu Gly Arg Ala Ile Gly Glu Leu Gly
            850                 855                 860

Arg Leu Phe Lys Thr Arg Tyr Leu Leu Leu Tyr Leu His Asp Glu Asn
865                 870                 875                 880

Tyr Arg Arg Lys Ile Leu Asn Gln Leu Asn Arg Gly Glu Ala Arg His
            885                 890                 895

Ser Leu Ala Arg Ala Val Phe Tyr Gly Lys Arg Gly Glu Leu His Gln
            900                 905                 910

Ser Tyr Arg Glu Gly Gln Glu Glu Gln Leu Gly Ala Leu Gly Leu Val
            915                 920                 925

Val Asn Ala Ile Ile Val Trp Asn Thr Arg Tyr Ile Glu Ser Ala Leu
            930                 935                 940

Gln Val Leu Arg Asn Arg Gly His Thr Ile Asp Asn Asp Asp Ile Ser
945                 950                 955                 960

Arg Leu Ser Pro Leu Gly His Lys His Ile Asn Ile Val Gly Arg Tyr
            965                 970                 975

Ser Phe Val Leu Pro Glu Glu Val Lys Asp Gly Gln Leu Arg Thr Leu
            980                 985                 990

Thr Tyr Glu Glu Thr Asn Lys Lys Glu Pro Asp Ser Leu
            995                 1000                1005

( 2 ) INFORMATION FOR SEQ ID NO:4:

( i ) SEQUENCE CHARACTERISTICS:
      ( A ) LENGTH: 85 amino acids
      ( B ) TYPE: amino acid
      ( D ) TOPOLOGY: linear ( i i ) MOLECULE TYPE: protein ( x i ) SEQUENCE DESCRIPTION: SEQ ID NO:4:

| Met | Ala | Ile | Arg | Lys | Asp | Glu | Leu | Tyr | Arg | Leu | Ile | Asp | His | Leu | Asp |
| 1 | | | | 5 | | | | | 10 | | | | | 15 | |
| Gln | Gln | Asp | Glu | Lys | Ala | Ala | Phe | Asp | Phe | Leu | Glu | Phe | Leu | Val | Gln |
| | | | 20 | | | | | 25 | | | | | 30 | | |
| Arg | Ser | Arg | Arg | Lys | Pro | Lys | Glu | Trp | Glu | Lys | Ile | Asp | Met | Ala | Asp |
| | | 35 | | | | | 40 | | | | | 45 | | | |
| Pro | Asp | His | Glu | Pro | Leu | Ser | Thr | Gln | Glu | Leu | Glu | Gln | Leu | Asn | Ser |
| | 50 | | | | | 55 | | | | | 60 | | | | |
| Glu | Glu | Gly | Tyr | Val | Ser | Gly | Glu | Asp | Ala | Lys | Arg | Glu | Phe | Gly | Leu |
| 65 | | | | | 70 | | | | | 75 | | | | | 80 |
| Gln | Ile | Asp | Leu | Pro | | | | | | | | | | | |
| | | | | 85 | | | | | | | | | | | |

RECOMBINANT *BACILLUS THURINGIENSIS* STRAINS, INSECTICIDAL COMPOSITIONS AND METHOD OF USE

RELATED APPLICATIONS

This application is a continuation-in-part of U.S. patent application Ser. No. 08/266,408, filed Jun. 24, 1994, which is a continuation-in-part of U.S. patent application Ser. No. 08/089,986, filed Jul. 8, 1993, now U.S. Pat. No. 5,441,884.

FIELD OF THE INVENTION

The present invention relates to a novel transposon isolated from *Bacillus thuringiensis* and its use in a site-specific recombination system for the construction of recombinant *Bacillus thuringiensis* strains that contain one or more insecticidal toxin genes introduced from other *Bacillus thuringiensis* strains and that are useful as insecticides.

BACKGROUND OF THE INVENTION

*Bacillus thuringiensis* ("*B.t.*") is a gram-positive soil bacterium that produces proteinaceous crystalline inclusions during sporulation. These *B.t.* crystal proteins are often highly toxic to specific insects. Insecticidal activities have been identified for crystal proteins from various *B.t.* strains against insect larvae from the insect orders Lepidoptera (caterpillars), Diptera (mosquitos, flies) and Coleoptera (beetles).

Recently certain *B.t.* strains and *B.t.* crystal proteins have been reported as having activity against noninsect species such as nematodes. The term "insecticidal," as used herein with reference to *B.t.* strains and their crystal proteins, is intended to include such pathogenic activities against non-insect species.

Individual *B.t.* crystal proteins, also called delta-endotoxins or parasporal crystals or toxin proteins, can differ extensively in their structure and insecticidal activity. These insecticidal proteins are encoded by genes typically located on large plasmids, greater than 30 megadaltons (mDa) in size, that are found in *B.t.* strains. A number of these *B.t.* toxin genes have been cloned and the insecticidal crystal protein products characterized for their specific insecticidal properties. A good review of cloned *B.t.* toxin genes and crystal proteins is given by Höfte et al., *Microbiol. Rev.* 53:242–255 (1989) (hereinafter Höfte and Whiteley, 1989), who also propose a useful nomenclature and classification scheme that has been adopted in this disclosure.

The insecticidal properties of *B.t.* have been long recognized, and *B.t.* strains were first commercially introduced in biological insecticide products in the 1960's. Commercialized *B.t.* insecticide formulations typically contain dried *B.t.* fermentation cultures whose crystal protein is toxic to various insect species and, in the past, were derived from "wild-type" *B.t.* strains, i.e., purified cultures of *B.t.* strains isolated from natural sources.

Several newly commercialized *B.t.* strains are genetically altered strains that have increased insecticidal potency as well as insecticidal activity against a broader spectrum of target insects, as compared with the parent *B.t.* strains. Such strains are exemplified in International Patent Publication No. WO 88/08877, published Nov. 17, 1988 by applicant Ecogen Inc., and its counterpart U.S. Pat. No. 5,080,897 issued to González et al. on Jan. 14, 1992.

Development of these genetically altered *B.t.* strains did not involve recombinant DNA technology but was instead based on the techniques of plasmid conjugal transfer, which is a natural form of genetic exchange between bacteria, and of plasmid curing, in which certain nonessential plasmids are deleted from a bacterium.

Plasmid conjugal transfer, or conjugation, is limited by the fact that many plasmids carrying useful toxin genes are not amenable to transfer from their native host *B.t.* strain to another "recipient" *B.t.* strain. Furthermore, some plasmids which can be transferred by conjugation are inherently incompatible with other plasmids, so a stable "transconjugant" *B.t.* strain, containing the two desired, incompatible plasmids, cannot be constructed.

Another drawback to conjugation is that some mobilizable, or transferable, plasmids carry undesirable toxin genes in addition to the desired gene, so the quantity of the desired crystal protein produced is limited by concurrent production of an unwanted crystal protein.

Despite the demonstrated efficacy of commercialized transconjugant *B.t.* strains against certain target insects, there is a clear need for improved *B.t.* strains against other insect pests. Development of such *B.t.* strains will be facilitated by use of recombinant DNA technology in *B.t.* strain construction.

Recombinant DNA procedures provide great flexibility in the construction of novel plasmids containing one or more toxin genes, by permitting selection, manipulation and control of crystal protein type and production and of gene regulation and expression. Some techniques for utilizing the recombinant DNA approach in the production of transformed *B.t.* strains are described in European Patent Application Publication No. EP 0 342 633, published Nov. 23, 1989 by applicant Ciba-Geigy AG, and in European Patent Application Publication No. 0 537 105, published Apr. 14, 1993 by applicant Sandoz Ltd.

The recombinant *B.t.* strains disclosed in EP 0 342 633, EP 0 537 105 and other publications are generally characterized by the presence of one or more antibiotic resistance marker genes on the recombinant plasmid harboring the desired *B.t.* toxin gene(s). Such antibiotic resistance marker genes provide a means for the identification and selection of transformed *B.t.* strains containing the recombinant toxin-encoding plasmid but are undesirable in viable *B.t.* strains developed for use in commercial insecticide formulations. Since antibiotic resistance genes are not ordinarily present in native *B.t.* strains, pesticide and environmental regulatory agencies may be reluctant to approve antibiotic-resistant recombinant *B.t.* strains for unrestricted environmental release and for use in biological insecticide formulations.

A major reason for the presence of antibiotic resistance genes in recombinant *B.t.* strains described in the literature is the use of bifunctional cloning vectors containing such resistance marker genes. Portions of these cloning vectors are typically derived from plasmids not native to *B.t.*, e.g., *Escherichia coli*, *Bacillus cereus*, *Bacillus subtilis* or *Staphylococcus aureus* plasmids, and contain, in addition to the antibiotic resistance marker gene, an origin of replication from a non-*B.t.* source that is also functional in *B.t.* and therefore permits the cloning vector to be replicated and maintained in *B.t.*

International Patent Publication No. WO 91/18102, published Nov. 28, 1990 by applicant Ecogen Inc., describes a plasmid shuttle vector for recombinant *B.t.* strain development that facilitates incorporation of recombinant plasmids into *B.t.* strain constructs that contain no DNA derived from *E. coli* or other non-*B.t.* biological sources. Using this shuttle vector, a cloned *B.t.* toxin gene and *B.t.* plasmid replication origin region are isolated as a single restriction fragment that, upon self-ligation, is introduced into *B.t.* by cotransformation. This plasmid shuttle vector utilizes a *B.t.* replication origin derived from large resident plasmids of *B.t.*, a multiple cloning site and strategically placed restriction endonuclease cleavage sites to enable construction of *B.t.* strains that are free of antibiotic resistance marker genes and free of non-*B.t.* replication origins.

A second approach for constructing such *B.t.* strains is a multistep technique described by Lereclus et al., *Bio/Technology* 10:418–421 (1992) that relies on the presence of IS232 in a resident *B.t.* toxin plasmid to effect homologous recombination. A cloned *B.t.* toxin gene is inserted within a cloned fragment of IS232 (which is found on some naturally occurring toxin-encoding *B.t.* plasmids) that is inserted into a shuttle plasmid thermosensitive for replication in *B.t.* The shuttle plasmid is then used to transform a *B.t.* strain containing the IS232 fragment on a resident *B.t.* plasmid, and transformants are selected at non-permissive temperature for clones in which the shuttle vector has integrated via homologous recombination into a copy of IS232 present on the resident plasmid. Subsequently, individual clones are screened for a second homologous recombination event that eliminates the shuttle vector and conserves the newly introduced toxin gene. This technique is limited by the laborious nature of its steps and its reliance on homologous recombination using IS232-containing resident *B.t.* plasmids, whose copy number cannot readily be altered to increase gene expression.

Removal of unwanted selectable marker genes or other unwanted DNA has been described for transgenic plants and eukaryotic cells via the so-called Cre/lox recombination system of bacteriophage P1, where the cre gene encoding the Cre recombinase enzyme is activated to delete the unwanted DNA, which is bracketed by lox recombination site sequences. International Patent Publication No. WO 93/01283, published Jan. 21, 1993 by applicant U.S. Department of Agriculture, and Dale et al., "Gene transfer with subsequent removal of the selection gene from the host genome," *Proc. Natl. Acad. Sci. U.S.A.* 88:10558–10562 (1991), describe such a system for removal of a antibiotic resistance marker gene from transgenic tobacco plants.

U.S. Pat. No. 4,959,317 issued Sep. 25, 1990 to Sauer describes the application of the Cre/lox recombination system to yeast cells and to a mouse cell line to delete or invert selected DNA sequences.

Höfte and Whiteley, 1989, in discussing factors such as conjugative plasmid transfer that account for the observed mobility of crystal protein genes among *B.t.* strains, note past reports of some cryIA-type genes and the cryIVB gene being associated with insertion sequence (IS) elements on transposon-like structures (see paragraph bridging pages 245–246). Nevertheless, the role of repeat sequence and/or insertion sequence elements and transposon-like structures in the mobility of *B.t.* crystal protein genes still remains speculative.

Among known *B.t.* strains, only one transposon (transposable element) has been reported in the literature as having been isolated from *B.t.* Mahillon et al., *EMBO J.* 7:1515–1526 (1988) provide a detailed description of this transposon, originally reported in a 1983 publication and now named Tn4430. Murphy, "Transposable Elements in Gram-Positive Bacteria," Chapt. 9 in *Mobile DNA*, Berg et al., eds., Am. Soc. Microbiol., Washington, D.C. (1989) pp. 269–288, likewise discusses Tn4430, in the context of other transposable elements found in gram-positive bacteria.

Mahillon et al., *Plasmid* 19:169–173 (1988), describe the cloning in *E. coli* and restriction mapping of three small cryptic plasmids from *B.t.* var. *thuringiensis*, one of the plasmids being pGI2 which was reported to contain the *B.t.* transposon Tn4430. The authors speculate (at page 173) that the cloned plasmids could serve as the starting point for the development of new shuttle vectors for *E. coli* and *B.t.* but offer no details concerning the construction and use of such hypothetical plasmid shuttle vectors. The complete nucleotide sequence of the small cryptic plasmid pGI2, including Tn4430, is reported by Mahillon et al. in *Nucl. Acids Res.* 16:11827–11828 (1988).

Earlier references cited by Mahillon et al. in *EMBO J.* 2:1515–1526 (1988) disclose that, although Tn4430 is widely distributed among *B.t.* species, the functional role of Tn4430 in *B.t.*, if any, remains unclear. Despite occasional mention in investigative research publications concerning *B.t.*, of Tn4430 and of homology of its elements with other known insertion sequence elements, this transposon has not been utilized to facilitate construction of insecticidal *B.t.* strains; see, e.g., Lereclus et al., *FEMS Microbiol. Lett.* 49:417–422 (1988).

The novel transposon of the present invention, designated Tn5401, is only the second transposon to be isolated from *B.t.* since the discovery of Tn4430 over ten years ago. Unlike Tn4430 which is widely distributed among *B.t.* species, transposon Tn5401 appears to be found in only a few relatively rare *B.t.* species.

The present invention also encompasses a site-specific recombination system for recombinant *B.t.* strain construction that preferably utilizes certain elements of transposon Tn5401, e.g., its internal resolution site and recombinase gene. The site-specific recombination system of this invention represents a significant advance over the approach described in International Patent Publication No. WO 91/18102 because it facilitates the rapid development and construction of recombinant *B.t.* strains whose recombinant plasmids possess highly desirable characteristics. They are completely free of foreign DNA from non-*B.t.* sources and can carry *B.t.* toxin genes that provide insecticidal properties superior to *B.t.* strains presently used in commercial bioinsecticides.

SUMMARY OF THE INVENTION

The transposable element of this invention is the isolated, purified transposon designated as Tn5401 and whose nucleotide base sequence (SEQ ID NO:1) is shown in FIG. 1, or a mutant thereof capable of functioning as a transposable element.

Several unique elements of Tn5401 are also within the scope of this invention. The locations of these elements are shown in the linear structural map of Tn5401 in FIG. 2. These elements include the isolated, purified DNA sequence containing the internal resolution site, "IRS", of Tn5401; the isolated, purified gene designated as the Tn5401 resolvase/recombinase gene, tnpI; and the isolated, purified gene designated as the Tn5401 transposase gene, tnpA.

The resolvase/recombinase gene product, the resolvase protein (SEQ ID NO:2), and the transposase gene product, the transposase protein (SEQ ID NO:3), are also within the scope of this invention. Recombinant plasmids containing either transposon Tn5401 or its internal resolution site, its resolvase/recombinase gene, or its transposase gene are also embodiments of the present invention, as are bacteria transformed with such recombinant plasmids and capable of expressing the applicable genes on such plasmids.

This invention also includes a plasmid shuttle vector useful for recombinant *Bacillus thuringiensis* (*B.t.*) strain development, which has (i) an origin of replication functional in *B.t.*, preferably one native to a *B.t.* plasmid, such as *B.t.* origin of replication ori43, ori43.9, ori44 or is ori60; (ii) DNA not native to *B.t.*, preferably selected from selectable marker genes and origins of replication functional in *E. coli* or in a Bacillus host species other than *B.t.*; (iii) optionally and preferably, one or more insecticidal protein toxin genes; (iv) two identical internal resolution sites oriented in the same direction and flanking the DNA not native to *B.t.*, thus enabling such non-*B.t.* DNA to be excised via a site-specific recombination event involving the two internal resolution sites. The internal resolution sites are preferably derived from a Tn3-type transposon and more preferably are identical to the internal resolution site of transposon Tn5401. Host *B.t.* strains or other bacterial strains transformed with this plasmid shuttle vector are also embodiments of this invention.

The method of constructing a recombinant *B.t.* strain containing no DNA elements foreign to *B.t.* is also within the scope of this invention, having the steps of (a) transforming a host *B.t.* strain with a plasmid shuttle vector containing (i) an origin of replication native to *B.t.*, (ii) DNA not native to *B.t.* and useful in the construction of recombinant *B.t.* strains, selected from the group consisting of selectable marker genes, origins of replication functional in *E. coli*, and origins of replication functional in a Bacillus host species other than *B.t.*, (iii) one or more insecticidal *B.t.* protein toxin genes, and (iv) two identical internal resolution sites oriented in the same direction and flanking the DNA not native to *B.t.*, the sites being the same as an internal resolution site from a Tn3-type transposon native to *B.t.*; (b) introducing into the transformed *B.t.* strain resolvase protein to effect a site-specific recombination event involving the internal resolution sites, thereby excising from the plasmid shuttle vector the DNA not native to *B.t.*; and (c) recovering a recombinant *B.t.* strain containing a recombinant plasmid capable of replicating in the *B.t.* strain and containing (i) an origin of replication native to *B.t.*, (ii) one or more insecticidal *B.t.* protein toxin genes, and (iii) a single internal resolution site, derived from the site-specific recombination event. Preferred Tn3-type transposon sources for the internal resolution site in the plasmid shuttle vector of this method are transposons Tn5401 and Tn4430.

The present invention also encompasses a recombinant plasmid capable of replicating in a *Bacillus thuringiensis* bacterium and having (i) at least one insecticidal protein toxin gene, (ii) an origin of replication functional in *B.t.*, and (iii) a single internal resolution sites preferably derived from a Tn3-type transposon and more preferably identical to the internal resolution site of transposon Tn5401. Host *B.t.* strains or other bacterial strains containing such recombinant plasmids are also embodiments of this invention, as are insecticidal compositions with such transformed host *B.t.* strains, and as is the method of controlling insect pests utilizing such insecticidal compositions.

BRIEF DESCRIPTION OF THE DRAWINGS

FIG. 1A-L consists of FIGS. 1A through 1L and depicts the nucleotide sequence for Tn5401, the transposon of this invention (SEQ ID NO:1). The deduced amino acid sequence for an open reading frame extending from nucleotide base positions 764 to 1681 (excluding the terminal nonsense codon) is also shown. The gene of this open reading frame, designated the resolvase gene, encodes a protein with 306 amino acids. The deduced amino acid sequence for another open reading frame, extending from nucleotide positions 1756 to 4770 (excluding the terminal nonsense codon), is also shown. The gene of this second open reading frame, designated the transposase gene, encodes a protein with 1005 amino acids. Certain restriction endonuclease cleavage sites (NsiI(2), NspI(2), ClaI, BssHII) are also shown.

Microorganism Deposits

To assure the availability of materials to those interested members of the public upon issuance of a patent on the present application, deposits of the following microorganisms were made prior to the filing of present application with the ARS Patent Collection, Agricultural Research Service Culture Collection, Northern Regional Research Laboratory (NRRL), 1815 North University Street, Peoria, Ill. 61604:

| Bacterial Strain | Recombinant Plasmid | NRRL Accession Number | Date of Deposit |
|---|---|---|---|
| E. coli EG7534 | pEG854 | NRRL B-18632 | March 17, 1990 |
| E. coli EG7669 | pEG922 | NRRL B-21068 | April 1, 1993 |
| E. coli EG7683 | pEG911-1 | NRRL B-21069 | April 1, 1993 |
| B. thuringiensis EG2158 | none | NRRL B-18213 | April 29, 1987 |
| B. thuringiensis EG7684 | pEG928.9 | NRRL B-21121 | July 7, 1993 |
| B. thuringiensis EG7673 | pEG930.9Δ | NRRL B-21070 | April 1, 1993 |
| B. thuringiensis EG7674 | pEG928.9Δ | NRRL B-21071 | April 1, 1993 |
| B. thuringiensis EG7681 | pEG931Δ | NRRL B-21072 | April 1, 1993 |
| B. thuringiensis EG7826 | pEG337Δ | NRRL B-21249 | May 10, 1994 |
| B. thuringiensis EG7841 | pEG935Δ | NRRL B-21250 | May 10, 1994 |
| B. thuringiensis EG7856 | pEG342Δ | NRRL B-21251 | May 10, 1994 |
| B. thuringiensis EG11621 | pEG935Δ | NRRL B-21506 | November 15, 1995 |
| B. thuringiensis | pEG361Δ | NRRL B-21507 | November 15, 1995 |
| B. thuringiensis EG11622 | pEG360Δ | NRRL B-21508 | November 15, 1995 |
| B. thuringiensis EG11724 | pEG348Δ | NRRL B-21578 | May 21, 1996 |
| B. thuringiensis EG7841-1 | none | NRRL B-21577 | May 21, 1996 |
| B. thuringiensis EG4923-4 | | | |

These microorganism deposits were made under the provisions of the "Budapest Treaty on the International Recognition of the Deposit of Microorganisms for the Purpose of Patent Procedure." All restrictions on the availability to the public of these deposited microorganisms will be irrevocably removed upon issuance of a United States patent based on this application.

DESCRIPTION OF THE PREFERRED EMBODIMENTS

The transposon, or transposable element, of this invention was isolated from *Bacillus thuringiensis* and has been designated as transposon Tn5401. Tn5401 has the nucleotide sequence (SEQ ID NO:1) shown in FIG. 1. Two open reading frames within transposon Tn5401 are also shown in FIG. 1, along with their respective deduced amino acid sequences, and these are discussed in more detail below.

A structural map of Tn5401 is shown in FIG. 2 and includes the location of open reading frames within this 4837 basepair (bp) transposon; these elements are indicated by segments with arrowheads. The genes of these open reading frames, orf1, tnpI and tnpA, are as follows:

orf1 (open arrow in FIG. 2) potentially encodes a cryptic protein, whose significance is not presently known, of 85 amino acids (10.1 kDa) in the 3'-5' direction. The deduced amino acid sequence of orf1 is shown in the Sequence Listing accompanying this specification and designated as SEQ ID NO:4. Although not shown in FIG. 1, it is derived from the complementary nucleotide sequence extending from nucleotide base positions 351 to 608.

tnpI (dark shaded arrow in FIG. 2) encodes a protein, designated the resolvase protein of Tn5401, of 306 amino acids (35,613 Da) in the 5'-3' direction. In FIG. 1, the resolvase gene encodes the resolvase protein having the amino acid sequence (SEQ ID NO:2) located between nucleotide base positions 763 to 1682. The nucleotide base sequence of the resolvase gene, as shown in FIG. 1, extends from nucleotide base positions 764 to 1681 (excluding the terminal nonsense codon).

tnpA (light shaded arrow in FIG. 2) encodes a protein, designated the transposase protein of Tn5401, of 1005 amino acids (116,250 Da) in the 5'-3' direction. In FIG. 1, the transposase gene encodes the transposase protein having the amino acid sequence (SEQ ID NO:3) located between nucleotide base positions 1755 to 4771. The nucleotide base sequence of the transposase gene, as shown in FIG. 1, extends from nucleotide base positions 1756 to 4770 (excluding the terminal nonsense codon).

Another important distinguishing characteristic of transposon Tn5401 is an internal resolution site, IRS, located 5' to the resolvase open reading frame, within a ~550 bp ClaI-NsiI fragment. This location of the IRS is shown by brackets on the linear structural map of FIG. 2 and has been designated in the Figure as "IRS region." In FIG. 1, the internal resolution site is located within the DNA fragment extending from nucleotide positions 217 (the initial nucleotide of a ClaI restriction endonuclease cleavage site) to 764 (the initial nucleotide of a NsiI restriction endonuclease cleavage site). The IRS located on this ClaI-NsiI fragment is believed to be situated on a ~150 bp fragment immediately upstream of (5' to) the resolvase open reading frame, i.e., upstream of the NsiI site that initiates the resolvase tnpI gene, in particular, within the DNA fragment extending from nucleotide base positions 608 to 763 shown in FIG. 1.

Figure 2:
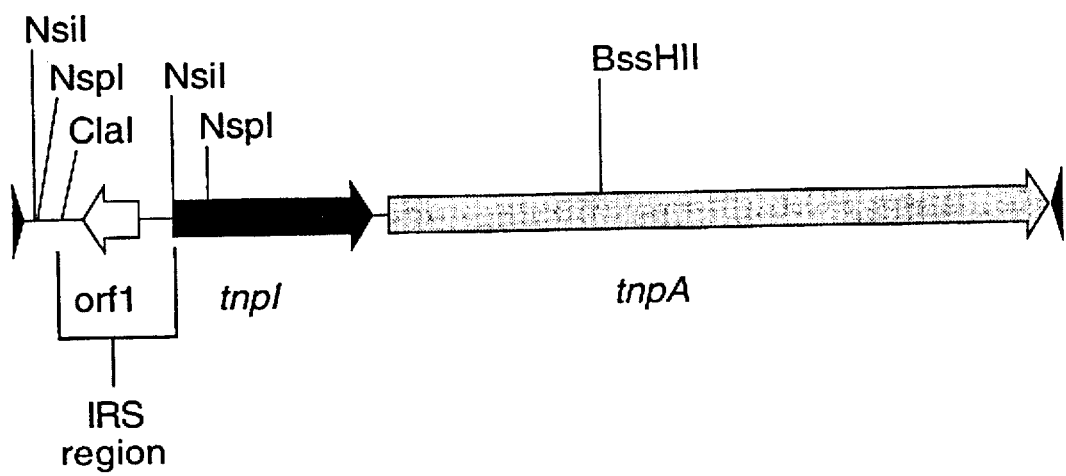
FIG. 2 is a linear structural map of transposon Tn5401 whose 4837 basepair nucleotide sequence is shown in FIG. 1. Three open reading frames are shown: "orf1" (open arrow) which encodes a cryptic protein of 85 amino acids in the 3'-5' direction; "tnpI" (dark shaded arrow), the resolvase gene; and "tnpA" (light shaded arrow), the transposase gene. An internal resolution site is located within the bracketed DNA fragment, "IRS region", shown in FIG. 2. Inverted repeats of 53 basepairs at either end of the structural map are shown as black arrowheads. Certain restriction endonuclease cleavage sites (NsiI(2), NspI(2), ClaI, BssHII) are also shown.

Transposon Tn5401 is also characterized by 53 bp inverted repeats at the termini, which are depicted by the solid black arrowheads in the structural map of FIG. 2.

Several restriction endonuclease cleavage sites, i.e., NsiI (two occurrences), NspI (two occurrences), ClaI (one occurrence), BssHII (one occurrence), are also shown on the linear structural map of Tn5401 in FIG. 2 and in the nucleotide sequence of FIG. 1, and these are useful for isolating the IRS, as well as the orf1, resolvase and transposase genes.

Transcriptional start sites within Tn5401 have been mapped by primer extension analysis, overlapping divergent promoters are located 5' to the resolvase gene: one directs the transcription of both tnpI and tnpA. Both promoters are derepressed on recombinant plasmids when the tnpI and tnpA genes are deleted, suggesting that transcription within the transposon is autoregulated, presumably by the resolvase protein.

Conserved sequence elements within the above-noted promoter region, in the intergenic region between orf1 and tnpI, apparently serve as recognition sites for the resolvase protein. Four copies of a conserved 12 bp sequence element are present within the above-noted promoter region and are the recognition/binding sites for the recombinase protein. Two copies of the 12 bp sequence element form a dyad sequence (nucleotide positions 639–666 in SEQ ID NO:1) that may be the site at which site-specific recombination actually occurs during the transposition process. All four copies of the 12 bp sequence are believed to be essential for site-specific recombination to occur. The 12 bp sequence is also located within the terminal inverted repeats of transposon Tn5401, thus accounting for the unusual length of these repeats.

Transposon Tn5401 appears to belong to the class of transposons designated as Tn3-type transposons, described by is Heffron in "Tn3 and Its Relatives" in *Mobile Genetic Elements*, Shapiro, ed., Academic Press, Orlando (1988), pp. 223–260. Transposons in the Tn3 family have the following characteristics:

(1) short inverted repeats at either end, which exhibit homology with other family members, (2) a high molecular weight protein (transposase) encoded by the transposon and essential for transposition;

(3) a two stage transposition mechanism involving fusion of donor (with transposon) and recipient DNA molecules, including a duplication of the transposon to form a cointegrate molecule, followed by a resolution/recombination event at an internal resolution site within each transposon copy to yield donor and recipient DNA molecules each containing the transposon;

(4) a recombinase protein encoded by the transposon and required for resolution of the cointegrate molecule;

(5) an internal site-specific recombination site that enables the resolvase protein to effect resolution/recombination of the cointegrate molecule; and (6) a 5-bp duplication of target DNA at the site of insertion, AT-rich target sites apparently being favored.

Members of the Tn3 family or class of transposons are predominantly derived from gram-negative bacteria, but one exception is Tn4430 originally isolated from a gram-positive organism and described by Mahillon et al., *EMBO J.* 7:1515–1526 (1988). Until the inventor's discovery of Tn5401, the prior art transposon Tn4430 was the only transposon reported to be originally isolated from a *B.t.* or *Bacillus* species.

Transposon Tn5401 is present in *B.t.* var. *morrisoni* strain EG2158 which produces a coleopteran-active protein encoded by a cryIIIA gene on an 88 megadalton (MDa) resident plasmid. Tn5401 is located on two resident plasmids of *B.t.* strain EG2158, a 35 MDa plasmid and a 72 MDa plasmid.

Subsequent to the discovery of Tn5401, the inventor has screened numerous other *B.t.* species and determined that Tn5401 is only rarely found among *B.t.* species. This finding contrasts with the prior art transposon Tn4430 which is widely distributed among *B.t.* species.

Transposon Tn5401 has been identified by the inventor as also being present in *B.t.* "tenebrionis" (DSM2803), also called *B.t.* "san diego", a *morrisoni* variety that is coleopteran toxic like *B.t.* strain EG2158.

The transposition mechanism of Tn5401 appears to be similar to that of other transposable elements in the Tn3 class. The transpositioning functionality of transposon Tn5401 is not limited to gram-positive bacteria such as *B.t.* but may likely also be demonstrated in gram-negative bacteria such as *E. coli*. For Tn5401 and other Tn3-type transposons, the net outcome of transposition is the insertion of a duplicate copy of the transposon into another (target) plasmid or chromosomal site. The first step of transposition involves the joinder, or cointegration, of a transposon-containing donor plasmid with a target plasmid to form a cointegrate DNA molecule that contains a duplicated copy of the transposon. The transposase gene in the transposon and its encoded protein transposase are essential for this initial step of transposition and apparently effect formation of the duplicate copy of the transposon in the cointegrate plasmid.

The second step of transposition involves a site-specific recombination event, in which the original transposon-containing donor plasmid and target plasmid, the latter now containing a copy of the transposon, are formed from the cointegrate plasmid. The site-specific recombination event occurs at a specific site in the transposon, the internal resolution site, referred to herein as the IRS. The resolvase protein encoded by the resolvase gene in the transposon apparently catalyzes a recombination event between the two internal resolution sites of the duplicate transposons, resulting in the formation of the transposon-containing donor plasmid and a target plasmid that has been modified by incorporation of a copy of the transposon.

The site-specific recombination event occurs between the duplicate internal resolution sites in the cointegrate molecule and has the effect of removing, or excising, the DNA located between the duplicate sites. The resolvase/recombinase protein encoded by the resolvase gene in the transposon can apparently catalyze this site-specific recombination event on any plasmid molecule containing two copies of the internal resolution site. These aspects of the transposition mechanism and of transposon Tn5401 are utilized in the site-specific recombination system of this invention, which is described in more detail below.

Transposon Tn5401 is also useful in transposon tagging to isolate genes of interest, e.g., in mutational studies of protein toxin genes in *B.t.* Transposons are known to be useful as molecular probes and genetic markers. In the event a transposon inserts itself into a gene, the gene is inactivated and a mutant phenotype is produced. Tn5401 is especially useful for such gene studies in *B.t.* since this transposon favors insertion into plasmid DNA rather than chromosomal DNA. The present invention, for this reason, includes use of recombinant plasmids containing Tn5401, preferably in conjunction with a selectable and/or screenable marker, e.g., an antibiotic resistance marker gene, functional in the host microorganism harboring the recombinant plasmid.

This invention also extends to mutants and derivatives (hereinafter referred to collectively as "mutants") of (i) transposon Tn5401 which are capable of functioning as transposable elements, (ii) the resolvase gene of Tn5401 whose resolvase/recombinase gene products have resolving functionality, and (iii) the transposase gene of Tn5401 whose transposase gene products have transpositioning functionality. Methods for creating or obtaining such mutants are well known to those skilled in the art of molecular cloning.

In another aspect of this invention, transposon Tn5401 has been isolated on a recombinant plasmid designated pEG922, whose circular restriction map is shown in FIG. 3. Transposon Tn5401 is located on a ~7 kb SstI-SstI DNA fragment in plasmid pEG922 and the tnpI and tnpA genes of Tn5401 are shown in FIG. 3. As is evident from FIG. 3, the transposon Tn5401 has been tagged with a selectable marker gene, tet, for tetracycline antibiotic resistance. The derivation of recombinant plasmid pEG922 is described in more detail in Example 2. Plasmid pEG922 is useful for its ability to transform gram-positive bacteria such as *B. thuringiensis, B. cereus, B. megaterium,* and *B. subtilis,* as well as transform gram-negative bacteria such as *E. coli,* and such transformed bacteria are capable of expressing the tnpI and tnpA genes on Tn5401. Consequently, transformed bacteria containing pEG922 are able to produce the recombinase/resolvase protein gene product of tnpI. Likewise, expression of the transposase protein gene product of tnpA enables the transposon to exhibit transpositioning functionality. Besides plasmid pEG922, other recombinant plasmids containing the transposon Tn5401 are also within the scope of this invention.

Other embodiments of this invention include a bacterium, e.g., pi Bacillus thuringiensisor *E. coli,* transformed with a recombinant plasmid carrying transposon Tn5401. *E. coli* strain EG7669 harbors recombinant plasmid pEG922 and is one such strain.

Additional embodiments of this invention also include recombinant plasmids containing either the tnpA gene or tnpI gene, or both, of Tn5401, as well as bacteria transformed with such recombinant plasmids and capable of expressing the gene or genes in such plasmids. Preferred bacteria include Bacillus species, particularly *B.t.,* and include *E. coli.*

The transposable element Tn5401 of this invention provides the basis for a site-specific recombination system for construction of stable recombinant plasmids in insecticidal recombinant *B.t.* strains that contain only DNA that is native to *B.t.* and that are free of foreign (non-*B.t.* derived) DNA. This site-specific recombination system utilizes the internal resolution site of Tn5401, two copies of the internal resolution site being incorporated into a recombinant *B.t.* plasmid in the same orientation. The two copies of the internal resolution site are used to bracket all DNA elements foreign to *B.t.,* e.g., selectable marker genes, *E. coli* replicons and other DNA useful in the construction and characterization of such a recombinant plasmid. Elimination of the foreign DNA is accomplished by a site-specific recombination event involving the internal resolution sites. This event is effected enzymatically by using the site-specific resolvase/recombinase protein that is encoded by the tnpl gene of Tn5401. The resultant recombinant plasmids are completely free of foreign DNA. Such recombinant *B.t.* plasmids, harboring a desired *B.t.* toxin gene or combinations of toxin genes, may be used to construct *B.t.* strains for use as the active ingredient in commercial *B.t.*-based insecticides.

An essential aspect of the site-specific recombination system of this invention is a plasmid shuttle vector having the following elements: (i) an origin of replication functional in *B.t.;* (ii) DNA not native to *B.t.;* and (iii) two identical internal resolution sites oriented in the same direction and flanking the DNA not native to *B.t.* The two identical internal resolution sites thus segregate the DNA not native to *B.t.* from the DNA native to *B.t.* Use of this plasmid shuttle vector in a *B.t.* host strain facilitates removal or excision of the non-*B.t.* DNA via a site-specific recombination event involving, i.e., between, the two internal resolution sites. The site-specific recombination event is catalyzed by the introduction of resolvase/recombinase protein that recognizes the particular IRS site utilized in the plasmid shuttle vector.

The plasmid shuttle vector optionally and preferably contains at least one insecticidal protein toxin gene that is intended to be introduced into the recombinant *B.t.* strain construct. This gene (or genes) is situated on the plasmid shuttle vector in a location outside of the DNA not native to *B.t.* and outside of the internal resolution sites that flank the foreign DNA.

One preferred embodiment of the plasmid shuttle vector of this invention is plasmid pEG928.9, whose circular structural map is shown in FIG. 4. Details of the derivation of plasmid shuttle vector pEG928.9 are described in Example 3.

The duplicate copies of the internal resolution sites (IRS) utilized in this plasmid shuttle vector are desirably derived from, or identical to, an IRS of a Tn3-type transposon.

Particularly suitable Tn3-type transposon sources for the IRS are transposons native to *B.t.* such as transposons Tn4430 and Tn5401. These IRS-source transposons are well suited for construction of insecticidal recombinant *B.t.* strains having no DNA that is not native to *B.t.* A disadvantage of Tn4430 as the IRS source is the widespread existence of this transposon in *B.t.* strains. The host *B.t.* strain selected for construction of the recombinant *B.t.* should be free of the transposon utilized as the IRS source in the plasmid shuttle vector, so as to avoid possible interference with the site-specific recombination event in the method of this invention.

For this reason, duplicate copies of the internal resolution site in the plasmid shuttle vector are most preferably derived from, or identical to, the internal resolution site of transposon Tn5401. As noted earlier in the discussion of Tn5401, this transposon is infrequently found in *B.t.* species, a fact that makes most *B.t.* strains suitable candidates as host strains for the site-specific recombination method of this invention.

It should be noted, however, that internal resolution sites or site-specific recombination sites from other sources are likewise usable in this plasmid shuttle vector and in the site-specific recombination system of this invention, if the fact of the IRS or the site-specific recombination site not being native to *B.t.* is not critical.

In the plasmid shuttle vector of this invention, the origin of replication functional in *B.t.* is preferably a replication origin that is native to *B.t.*, i.e., is identical to or derived from a *B.t.* plasmid origin of replication. *B.t.* replication origins from large *B.t.* plasmids, i.e., plasmids larger than about 20–25 mDa in size, are preferred since such replicons are more likely to produce stable recombinant plasmids than replicons derived from small *B.t.* plasmids, which typically replicate by a different mechanism, i.e., rolling circle replication.

Preferred *B.t.* plasmid origins of replications are ori43, ori60 and ori44, described in PCT International Patent Publication No. WO 91/18102, published Nov. 28, 1990 by applicant Ecogen Inc. The ori43 replicon is present in plasmid shuttle vector pEG854, which is contained in *E. coli* strain EG7534 which is a deposited microorganism described in WO 91/18102. The preferred *B.t.* origin of replication also includes mutants of these three and other *B.t.* replicons, particularly those mutants exhibiting higher copy numbers than the progenitor replicon. One such replicon, ori43.9, is utilized in plasmid shuttle vector pEG928.9 of this invention and is preferred because its high copy number characteristic often promotes increased expression levels of insecticidal toxin protein genes located on the same plasmid.

The plasmid shuttle vector of this invention also contains DNA elements not native to *B.t.*, and this foreign DNA is flanked, or segregated, by the duplicate copies of the internal resolution sites. The foreign DNA is excised from the plasmid shuttle vector by the site-specific recombination event between the two internal resolution sites, but this nonnative DNA can serve many useful purposes prior to the recombination event. Examples of such useful foreign DNA are selectable and/or screenable marker genes, such as antibiotic resistance genes functional in *B.t.* or *E. coli* or other cloning hosts; origins of replication functional in *E. coli*; and origins of replication functional in gram-positive microorganisms other than *B.t.*, e.g., in Bacillus species. Other DNA elements not native to *B.t.* may also be useful in the construction, development and characterization of insecticidal recombinant *B.t.* constructs, and these are also within the scope of the term "DNA not native to *B.t.*", as used herein. The term "DNA not native to *B.t.*", as used herein, is not intended to cover short polynucleotide stretches that are derived from multiple cloning sites or that are other synthesized, non-biological DNA.

The choice of the insecticidal protein toxin gene that is optionally and preferably present in the plasmid shuttle vector is not critical. The insecticidal protein toxin gene is normally selected to enhance the insecticidal characteristics of the *B.t.* host strain transformed with the plasmid shuttle vector. The insecticidal toxin gene is preferably selected from among wild-type or recombinant *B.t.* toxin genes. Exemplary *B.t.* toxin genes are those described by Höfte and Whiteley, 1989, as well as more recently reported *B.t.* genes such as cryIF, cryIIIB2 and cryIIIB3.

Bacteria transformed with the plasmid shuttle vector and capable of expressing at least one of the genes in the plasmid shuttle vector are also within the scope of this invention and are desirably selected from the group consisting of *Bacillus thuringiensis* and *E. coli*. One such recombinant *Bacillus thuringiensis* strain is *B.t.* strain EG7684 which contains plasmid shuttle vector pEG928.9.

It should be evident that the site-specific recombination system of this invention is not strictly limited to *B.t.* but is equally applicable to the construction of other Bacillus species recombinant constructs, if suitable changes are made in the plasmid shuttle vector, e.g., selection of an origin of replication functional in the selected Bacillus host species, DNA not native to the selected host species and optional insecticidal protein toxin genes capable of being expressed by the selected replicon.

Figure 5:
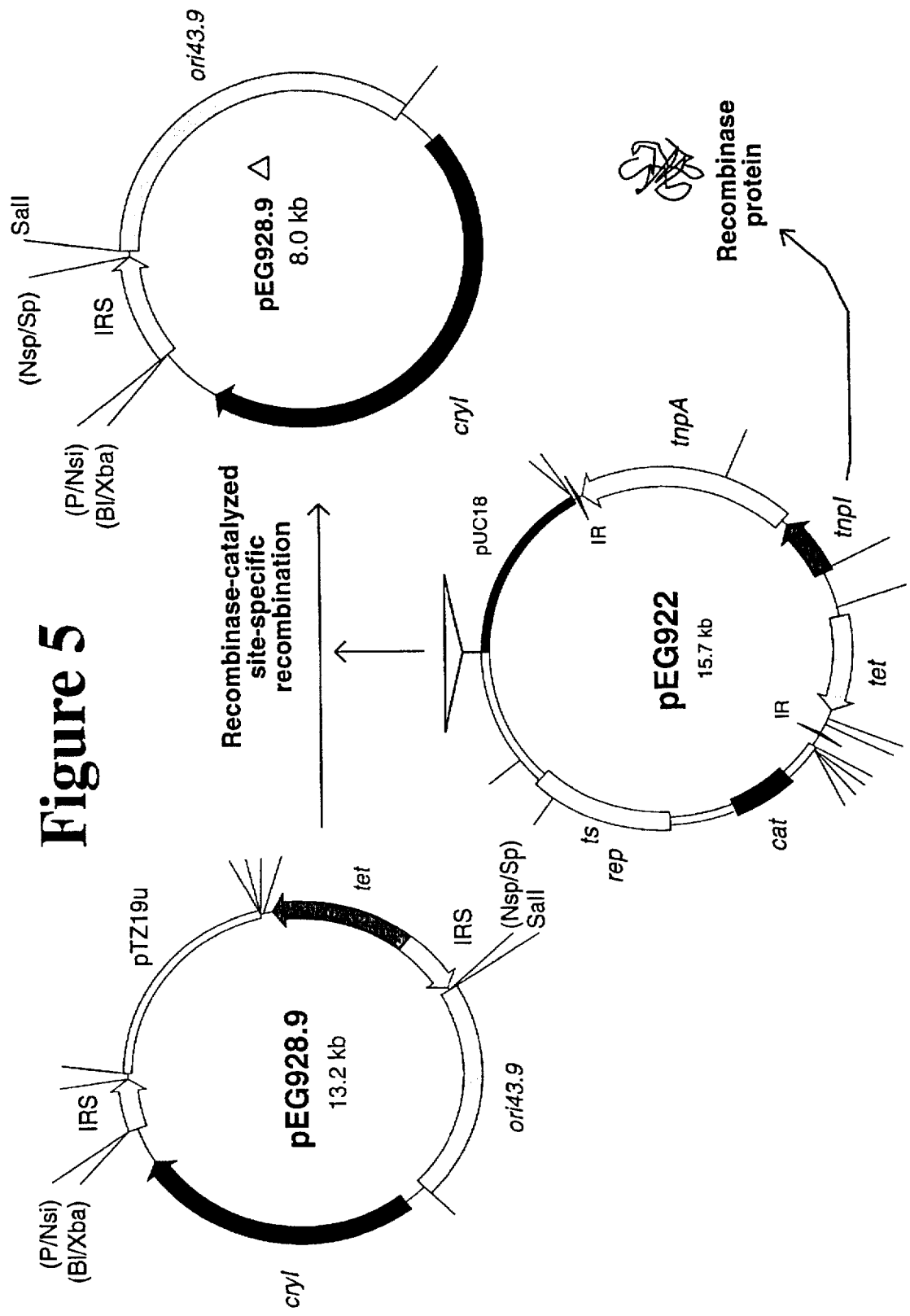
FIG. 5 is a schematic illustration of a method in which the plasmid shuttle vector of this invention, pEG928.9, is manipulated to excise its DNA elements which are not native to *B.t.* Removal of the foreign DNA elements, which are bracketed by duplicate IRS sites of transposon Tn5401, is accomplished by catalysis with a Tn5401 transposon-encoded resolvase/recombinase protein. Plasmid pEG928.9, shown and described in more detail in FIG. 4, contains DNA not native to *B.t.*, i.e., the *E. coli* replicon pTZ19u and a tetracycline antibiotic resistance gene, tet. This foreign DNA is flanked on either side by copies of an internal resolution site, IRS, from transposon Tn5401, oriented in the same direction. Plasmid pEG922, shown and described in more detail in FIG. 3, contains transposon Tn5401, whose resolvase gene, tnpI, is capable of expressing the resolvase/recombinase protein at temperatures below 37° C. in this temperature-sensitive plasmid. Sequential transformation of a host *B.t.* strain (not shown in the Figure) with both plasmid pEG928.9 and plasmid pEG922 and incubation of the transformed host *B.t.* strain at a temperature of 30° C. cause expression of the tnpI gene and production of resolvase/recombinase protein, which catalyzes a site-specific recombination event as shown in FIG. 5. The resultant plasmid pEG928.9Δ, an 8.0 kb derivative of pEG928.9 from which non-*B.t.* DNA elements have been excised via the site-specific recombination event, contains a *B.t.*-derived origin of replication, ori43.9, a cryI *B.t.* protein toxin gene, and a single copy of the internal resolution site, IRS, of transposon Tn5401. Abbreviations for the restriction endonuclease cleavage sites shown in this Figure are summarized in the descriptions of FIGS. 3 and 4.

The site-specific recombination system of this invention is schematically exemplified in FIG. 5, which illustrates plasmid shuttle vector pEG928.9 undergoing a site-specific recombination event catalyzed with recombinase/resolvase protein produced by the tnpI gene of the Tn5401-containing plasmid pEG922. The resultant plasmid pEG928.9Δ contains a single copy of the IRS, lacks DNA not native to *B.t.*, and contains a *B.t.*-derived replicon and a *B.t.* cryI-type protein toxin gene. The method of this invention as exemplified in FIG. 5 is described in detail in Example 5.

A preferred method of this invention, for constructing a recombinant *B.t.* strain containing no DNA elements foreign to *B.t.*, involves (a) transforming a host *B.t.* strain with a plasmid shuttle vector containing (i) an origin of replication native to *B.t.*; (ii) DNA not native to *B.t.* and useful in the construction of recombinant *B.t.* strains, selected from the group consisting of selectable marker genes, origins of replication functional in *E. coli*, and origins of replication functional in Bacillus host species other than *B.t.*; (iii) one or more insecticidal *B.t.* protein toxin genes; and (iv) two identical internal resolution sites oriented in the same direction and flanking the DNA not native to *B.t.*, the sites being the same as an internal resolution site from a Tn3-type transposon native to *B.t.*; (b) introducing into the transformed *B.t.* strain a resolvase protein to effect a site-specific recombination event involving the internal resolution sites, thereby excising from the plasmid shuttle vector the DNA not native to *B.t.*; and (c) recovering a recombinant *B.t.* strain containing a recombinant plasmid capable of replicating in the *B.t.* strain and containing (i) an origin of replication native to *B.t.*; (ii) one or more insecticidal protein toxin genes; and (iii) a single internal resolution site, derived from the site-specific recombination event.

In this method, the resolvase/recombinase protein should correspond to that produced by the resolvase/recombinase gene in the Tn3-type transposon used as the IRS source. The only requirement is that the resolvase/recombinase protein recognize the particular IRS site utilized.

The elements of the recombinant plasmid present in the recovered recombinant *B.t.* strain correspond, of course, to the same elements in the plasmid shuttle vector originally introduced into the host *B.t.* strain. Selection of the elements of the plasmid shuttle vector used in this method is governed by the same considerations discussed earlier for the plasmid shuttle vector of this invention.

Preferred Tn3-type transposon sources for the duplicate IRS sites in the plasmid shuttle vector are Tn4430 and Tn5401.

Introduction of the resolvase protein into the *B.t.* transformant containing the plasmid shuttle vector serves to effect a site-specific recombination event between the IRS sites in the vector. This introduction of the protein catalyzing agent may be accomplished by transforming the *B.t.* transformant with a second recombinant plasmid containing a resolvase gene and capable of expressing the resolvase protein. To facilitate efficient removal of the resolvase gene containing plasmid from the *B.t.* host strain following site-specific recombination, this plasmid desirably contains a temperature-sensitive replicon or other means for effecting its deletion and an antibiotic selectable marker gene different from the selectable marker gene carried on the plasmid shuttle vector. This approach is utilized in the site-specific recombination method described in Example 5.

Alternative means exist for introducing the recombinase protein into the transformed B.t. host strain containing the plasmid shuttle vector. One technique involves the direct introduction of the protein into the transformed B.t. cells, via the transient introduction of the recombinase protein via electroporation, lipofection or the like.

A second approach involves insertion of the recombinase gene into the plasmid shuttle vector within the non-B.t. DNA region flanked by the IRS sites. For IRS sites the same as that of transposon Tn5401, a mutant of the corresponding resolvase gene, tnpI, should produce a recombinase protein that is thermosensitive, being inactive at ~-37° C. but active at ~30° C. This tnpI$^{ts}$ variant could be obtained by a variety of well-known in vitro mutagenesis procedures, including chemical mutagenesis of the tnpI gene, followed by selection for tnpI variants that catalyze recombination at 30° C. but not at 37° C. Transformation of a suitable B.t. host strain with a tnpI$^{ts}$-containing plasmid shuttle vector at a temperature of 37° C. will prevent expression of the tnpI gene, but this will allow for selection of transformants containing the plasmid shuttle vector.

Subsequently, the B.t. transformants are grown at a temperature of 30° C., resulting in expression of a functional recombinase protein and excision of the foreign DNA elements, as well as excision of the tnpI$^{ts}$ gene, since both are contained within the non-B.t. DNA region flanked by the IRS sites.

Both of these alternative procedures for introducing the recombinase protein to effect site-specific recombination avoid the need to introduce a second recombinant plasmid, i.e., one containing an expressible recombinase gene, into the transformed B.t. strain and avoid the need to thereafter delete the same second recombinant plasmid following the recombination event.

The site-specific recombination system of this invention yields recombinant toxin plasmids that possess a unique combination of elements. The recombinant plasmids, capable of replicating in B.t. bacteria, contain at least one insecticidal protein toxin gene, an origin of replication functional in B.t., and a single internal resolution site (or other single site-specific recombination site).

In a preferred embodiment, the single internal resolution site of the recombinant plasmid is derived from a Tn3-type transposon or is identical to the IRS in such a transposon. The Tn3-type transposon IRS source is desirably one that is native to B.t. The internal resolution site is preferably identical to the IRS of transposon Tn4430 or, more preferably, transposon Tn5401.

The origin of replication in these recombinant toxin plasmids is preferably native to B.t. The B.t.-functional origin of replication is preferably derived from, or identical to, a replicon of a large B.t. plasmid, for the same reasons discussed previously for the plasmid shuttle vector of this invention.

The bacteria containing these recombinant toxin plasmids are preferably Bacillus thuringiensis but other bacterial hosts can be used, provided that the replicon in the plasmid is capable of functioning in such a non-B.t. host.

Particularly preferred recombinant B.t. constructs containing the recombinant plasmids of this invention are described in Example 5. It should be evident from the discussion in Example 5 that this invention provides the means to construct a wide variety of insecticidal recombinant B.t. strains containing no DNA elements not native to B.t. The site-specific recombination system of this invention facilitates construction of insecticidal recombinant B.t. strains with good stability characteristics, exhibiting limited horizontal transfer of their recombinant plasmids. The invention also permits the rapid construction and evaluation of recombinant B.t. constructs with unique complements of B.t. toxin genes that previously could not be quickly and easily realized with the prior art techniques.

The basic methods employed in the construction and evaluation of the recombinant plasmids described in this specification are generally well-known to those proficient in the art of molecular cloning. Descriptions of these general laboratory procedures and definitions of nomenclature may be found in Maniatus et al., *Molecular Cloning, A Laboratory Manual*, Cold Spring Harbor Laboratory, Cold Spring Harbor, N.Y. (1982) and in a subsequent edition by Sambrook et al. (1989).

The following Examples provide further explanation of the invention and methods of its use.

EXAMPLE 1

Isolation and DNA Sequence Analysis of Tn5401

The transposon Tn5401 of this invention was initially isolated from copies of a recombinant plasmid which had been introduced into B.t. var. *morrisoni* strain EG2158 by electroporation. Transposon Tn5401 was subsequently shown to be located on two resident plasmids (35 and 72 MDa in size) of B.t. strain EG2158 from which it had apparently "jumped", or transposed itself, into the recombinant plasmids.

Figure 6:
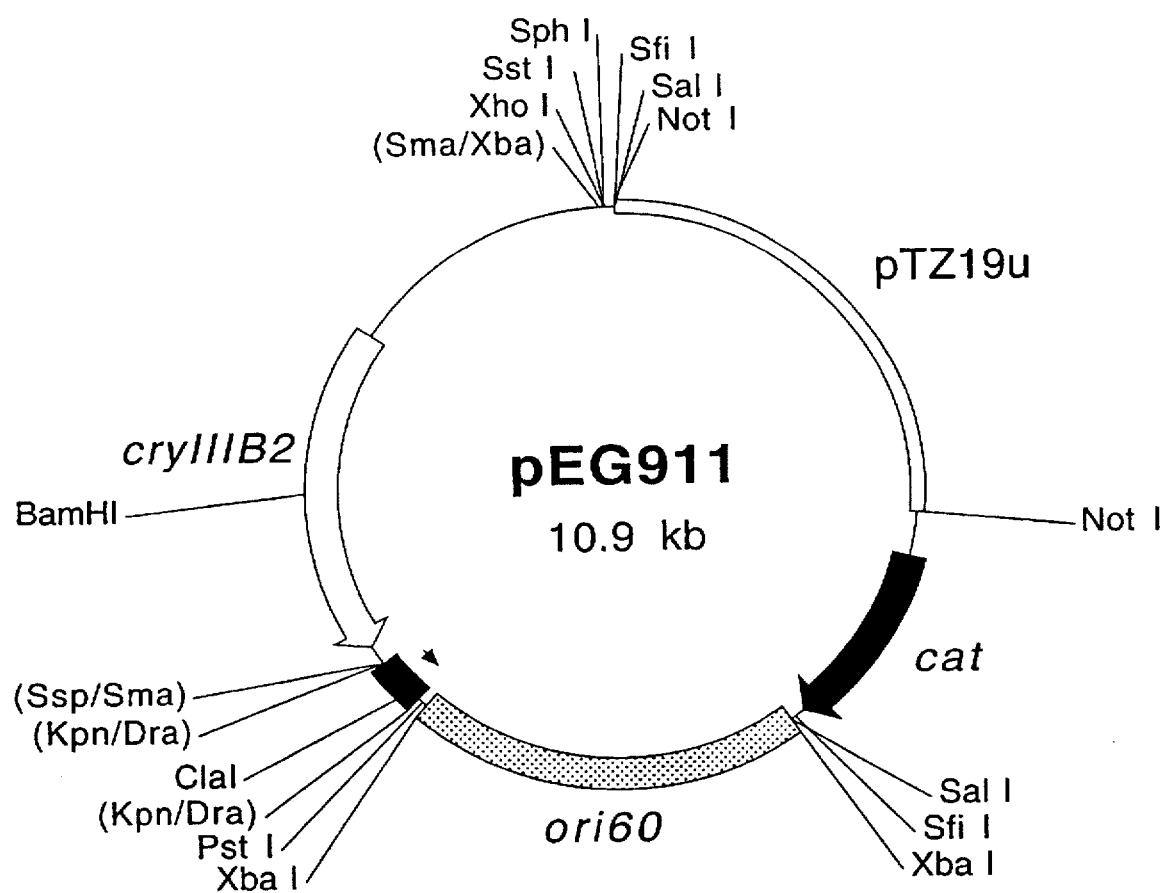
FIG. 6 is a circular structural map of plasmid pEG911, from which transposon Tn5401 was isolated after recovery of the Tn5401-containing pEG911 derivative from *B.t.* var. *morrisoni* strain EG2158. Plasmid pEG911, approximately 10.9 kb in size, contains the following elements. The open arrow indicates the cryIIIB2 *B.t.* protein toxin gene; the open segment indicates the *E. coli* replicon pTZ19u; the solid arrow indicates the chloramphenicol acetyl transferase gene, cat, from plasmid pC194; the shaded segment indicates the ori60 *B.t.* plasmid origin of replication region; and the solid box segment with accompanying arrowhead indicates a *B.t.* gene transcription terminator. Abbreviations are used for some restriction endonuclease cleavage sites shown in the Figure and these are as follows: Dra=DraI, Kpn=KpnI, Sma=SmaI, Ssp=SspI, Xba=XbaI.

The recombinant plasmid pEG911, shown in FIG. 6, was used as the donor plasmid in transformation studies with B.t. strain EG2158, employing the conventional electroporation protocol described by Mettus et al., *Applied and Environ. Microbiol.* 56:1128–1134 (1990). Restriction enzyme analysis of DNA from recombinant plasmids isolated from several B.t. strain EG2158 transformants indicated that a subpopulation of the pEG911 plasmids contained a common ~5 kilobase (kb) DNA insert.

Figure 7:
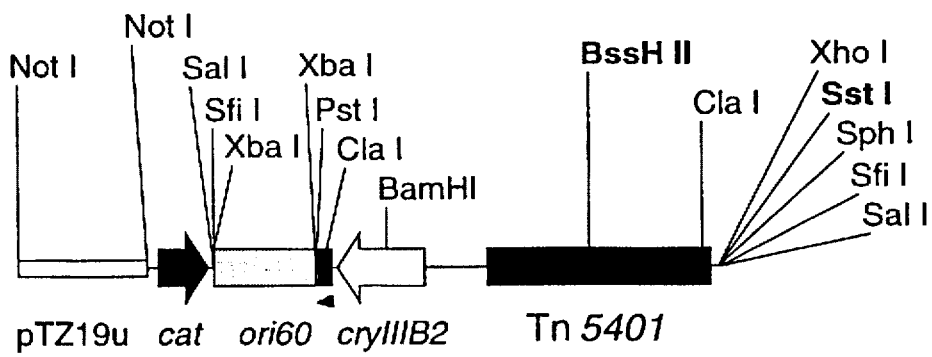
FIG. 7 shows linear structural maps for plasmids pEG911-1 and pEG911-3, both of which are derivatives of plasmid pEG911 (see FIG. 6) and both of which contain an insertion of transposon Tn5401 from *B.t.* var. *morrisoni* strain EG2158. The long solid black segment in both of these structural maps indicates the transposon Tn5401. As indicated by the location of the ClaI and BssHII sites within Tn5401, pEG911-1 and pEG911-3 contain Tn5401 in opposite orientations. Identification of the various elements within plasmids pEG911-1 and pEG911-3 and the abbreviations for restriction sites are as described for FIG. 6.
Figure 7:
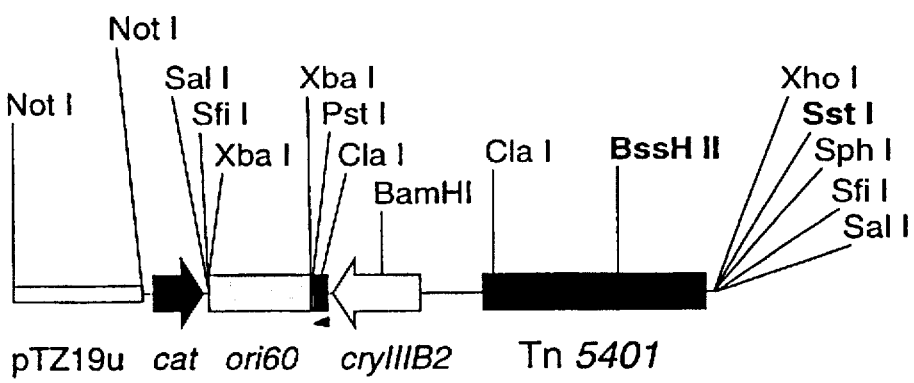

Recombinant plasmid DNAs from two different, independent B.t. strain EG2158 transformants, each containing the 5 kb DNA insert, were recovered in *Escherichia coli* by selecting for *E. coli* transformants resistant to 50 µg/ml ampicillin. Linear restriction maps of two independent plasmid clones, designated pEG911-1 and pEG911-3, are shown in FIG. 7. Each of these plasmids contains a ~5 kb insertion (shown as a solid black box and designated Tn5401) upstream of the cryIIIB2 B.t. protein toxin gene (shown as a white arrow) but in opposite orientations as indicated by the placement of the unique BssHII and ClaI restriction endonuclease cleavage sites.

Plasmid pEG911-1 was chosen as the template for DNA sequence analysis of the ~5 kb DNA insert. Double-stranded DNA was sequenced according to the well-known dideoxy chain termination method using [alpha-$^{35}$S]DATP. Synthetic oligonucleotides were generated to serve as primers for DNA sequence analysis. Sequence analysis was initiated using primers complementary to DNA flanking the DNA insert. Subsequently, sequencing primers were synthesized as needed based on the derived DNA sequences.

The complete nucleotide sequence of the ~5 kb insert of plasmid pEG911-1 is shown in FIG. 1 and has been identified as a transposable element based on an analysis of its characteristics. This transposable element, having a size of 4837 basepairs, has been designated as transposon Tn5401.

For microorganism deposit purposes, plasmid pEG911-1, containing transposon Tn5401 on the ~5 kb insert, was introduced into an *E. coli* host strain, *E. coli* JM110, to yield *E. coli* strain EG7683.

A linear structural map of Tn5401 is shown in FIG. 2, which includes the location of open reading frames denoted by arrows: orf1 (open arrow) potentially encodes a cryptic protein of unknown significance, of 85 amino acids in the 3'-5' direction; tnpI (dark shaded arrow) encodes a protein in the 5'-3' direction which has been designated the resolvase protein of Tn5401 and which contains 306 amino acids; and tnpA (light shaded arrow) encodes a protein in the 5'-3' direction which has been designated the transposase protein of Tn5401 and which contains 1005 amino acids. Not shown on FIG. 2 is a second open reading frame, orf2, which, like orf1, is oriented in the 3'-5' direction and potentially encodes a small cryptic protein which is of unknown significance and which contains 74 amino acids. Although not shown in FIG. 1, this deduced second small cryptic protein is derived from the complementary nucleotide sequence extending from nucleotide base positions 122 to 343.

Another distinguishing characteristic of Tn5401 shown in FIG. 2 is the location of its internal resolution site, located within the bracketed DNA fragment designated as "IRS region" and is likely located near the promoter region for the tnpI gene. Yet another characteristic of Tn5401 is the inverted repeats of 53 basepairs at either end of the transposon, shown as black arrowheads at both ends of the structural map in FIG. 2.

Analysis of Tn5401 and its elements was carried out using available computer databases to determine homologies with other DNA in the databases. These analyses indicate that Tn5401 belongs in the Tn3 family of transposons and, based on comparisons of its resolvase and transposase proteins, is related to Tn4430, the prior art transposon which is also present in *B.t.* species.

The 36 kDa resolvase protein of Tn5401 shows 25% amino acid sequence identity to the resolvase/recombinase protein of the Tn4430, but no significant identity to the corresponding resolvase protein of Tn3.

The 116 kDa transposase protein of Tn5401 shows 29% amino acid sequence identity to the transposase protein of Tn4430 and 44% identity to the transposase protein of Tn3.

The respective sequences of the 10.1 kDa cryptic protein of orf1 and of the 8.6 kDa cryptic protein of orf2 in Tn5401 showed no apparent homology to sequences in the databases.

EXAMPLE 2

Construction of Transposon Vector PEG922 Containing Tn5401

Figure 8A:
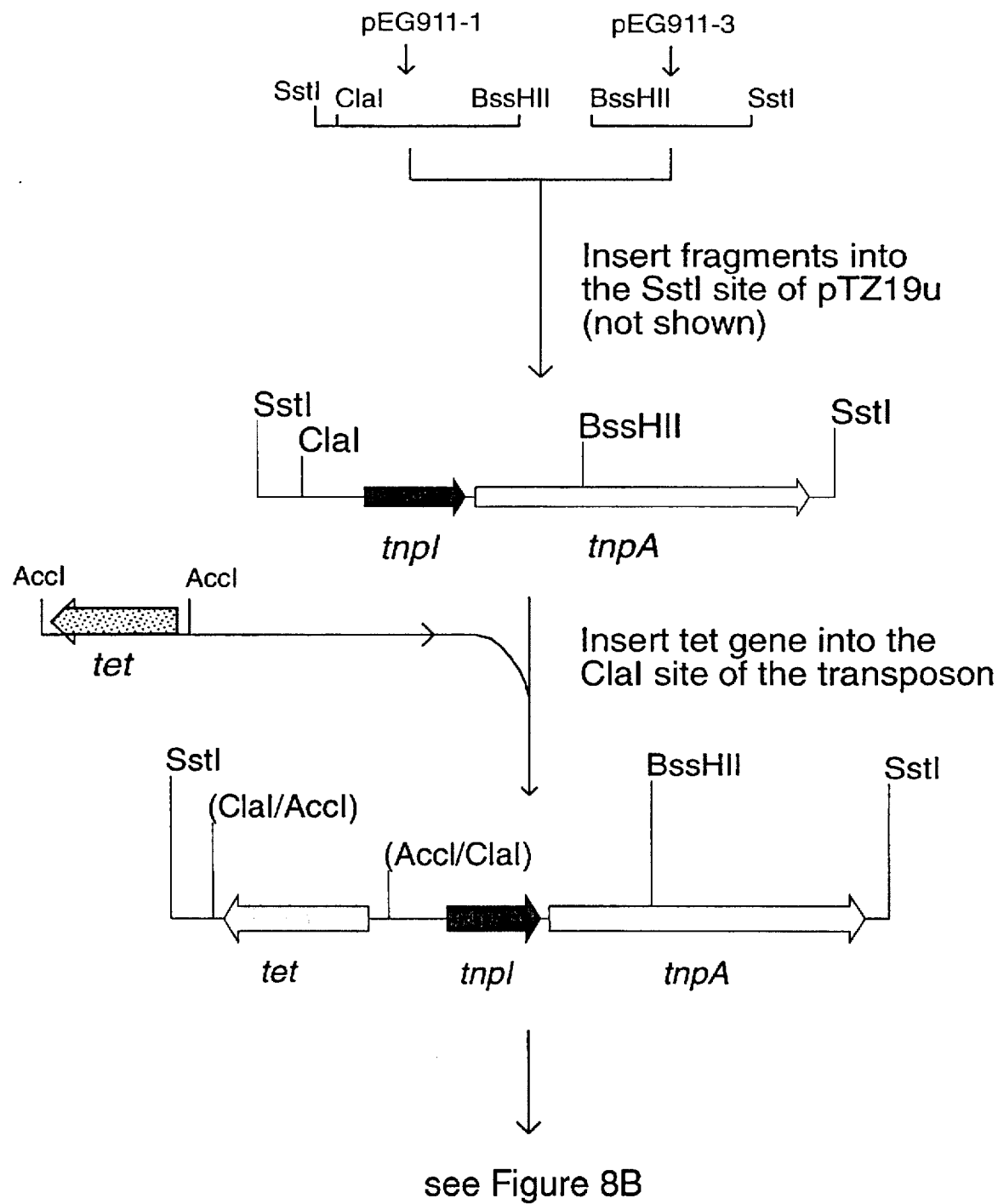
FIG. 8A–B consists of FIGS. 8A and 8B and is a schematic diagram showing the recombinant DNA procedures used to derive plasmid pEG922, which is also shown in FIG. 3 and is utilized in the method of FIG. 5. Plasmid pEG922 contains the isolated transposon Tn5401 of this invention. Details of the steps shown in this Figure for the derivation of plasmid pEG922 are explained in Example 2. Abbreviations are used for some of the restriction endonuclease cleavage sites shown in FIG. 8 and these are as described for FIG. 3, which also provides a description of the circular structural map of plasmid pEG922.
Figure 8B:
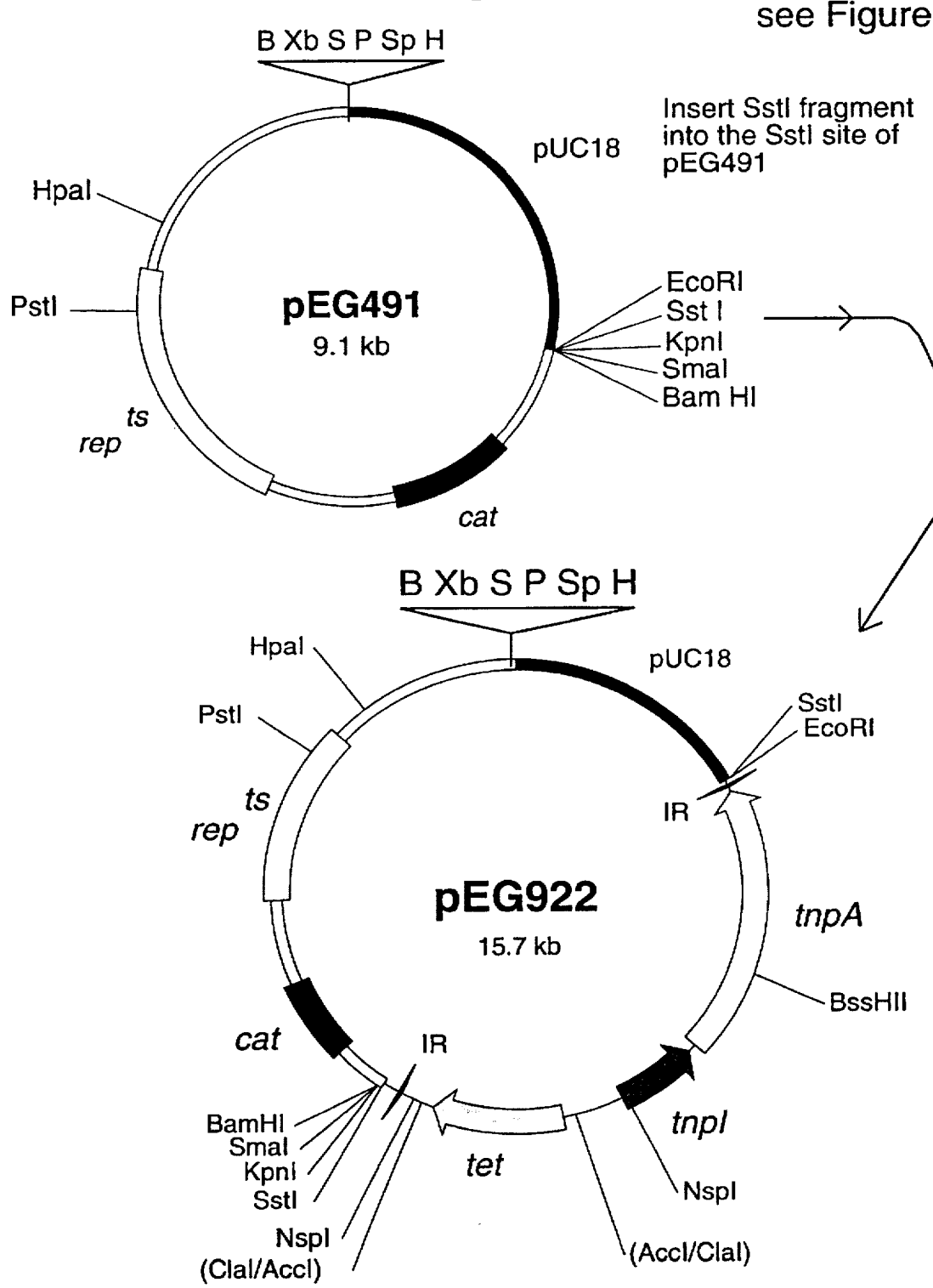
Figure 9A:
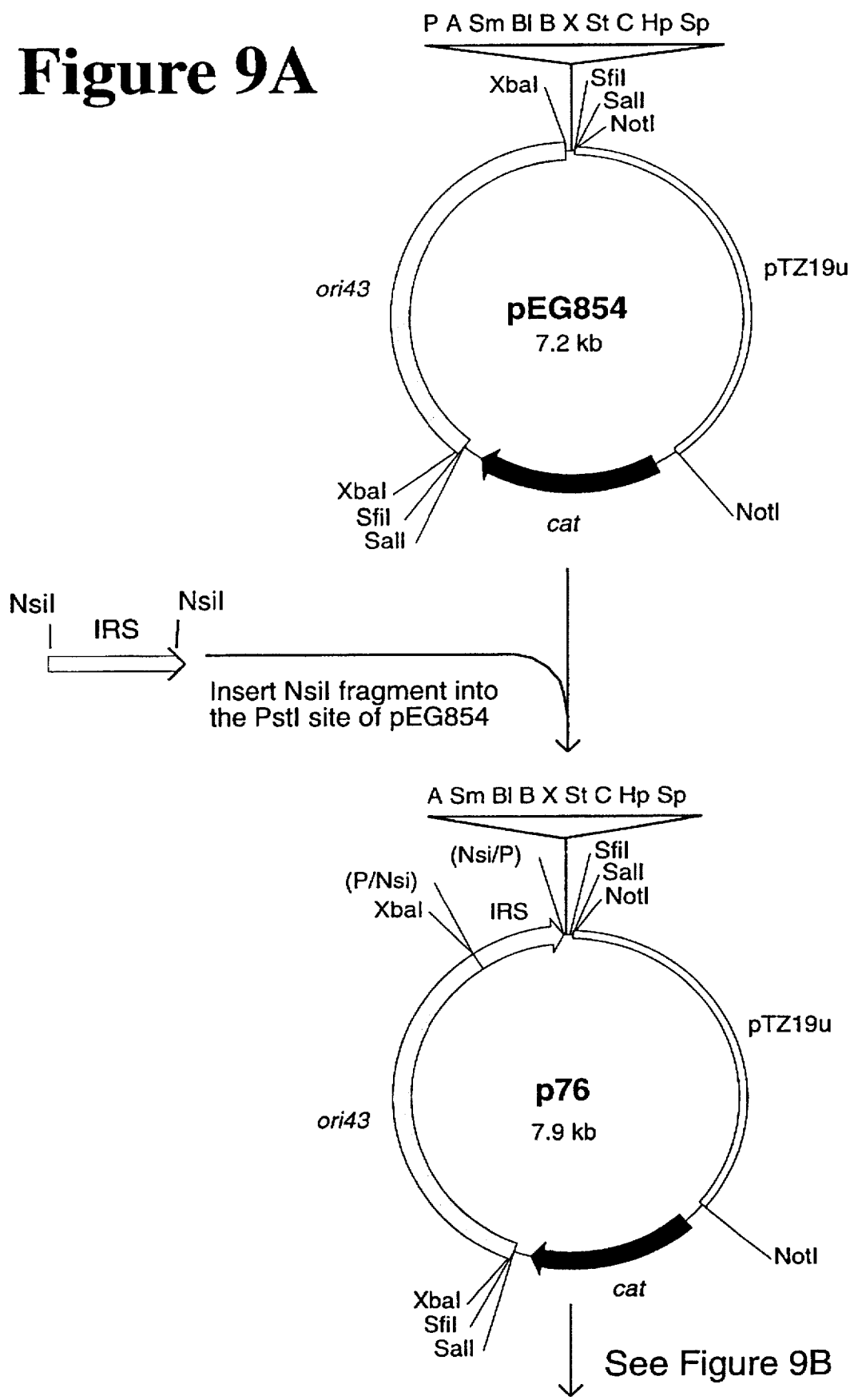
FIG. 9 consists of FIGS. 9A, 9B, 9C, 9D and 9E and is a schematic diagram showing the recombinant DNA procedures used to derive the plasmid shuttle vector pEG928.9 of this invention, which is also shown in FIG. 4 and is utilized in the method of FIG. 5. Details of the steps shown in this Figure for the derivation of plasmid shuttle vector pEG928.9 are explained in Example 3. Abbreviations are used for some of the restriction endonuclease cleavage sites shown in FIG. 9 and these are as follows. For the multiple cloning site in plasmid shuttle vector pEG854 and its derivatives, plasmid clones p76 and p83: P=PstI, A=Asp718, Sm=SmaI, Bl=BlnI, B=BamHI, X=XbaI, St=SstI, C=ClaI, Hp=HpaI, Sp=SphI. For the multiple cloning site in pTZ19u and its derivative, plasmid clone p84: E=EcoRI, St=SstI, A=Asp718, Sm=SmaI, B=BamHI, Xb=XbaI, S=SalI, P=PstI, Sp=SphI, H=HindIII. Other abbreviations for restriction sites shown on plasmid shuttle vector pEG928.9 and its precursor plasmid clones are as described for FIG. 4, which also provides a description of the circular structural map of pEG928.9.
Figure 9B:
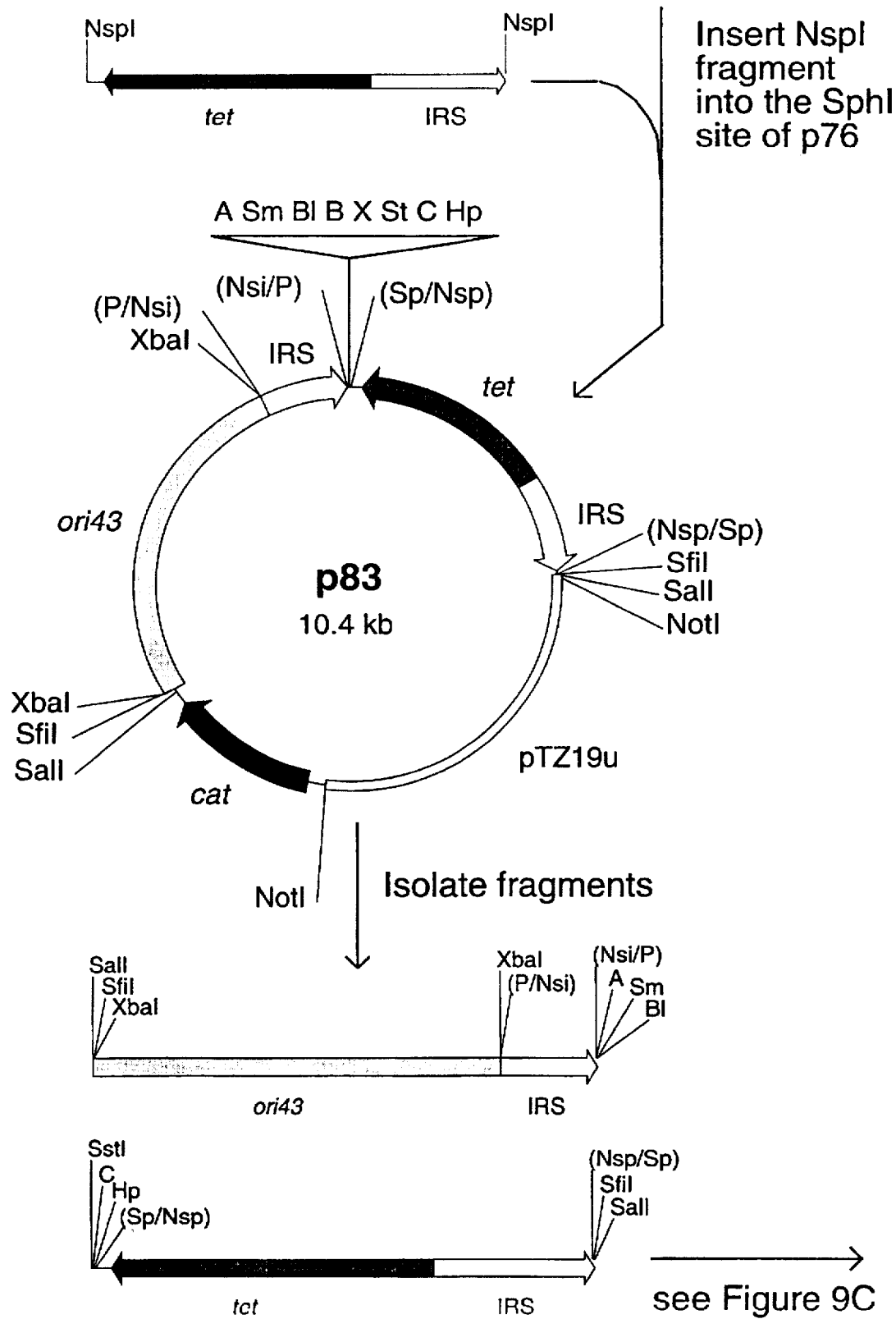
Figure 9C:
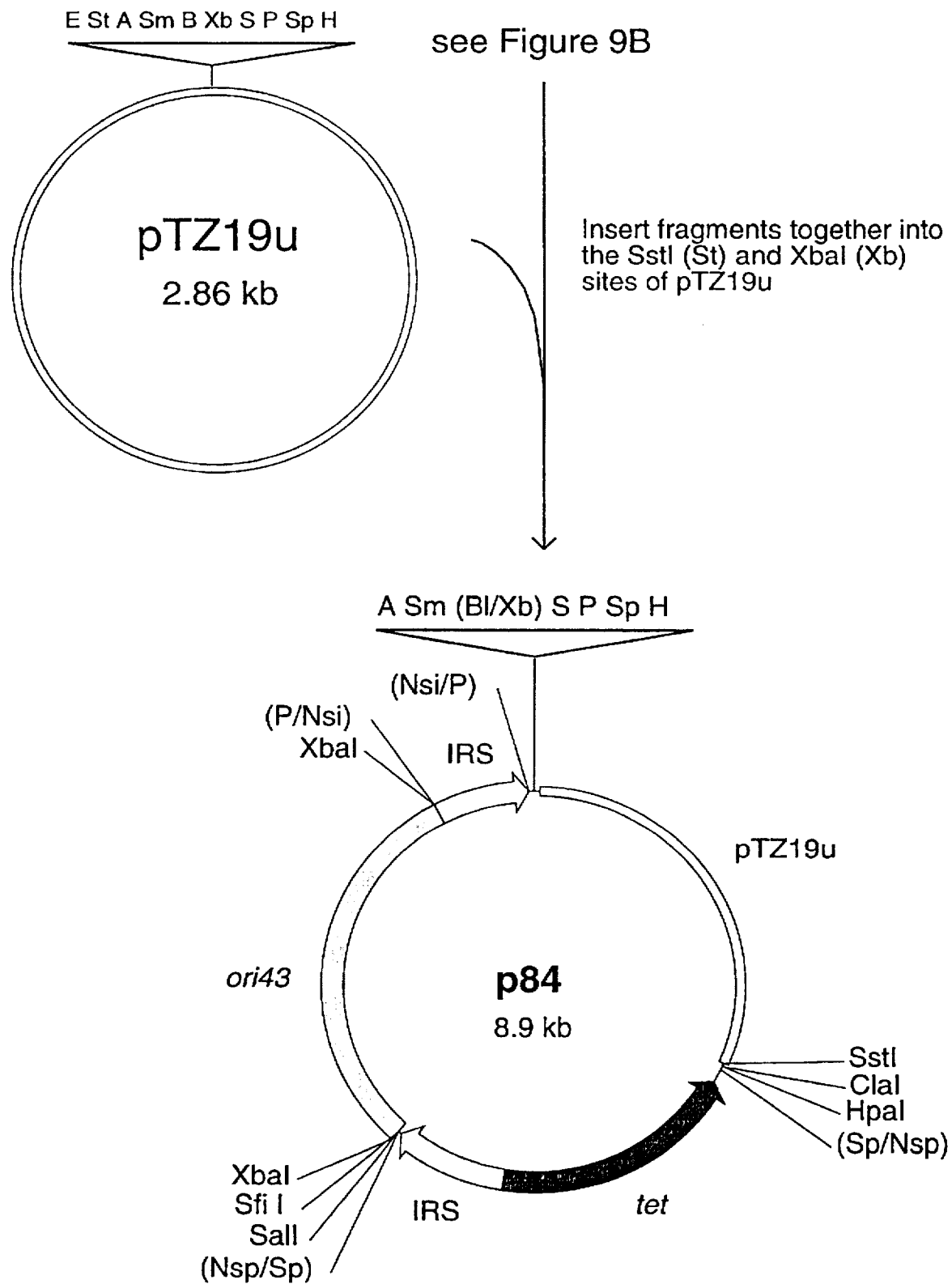
Figure 9D:
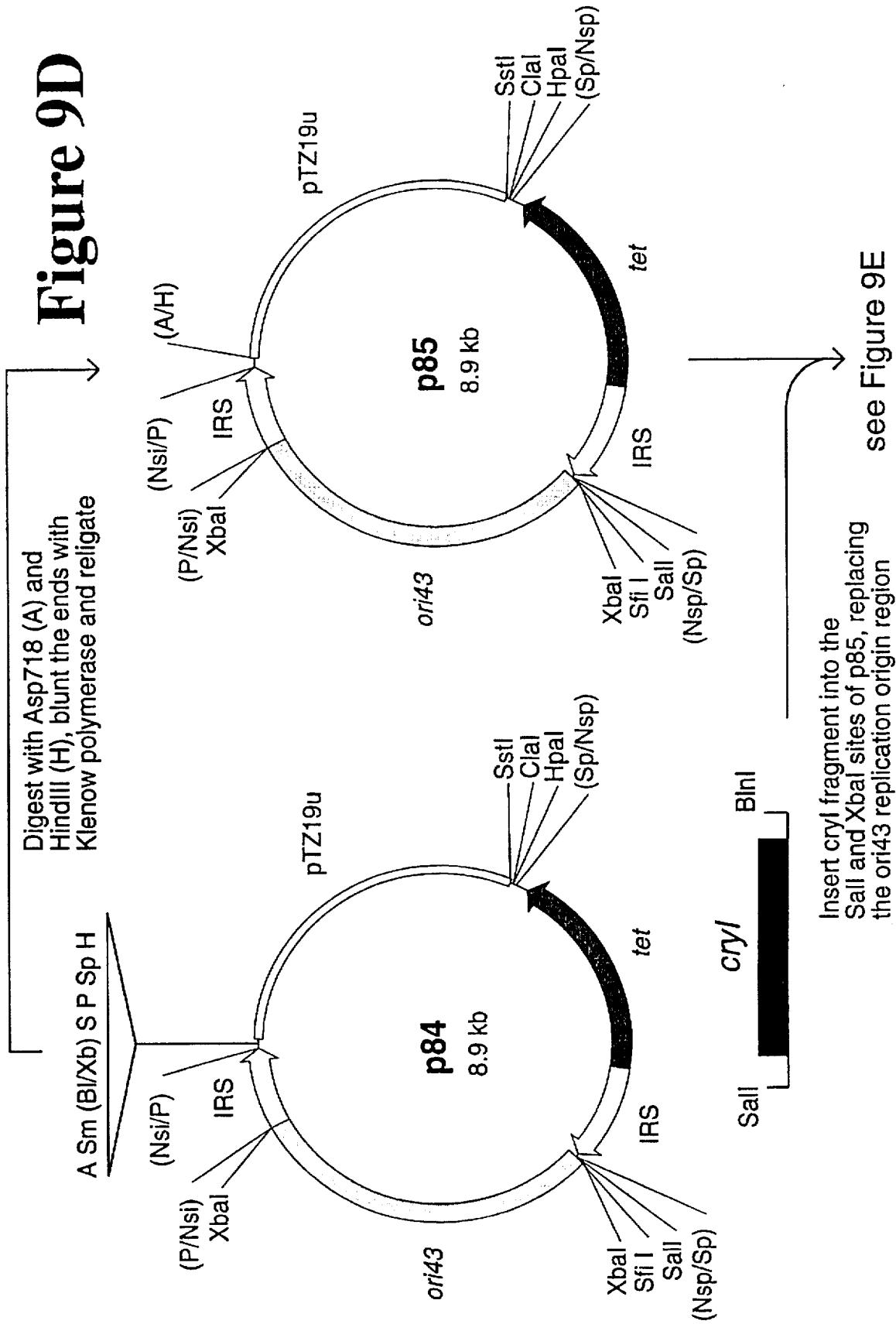
Figure 9E:
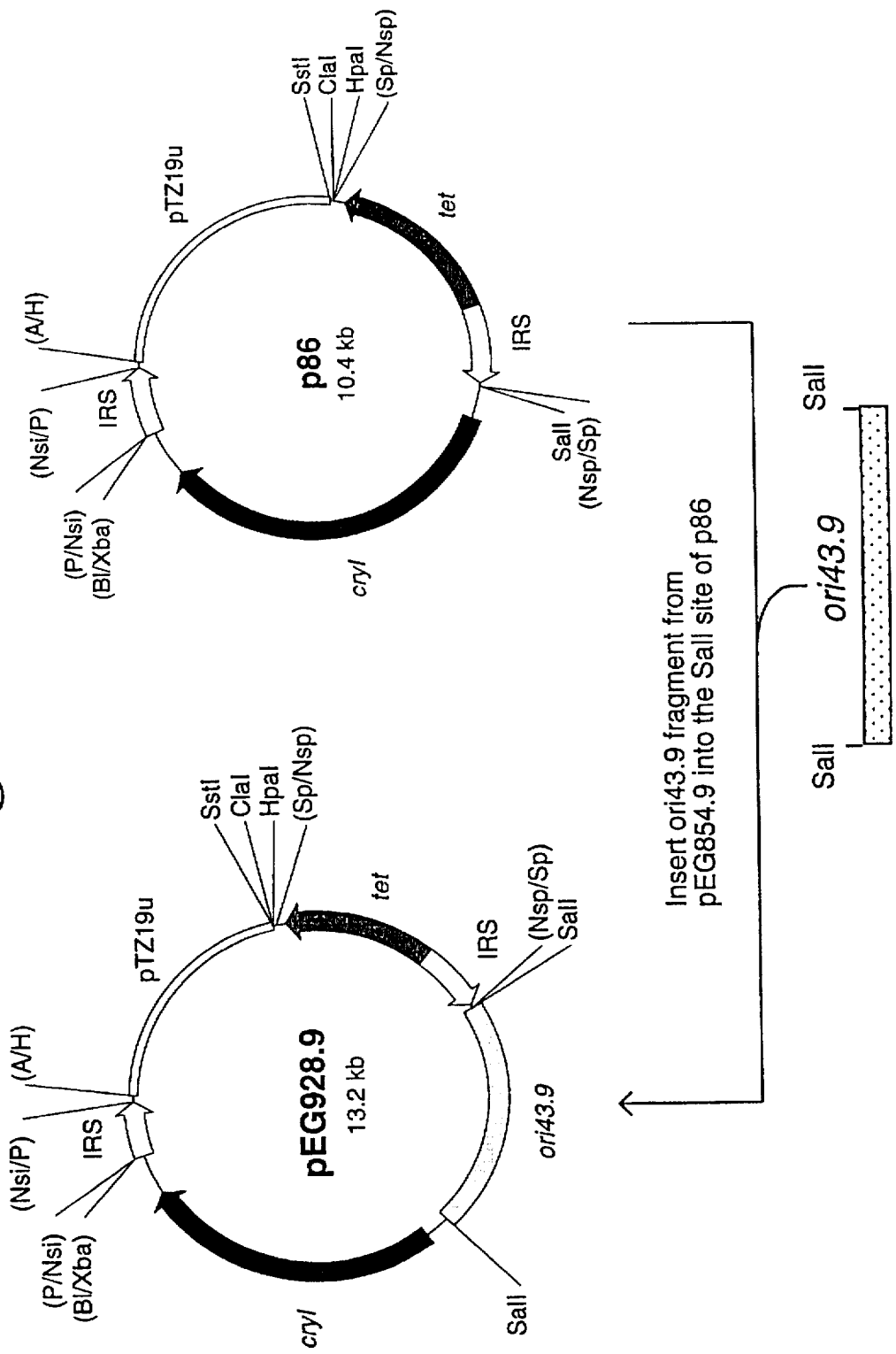

The ability of the isolated transposon Tn5401 to transpose in a *B.t.* strain is shown in this Example. As described in more detail below and as shown in FIG. 8, the cloned transposon Tn5401 was tagged with an antibiotic resistance marker gene, then inserted into a temperature-sensitive recombinant shuttle vector functional in *B.t.* The resultant Tn5401-containing shuttle vector, designated pEG922 and a circular structural map of which is shown in FIG. 3, was used to transform a plasmid-free *B.t.* strain, and measurements of its transposition efficiency were obtained.

The recombinant DNA manipulations involved in the construction of pEG922 were carried out using conventional techniques, familiar to those skilled in the art of cloning DNA, and are shown in schematic form in FIG. 8.

A ~3 kb BssHII-SstI DNA fragment from plasmid pEG911-1, shown in FIG. 7 and containing a portion of Tn5401, and a ~2.3 kb BssHII-SstI DNA fragment from pEG911-3, also shown in FIG. 7 and containing the remaining portion of Tn5401, were cloned together as shown in FIG. 8A into the SstI site of the well-known *E. coli* cloning vector pTZ19u. The resulting cloned DNA fragment contained a reconstructed, complete Tn5401 transposon with flanking SstI sites as shown in FIG. 8A.

The Tn5401 transposon in this cloning vector was next tagged with a tetracycline antibiotic resistance marker gene (tet) from the well-known *Bacillus cereus* plasmid pBC16, contained on a ~1.7 kb AccI-AccI DNA fragment, by insertion of this fragment into the unique ClaI site on transposon Tn5401, whose structural map is shown in FIG. 2. It should be noted that an AccI cleavage site is compatible with a ClaI site. The tagged transposon Tn5401 was subsequently recovered on a ~7 kb SstI fragment, as shown in FIG. 8A.

As shown in FIG. 8B, the tet-tagged transposon Tn5401 on the SstI fragment was inserted into the unique SstI site of a temperature-sensitive shuttle vector, pEG491, whose circular structural map is shown in FIG. 8B. Plasmid pEG491 is a shuttle vector derived in part from the well-known cloning vector pUC18, which also contains a chloramphenicol acetyl transferase antibiotic resistance gene (cat) and a temperature-sensitive replicon ($rep^{ts}$) functional in gram-positive bacteria, the latter element being derived from plasmid pE194ts. The temperature-sensitive replicon $rep^{ts}$ cannot operate at temperatures at or above 37° C, in contrast to most *B.t.*-derived replicons which operate at higher temperatures.

Plasmid pE194ts is described by Villafane et al. in *J. Bacteriol.* 169:4822–4829 (1987), and its use with a transposon (Tn917) is described by Youngman et al. at p. 101–102 in Plasmids: a practical approach, Hardy, ed., IRL Press, Oxford, England (1987) pp. 79–103.

The resulting transposon vector, designated pEG922, contains the tet-tagged transposon Tn5401 on a ~7 kb fragment inserted into the SstI site of plasmid pEG491, as shown in FIG. 8B which contains a circular structural map of plasmid pEG922. Plasmid pEG491, as shown in FIG. 8B, contains the *E. coli* replicon pUC18 (thin black segment), a chloramphenicol acetyl transverse gene, cat (thick black segment), and a temperature-sensitive replicon, $rep^{ts}$, from plasmid pE194ts which cannot operate at temperatures at or above 37° C. At the top of plasmid pEG491 is a multiple cloning site. Abbreviations for the restriction endonuclease cleavage sites in the multiple cloning site are explained in the discussion of FIG. 3 (which also shows the structural map of pEG922) appearing in the Brief Description of the Drawings.

For microorganism deposit purposes, plasmid pEG922 was also used to transform a host strain, *E. coli* strain GM2163, to yield *E. coli* strain EG7669.

The recombinant shuttle plasmid pEG922 was introduced into a plasmid-free *B.t.* var. *kurstaki* strain EG7566 by electroporation following the procedures of Mettus et al. (1990). Transposition of Tn5401 within the resulting transformed *B.t.* strain was measured using the procedure described by Youngman in *Plasmids: a practical approach*, Hardy, ed., IRL Press, Oxford, England (1987) pp 79–103. Transposition frequencies were measured as the quotient of the number of tetracycline resistant colonies observed at a temperature of 41° C. divided by the number of chloramphenicol resistant colonies at a temperature of 30° C. Transposition frequencies of $10^{-3.1 - 4}$ were routinely obtained in transformed B.t. strain EG7566, indicating that transposon Tn5401 contained on plasmid pEG922 was functional in *B.t.*

Subsequent studies by the inventor with plasmid pEG922 in plasmid-containing *B.t.* strains have shown that transposon Tn5401 favors transposition into other plasmids, rather than into chromosomal DNA, and exhibits an apparent preference for AT-rich regions of DNA. Transposition frequencies observed for one plasmid-containing *B.t.* strain were generally two to three orders of magnitude higher than those obtained with the plasmid-free *B.t.* strain EG7566, typically being about $10^{-1}$–$10^{-2}$.

EXAMPLE 3

Construction of Plasmid Shuttle Vector pEG928.9

The plasmid shuttle vector pEG928.9 of this invention is useful for insecticidal recombinant *B.t.* strain development and is illustrated in FIG. 4. Example 3 describes the construction of plasmid shuttle vector pEG928.9, and the recombinant DNA procedures involved in this construction are schematically illustrated in FIG. 9.

The plasmid shuttle vector pEG854 was used as a starting point for the derivation of plasmid pEG928.9, as shown in FIG. 9A. Plasmid shuttle vector pEG854 is contained in *E. coli* strain EG7534, which is a deposited microorganism described in PCT International Patent Publication WO 91/18102.

Plasmid shuttle vector pEG854 contains a *B.t.* plasmid origin of replication, ori43 (light shaded segment), a multiple cloning site (shown at the top of the plasmid), the *E. coli* replicon pTZ19u, and a chloramphenicol acetyl transferase gene, cat (black arrow). The internal resolution site, IRS, of transposon Tn5401 (see FIG. 2) contained on a ~650 bp NsiI-NsiI fragment from plasmid pEG911-1 (see FIG. 7) was inserted into the unique PstI site in the multiple cloning site of pEG854 to yield the cloned plasmid p76.

A second copy of the IRS from transposon Tn5401, contained on a 2.5 kb NspI-NspI fragment from plasmid pEG922 (see FIG. 3), was inserted into the unique SphI site in the multiple cloning site of p76 to yield the cloned plasmid p83, as shown in FIG. 9B. Both IRS copies were in the same orientation (clockwise) in plasmid p83, as shown by the open arrows. The IRS copy in the NspI-NspI fragment also contained the tetracycline antibiotic resistance gene, tet (dark shaded arrow), that had been introduced into pEG922 (see FIGS. 3 and 8) as a selectable marker tag for transposon Tn5401.

As shown in FIG. 9B, plasmid p83 was digested with SalI, BlnI and SstI, and fragments containing the IRS sites were isolated: a 3.5 kb SalI-BlnI fragment containing the IRS and *B.t.* origin of replication ori43, and a 2.5 kb SstI-SalI fragment containing the IRS and the tet selectable marker gene. As shown in FIG. 9C, these two IRS-containing fragments were inserted together into the SstI and XbaI sites in the multiple cloning site of the well-known *E. coli* 2.86 kb phagemid vector pTZ19u to generate the cloned plasmid p84. The two copies of the IRS were in the same orientation, as shown in FIG. 9C, with the IRS sites segregating the *B.t.* origin of replication ori43 from the tet selectable marker gene and pTZ19u replicon.

The multiple cloning site in the 8.9 kb plasmid p84 was removed, as shown in FIG. 9D, by digesting with Asp718 and HindIII, blunting the protruding ends with Klenow polymerase and religating to generate the cloned plasmid p85. Plasmid p85, containing the *B.t.* origin of replication ori43, was manipulated to replace ori43 with a cryI-type *B.t.* protein toxin gene, specifically a cryIC-cryIAc fusion gene. The choice of the specific *B.t.* toxin gene for insertion into p85 is not critical; any insecticidal protein toxin gene could be utilized, e.g., a *B.t.* cryI, cryII, cryIII or cryIV toxin gene could be utilized.

Plasmid p85 was cleaved with SalI and XbaI and the vector fragment lacking ori43 was ligated to a SalI-BlnI fragment containing a cryI-type gene as shown in FIGS. 9D and 9E; note that a BlnI cleavage site is compatible with that of XbaI. The resultant plasmid clone was designated plasmid p86, shown in FIG. 9E.

Plasmid pEG928.9, the shuttle vector plasmid of this invention, was obtained from plasmid p86 by insertion of a *B.t.* plasmid origin of replication into p86, as shown in FIG. 9E. A 2.8 kb SalI fragment, containing *B.t.* plasmid origin of replication cri43.9, was inserted into the unique SalI site of p86 to yield pEG928.9. The ori43.9 *B.t.* origin of replication gene and the cryI-type protein toxin gene are transcribed in opposite directions. As shown in FIG. 9E, the duplicate copies of the Tn5401 internal resolution site segregate the DNA not native to *B.t.*, i.e., the *E. coli* replicon pTZ19u and the tet selectable marker gene from the *B.t.* origin of replication and adjacent cryI-type protein toxin gene.

For microorganism deposit purposes, plasmid shuttle vector pEG928.9 was used to transform an acrystalliferous *B.t.* host strain, *B.t.* var. *kurstaki* strain EG10368 which is a derivative of *B.t.* var. *kurstaki* strain HD73-26 described in U.S. Pat. No. 5,080,897 issued to González, Jr. et al. on Jan. 14, 1992, to yield *B.t.* var. *kurstaki* strain EG7684.

In an analogous manner, other plasmid shuttle vectors were also constructed. Use of plasmid shuttle vector pEG928.9, and other analogous shuttle vectors, in a site-specific recombination system for constructing insecticidal recombinant *B.t.* strains, is described in Example 5.

EXAMPLE 4

Site-Specific Recombination Catalyzed by Recombinase Protein from Tn5401

The ability of recombinase/resolvase protein from transposon Tn5401 to catalyze, in trans, a site-specific recombination event in a transformed recombinant *B.t.* strain was demonstrated in this Example 4. The recombinant plasmid used to transform the host *B.t.* strains was plasmid p83, described in Example 3 and a circular structural map of which is illustrated in FIG. 9B. Plasmid p83 contains two identical copies of the Tn5401-derived internal resolution site, IRS, oriented in the same direction and flanking a tetracycline antibiotic resistance gene, tet, as shown in FIG. 9B. Plasmid p83 also contains an origin of replication functional in *B.t.*, i.e., *B.t.*-derived ori43, and another selectable marker gene, a chloramphenicol acetyl transferase gene, cat, as shown in FIG. 9B.

A site-specific recombination event involving plasmid p83 was demonstrated by showing that the cat gene encoding resistance to chloramphenicol would be maintained after a site-specific recombination event between the two IRS regions but that tetracycline resistance would be lost because of excision of the tet gene during such recombination. The source of recombinase protein for catalyzing the site-specific recombination was *B.t.* var. *morrisoni* strain EG2158, which harbors transposon Tn5401 which contains the recombinase gene, tnpI.

Plasmid p83 was first introduced by a conventional electroporation technique into the transposon-free *B.t.* var. *kurstaki* strain EG7566, a plasmid-free derivative of *B.t.* var. *kurstaki* strain HD73-26 described in U.S. Pat. No. 5,080,897 issued to González, Jr. et al. on Jan. 14, 1992, and also into the Tn5401-containing *B.t.* strain EG2158. Transformed *B.t.* colonies were selected separately for tetracycline resistance ($Tet^R$) and for chloramphenicol resistance ($Cm^R$) and results are shown in the following table:

| Host B.t. Strain | $Cm^R$ Colonies | $Tet^R$ Colonies |
|---|---|---|
| EG7566 | >1000 | >1000 |
| EG2158 | >1000 | 0 |

Both transformed *B.t.* strains exhibited chloramphenicol resistance, apparently due to the presence of the cat gene in the introduced plasmid p83. For the transposon-free *B.t.* strain EG7566 transformants, the existence of tetracycline resistance indicated that plasmid p83 was likely present as an intact plasmid, i.e., no site-specific recombination event had occurred. Restriction enzyme analysis of recombinant plasmids isolated from representative *B.t.* strain EG7566 transformants indicated that the structural integrity of plasmid p83 had been maintained.

The Tn5401-containing *B.t.* strain EG2158 transformants, on the other hand, exhibited no tetracycline resistance, indicating the likely loss of the tet selectable marker gene from site-specific recombination between the two IRS regions in p83. Restriction enzyme analysis of recombinant plasmids recovered from representative chloramphenicol-resistant *B.t.* strain EG2158 transformants confirmed that recombination had occurred between the two IRS regions, resulting in excision of the tet gene from this location in plasmid p83.

EXAMPLE 5

Construction of Recombinant *B.t.* Strains via Site-Specific Recombination Event Using Plasmid Shuttle Vector PEG928.9

Figure 3:
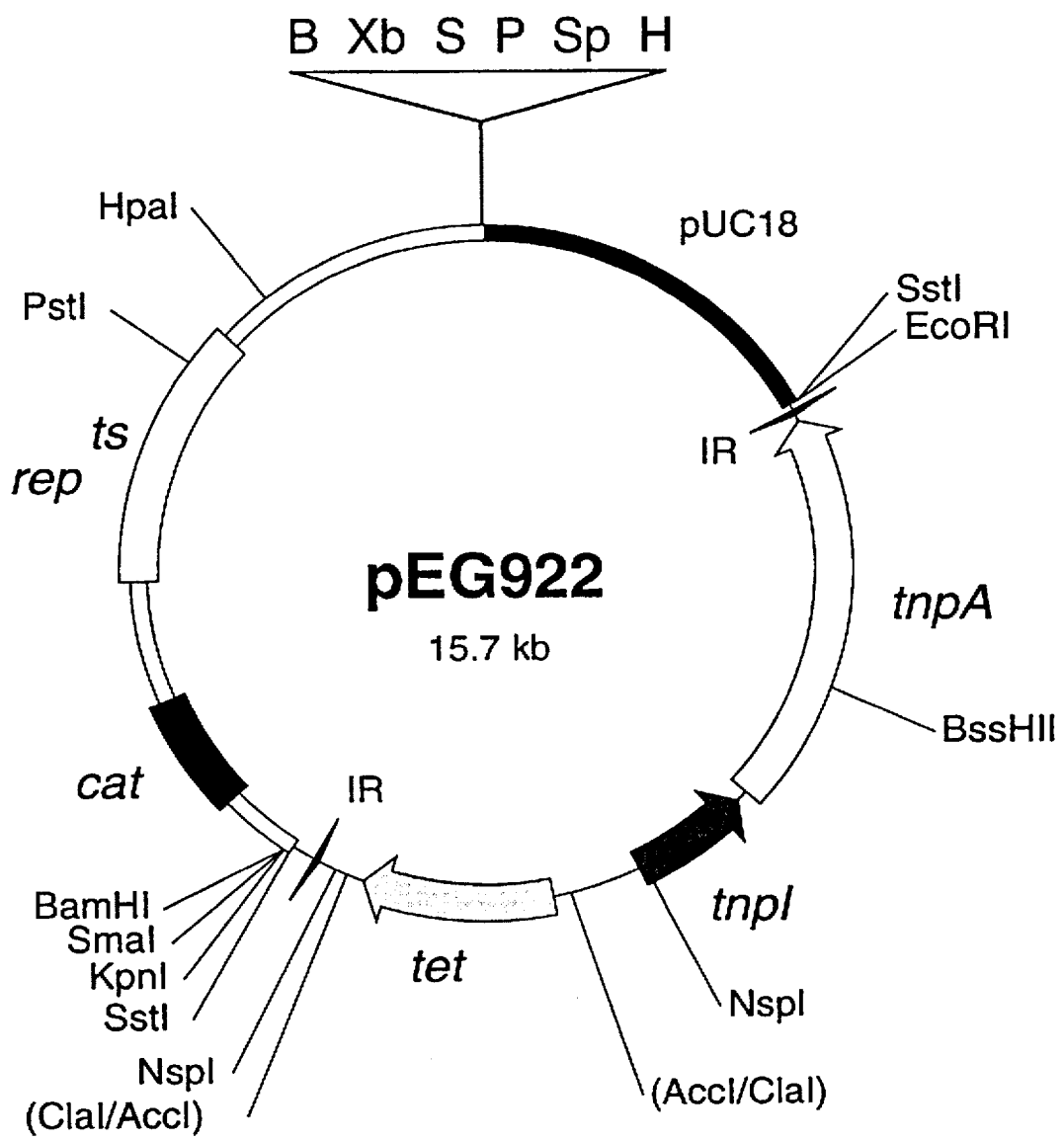
FIG. 3 is a circular structural map of the recombinant plasmid pEG922, a 15.7 kilobase (kb) plasmid which contains the transposon Tn5401 of this invention. Transposon Tn5401 is contained on a ~7 kb SstI-SstI fragment which comprises the following elements shown in FIG. 3: Tn5401 terminal inverted repeats, IR (short dark arrow heads, Tn5401 resolvase gene, tnpI (dark shaded arrow), and Tn5401 transposase gene, tnpA (open arrow). Tn5401 also contains an introduced tetracycline resistance gene, tet (light shaded arrow), a "tag" that serves as a selectable marker for the transposon. Plasmid pEG922 was constructed by inserting the ~7 kb SstI fragment containing Tn5401 into the unique SstI site of plasmid shuttle vector pEG491 (see FIG. 8B). The components of shuttle vector pEG491 include: the thin solid black segment indicating the *E. coli* replicon pUC18, the thick open segment indicating the temperature-sensitive replicon, rep$^{ts}$, from plasmid pE194ts which is functional in gram-positive bacteria but which cannot operate at temperatures at or above 37° C., and the thick black segment indicating the chloramphenicol acetyl transferase gene, cat. At the top of the circular structural map of pEG922 is a multiple cloning site. Abbreviations for the restriction endonuclease cleavage sites in the multiple cloning site of FIG. 3 are as follows: B=BamHI, Xb=XbaI, S=SalI, P-PstI, Sp=SphI, H=HindIII.
Figure 4:
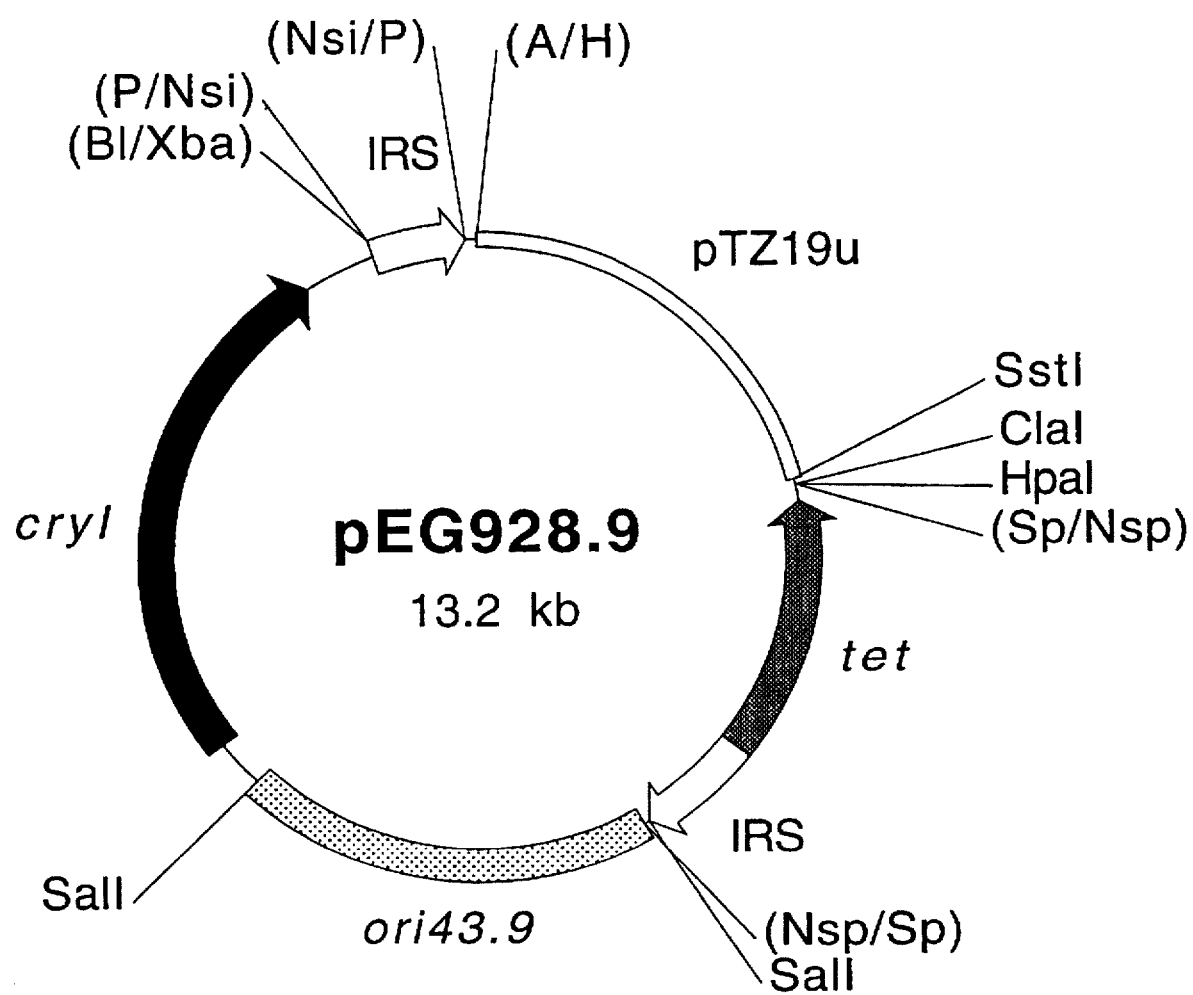
FIG. 4 is a circular structural map of the recombinant plasmid shuttle vector pEG928.9 of this invention, which is 13.2 kb in size. The shuttle vector contains identical internal resolution sites, IRS, in the same orientation (open arrows), and these two sites flank the *E. coli* replicon pTZ19u (open segment in FIG. 4) and a tetracycline resistance gene, tet, from plasmid pBC16 (dark shaded arrow). The plasmid shuttle vector also contains, outside of the IRS sites flanking the DNA not native to *B.t.*, the ori43.9 *B.t.* plasmid origin of replication (light shaded segment) and a lepidopteran-toxin cryIC-cryIAc fusion gene (solid arrow). Letter abbreviations for the restriction endonuclease cleavage sites shown in FIG. 4 are as follows: A=Asp718, Bl=BlnI, ClaI=ClaI, H=HindIII, HpaI=HpaI, Nsi=NsiI, Nsp=NspI, P=PstI, SalI= SalI, Sp=SphI, SstI=SstI, Xba=XbaI.

Example 5 illustrates a method of constructing insecticidal recombinant *B.t.* strains containing no DNA foreign to *B.t.*, utilizing the plasmid shuttle vector pEG928.9 and the Tn5401 transposon-containing recombinant plasmid pEG922 to effect a site-specific recombination event that produces the desired *B.t.* strain construct. The schematic steps of this method are shown in FIG. 5, and detailed circular structural maps of plasmid pEG928.9 and plasmid 922 are shown in FIGS. 4 and 3, respectively, and explained in the Brief Description of the Drawings for these two Figures.

Plasmid shuttle vector pEG928.9, containing a cryI-type gene (a cryIC-cryIAc fusion gene), a *B.t.* origin of replication region (ori43.9, a high copy number mutant of ori43, derived from a 43-MDa *B.t.* toxin plasmid), and two identical internal resolution site (IRS) regions oriented in the same direction, was used to transform a *B.t.* host strain that served as the basis for the recombinant *B.t.* construct. As is discussed in Example 3, plasmid pEG928.9 also contains DNA not native to *B.t.* that is useful in the construction (particularly, development and characterization) of recombinant *B.t.* strains. This foreign DNA consists of an *E. coli* replicon pTZ19u and a tetracycline resistance gene, tet, useful as a selectable marker. The DNA not native to *B.t.* is desirably absent from the insecticidal recombinant *B.t.* construct produced by this method and for this reason is flanked by the duplicate IRS regions. The site-specific recombination event that occurs between the two IRS regions effects excision of the foreign DNA from the plasmid, and this was accomplished in this Example 5 as follows:

*B.t.* var. *kurstaki* strain EG10324 served as the host strain in this Example. *B.t.* strain EG10324 is a phage resistant mutant of *B.t.* var. *kurstaki* strain EG2348, described in U.S. Pat. No. 5,080,897 issued to González, Jr. et al. on Jan. 14, 1992. This transconjugant *B.t.* strain exhibits insecticidal activity against lepidopteran insects. The addition of a recombinant toxin plasmid via the method of this Example was intended to broaden the insecticidal spectrum of the host strain. The cryIc-type *B.t.* toxin gene carried by plasmid shuttle vector pEG928.9 produces a toxin protein with good activity against Spodoptera species.

*B.t.* strain EG10324 was transformed with plasmid shuttle vector pEG928.9 using conventional electroporation techniques, e.g., similar to those described in Example 6 of WO 91/18102. *B.t.* strain EG10324 transformants that were selected for tetracycline resistance were analyzed via restriction enzyme digests, and this analysis confirmed the structural integrity of plasmid pEG928.9 in these $tet^R$ colonies.

These *B.t.* strain EG10324 transformants were next transformed with the Tn5401 transposon-containing plasmid pEG922, selecting this time for chloramphenicol resistance. Plasmid pEG922, described in Example 2 and shown in FIG. 3, contains the Tn5401 transposon of this invention, tagged with a tetracycline antibiotic resistance gene, tet. As noted previously in description of the construction of this plasmid in Example 2, plasmid pEG922 contains a thermosensitive replicon, $rep^{ts}$, that is functional in gram-positive bacteria but that only operates at temperatures below 37° C., in contrast to most *B.t.* replicons which operate at higher temperatures. This transposon-containing plasmid also contains another selectable marker gene, cat, for chloramphenicol resistance.

*B.t.* strain EG10324 double transformants, i.e., containing both plasmid shuttle vector pE928.9 and the Tn5401-containing plasmid pE922, were selected for colonies exhibiting chloramphenicol resistance. In the double recombinant derivative of *B.t.* strain EG10324, plasmid pEG928.9 underwent the site-specific recombination event between its IRS regions, and this event was catalyzed by the introduction of recombinase/resolvase protein produced by expression of the tnpI gene in the Tn5401-containing plasmid pEG922. Production of the recombinase protein was ensured by culturing the double recombinant *B.t.* strain colonies overnight at a temperature of about 30° C., at which the temperature-sensitive replicon in plasmid pEG922 operates.

The site-specific recombination event for plasmid pEG928.9 is schematically shown in FIG. 5, and this resulted in the formation of plasmid pEG928.9Δ. Plasmid pEG928.9Δ is an 8.0 kb recombinant plasmid that contains the ori43.9 origin of replication functional in *B.t.*, the cryIC-cryIAc *B.t.* protein toxin fusion gene, and a single copy of the internal resolution site, derived from the site-specific recombination event.

After the site-specific recombination had been effected, removal of plasmid pEG922 from the double recombinant *B.t.* strain EG10324 transformants also containing plasmid pEG928.9Δ was accomplished by culturing these *B.t.* colonies overnight at a temperature of 37° C. a growth procedure effective to cure temperature-sensitive plasmid pEG922 from the resulting *B.t.* colonies.

The desired insecticidal recombinant *B.t.* construct, containing only a single recombinant plasmid, pEG928.9Δ, was recovered and was designated as *B.t.* strain EG7674.

*B.t.* strain EG7674 lacks the selectable marker genes utilized during its construction and is therefore chloramphenicol-and tetracycline-sensitive. *B.t.* strain EG7674 also lacks the *E. coli* replicon that was originally present in plasmid pEG928.9 but that was subsequently excised during the site-specific recombination event.

Plasmid assay studies of *B.t.* strain EG10324 and its recombinant derivatives described in this Example confirmed the absence of plasmid pEG922 from *B.t.* strain EG7674. Hybridization with the ori43.9 plasmid origin of replication in a Southern blot study of the plasmid assay gel established the presence of pEG928.9Δ as the only recombinant plasmid harbored by *B.t.* strain EG7674.

*B.t.* strain EG7674, containing no DNA not native to *B.t.*, is insecticidal to a wide spectrum of lepidopteran insects and, because of the additional cryIC-cryIAc fusion gene on its recombinant plasmid pEG928.9Δ, is designed to exhibit improved insecticidal activity against *Spodoptera exigua* (beet armyworm) and *Spodoptera littoralis* (Egyptian leaf roller), as compared with the host *B.t.* strain EG10324.

In a similar manner, nine other insecticidal recombinant *B.t.* constructs were prepared via the site-specific recombination method described above. These *B.t.* constructs were similar to *B.t.* strain EG7674 in that their respective recombinant plasmids contained insecticidal *B.t.* protein toxin genes but no DNA not native to *B.t.*

Figure 10:
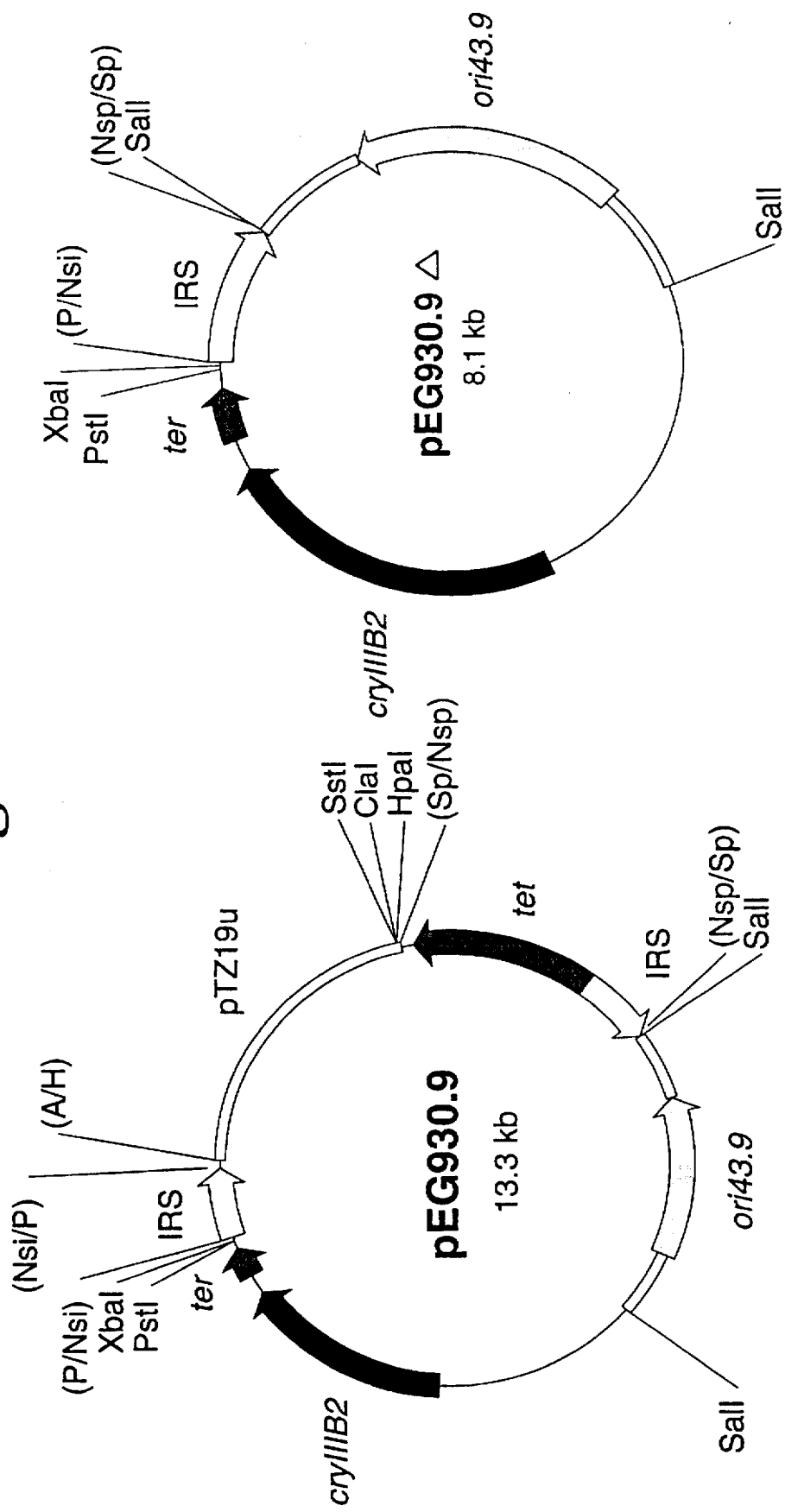
FIG. 10 shows circular structural maps of the recombinant plasmid shuttle vector pEG930.9 of this invention, which is 13.3 kb in size and of its derivative plasmid from a site-specific recombination event, plasmid pEG930.9Δ which is 8.1 kb in size. The plasmid shuttle vector pEG930.9 is similar to plasmid shuttle vector pEG928.9 shown in FIG. 4 except that the cryI-type gene of plasmid pEG928.9 has been replaced with a coleopteran toxin cryIIIB2 gene (solid long arrow) and a cryI transcription terminator, ter (short dark shaded arrow). Other symbols and abbreviations for both plasmid pEG930.9 and plasmid pEG930.9Δ are as described for FIG. 4.

The first construct was a coleopteran-toxic *B.t.* construct which used, as the host strain, transconjugant *B.t.* var. *kurstaki* strain EG2424 (described in U.S. Pat. No. 5,024,837 issued to Donovan et al. on Jun. 18, 1991) and plasmid shuttle vector pEG930.9 whose circular structural map is shown in FIG. 10. Plasmid shuttle vector pEG930.9 is similar to plasmid pEG928.9 except that, in lieu of the cryI-type gene of pEG928.9, it contains the coleopteran toxin cryIIIB2 gene (described in U.S. Pat. No. 5,187,091 issued to Donovan et al. on Feb. 16, 1993) and it contains a transcription terminator downstream of the cryIIIB2 gene. The resulting recombinant *B.t.* construct contained plasmid pEG930.9Δ, whose circular structural map is also shown in FIG. 10, and was designated B.t. strain EG7673. The presence of the cryIIIB2 gene in this recombinant *B.t.* construct, complementing the cryIIIA coleopteran toxin gene present on an 88 mDa plasmid of host *B.t.* strain EG2424, is designed to provide a wider spectrum of insecticidal activity against coleopteran insects, as compared with host *B.t.* strain EG2424.

Figure 11:
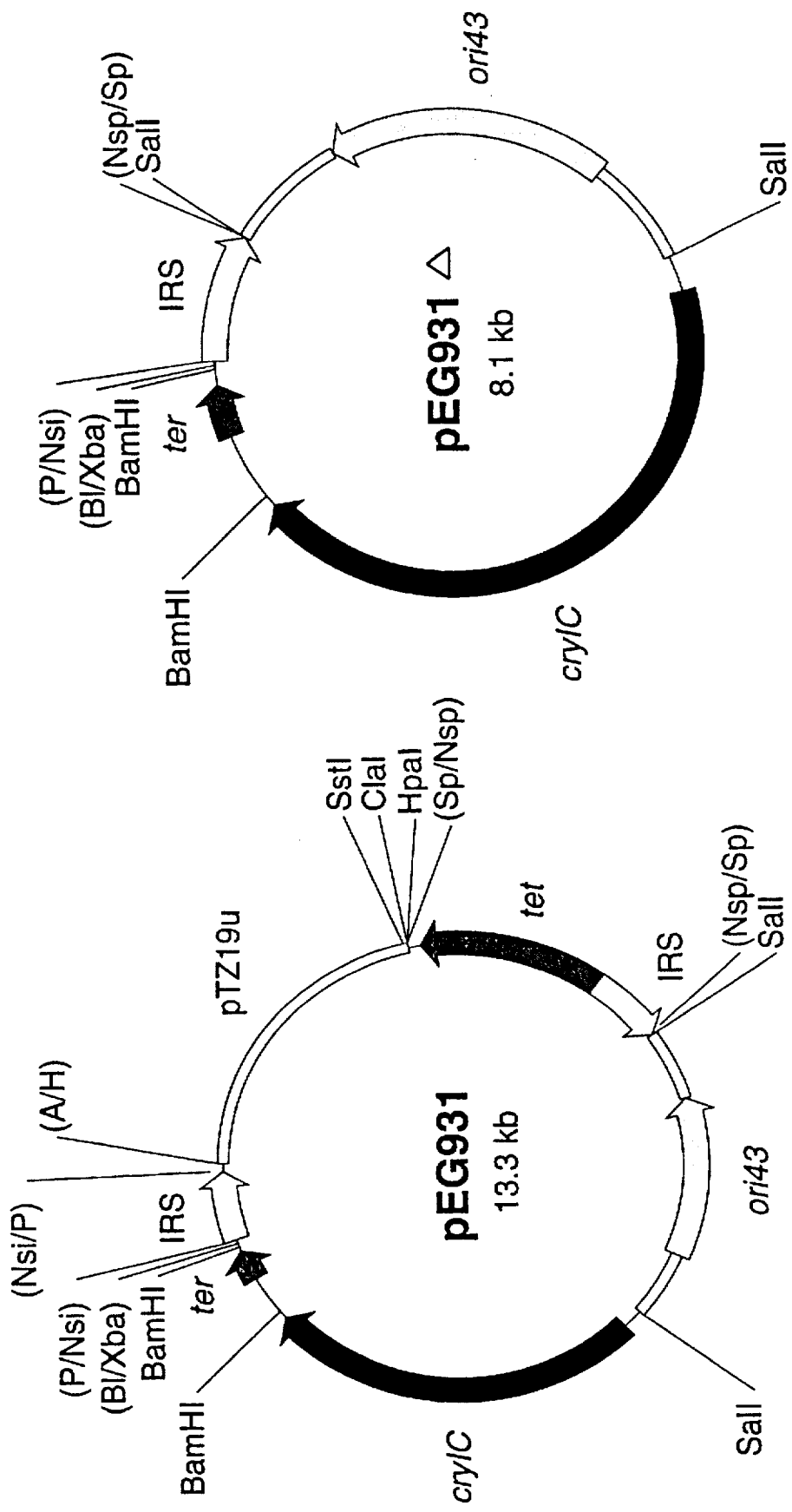
FIG. 11 shows circular structural maps of the recombinant plasmid shuttle vector pEG931 of this invention, which is 13.3 kb in size and of its derivative plasmid from a site-specific recombination event, plasmid pEG931Δ which is 8.1 kb in size. The plasmid shuttle vector pEG931 is similar to plasmid shuttle vector pEG928.9 shown in FIG. 4 except that the cryI-type gene of plasmid pEG928.9 has been replaced with a lepidopteran toxin cryIc gene (solid long arrow) and a cryI transcription terminator, ter (short dark shaded arrow). In addition, the *B.t.* plasmid origin of replication ori43.9 has been replaced with ori43. Other symbols and abbreviations for both plasmid pEG931 and plasmid pEG931Δ are as described for FIG. 4.

The second *B.t.* construct was a lepidopteran-toxic *B.t.* construct which used a novel *B.t.* strain, designated EG4923, as the host strain and plasmid shuttle vector pEG931 whose circular structural map is shown in FIG. 11. Plasmid shuttle vector pEG931 is similar to plasmid pEG928.9 except that (i) a cryIC gene replaces the cryIC-cryIAc fusion gene of pEG928.9, (ii) it contains a transcription terminator downstream of the cryIC gene, and (iii) the *B.t.* origin of replication is ori43 rather than the high copy number mutant ori43.9 used in pEG928.9. The resulting recombinant *B.t.* construct contained plasmid pEG931Δ, whose circular structural map is also shown in FIG. 11, and was designated *B.t.* strain EG7681. The presence of the cryIC gene in this recombinant *B.t.* construct, complementing the cryIAc genes of host *B.t.* strain EG4923, is designed to provide a wider spectrum of insecticidal activity against lepidopteran insects, as compared with host *B.t.* strain EG4923.

Figure 12:
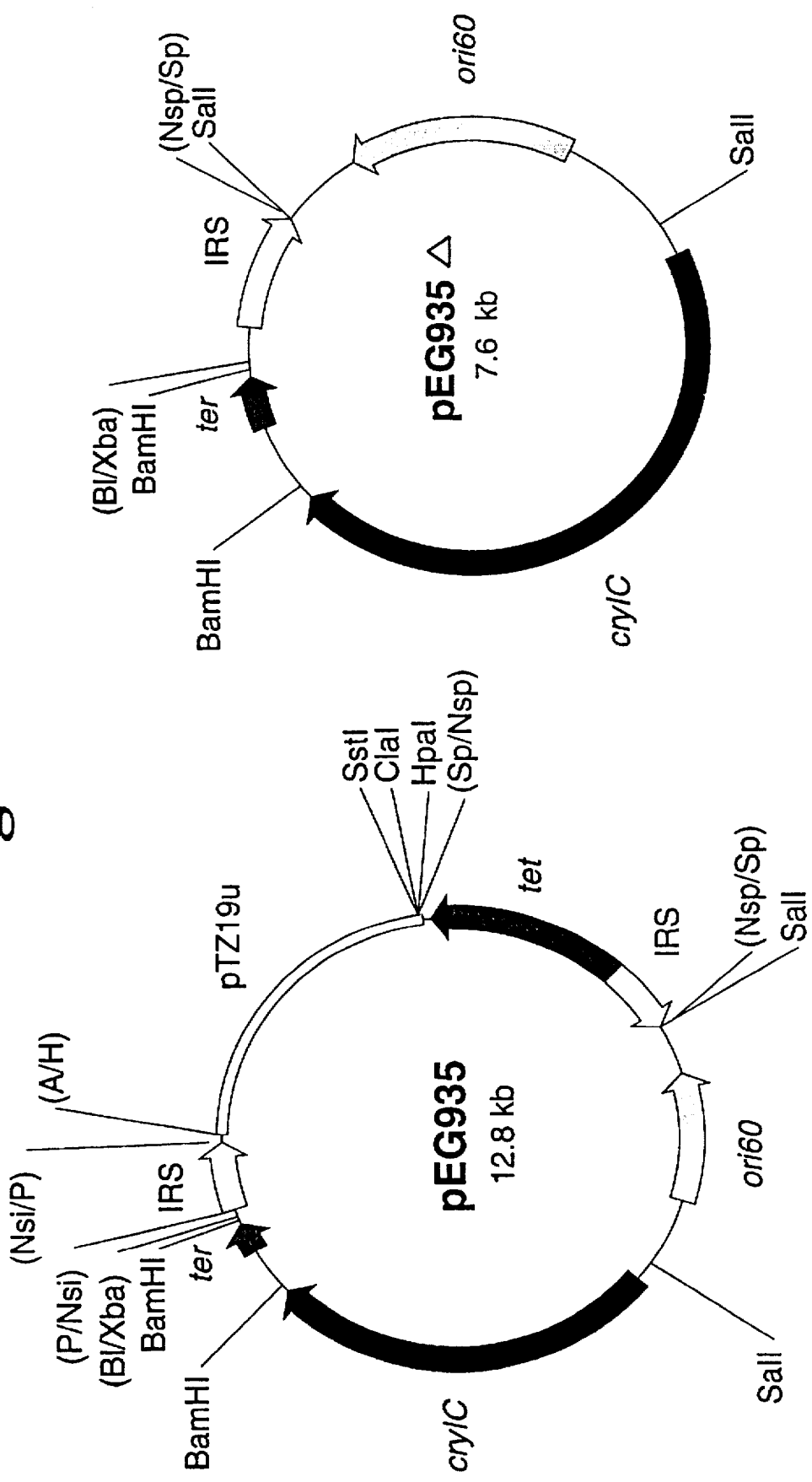
FIG. 12 shows circular structural maps of the recombinant plasmid shuttle vector pEG935 of this invention, which is 12.8 kb in size and of its derivative plasmid from a site-specific recombination event, plasmid pEG935Δ which is 7.6 kb in size. The plasmid shuttle vector pEG935 is similar to plasmid shuttle vector pEG931 shown in FIG. 11 except that the *B.t.* plasmid origin of replication ori43 has been replaced with ori60 (light shaded arrow). Other symbols and abbreviations for both plasmid pEG935 and plasmid pEG935Δ are as described for FIGS. 4 and 11.

The third *B.t.* construct was a lepidopteran-toxic *B.t.* construct which used a novel *B.t.* strain, designated EG4923, as the host strain and plasmid shuttle vector pEG935 whose circular structural map is shown in FIG. 12. Plasmid shuttle vector pEG935 is similar to plasmid pEG931 (shown in FIG. 11) except that the *B.t.* plasmid origin of replication is ori60 rather than ori43 used in pEG931. The resulting recombinant *B.t.* construct contained plasmid pEG935Δ, whose circular structural map is also shown in FIG. 12, and was designated *B.t.* strain EG7841. The presence of the cryIC gene in this recombinant *B.t.* construct, complementing the cryIAc genes of host *B.t.* strain EG4923, is designed to provide a wider spectrum of insecticidal activity against lepidopteran insects, as compared with host *B.t.* strain EG4923.

Figure 13:
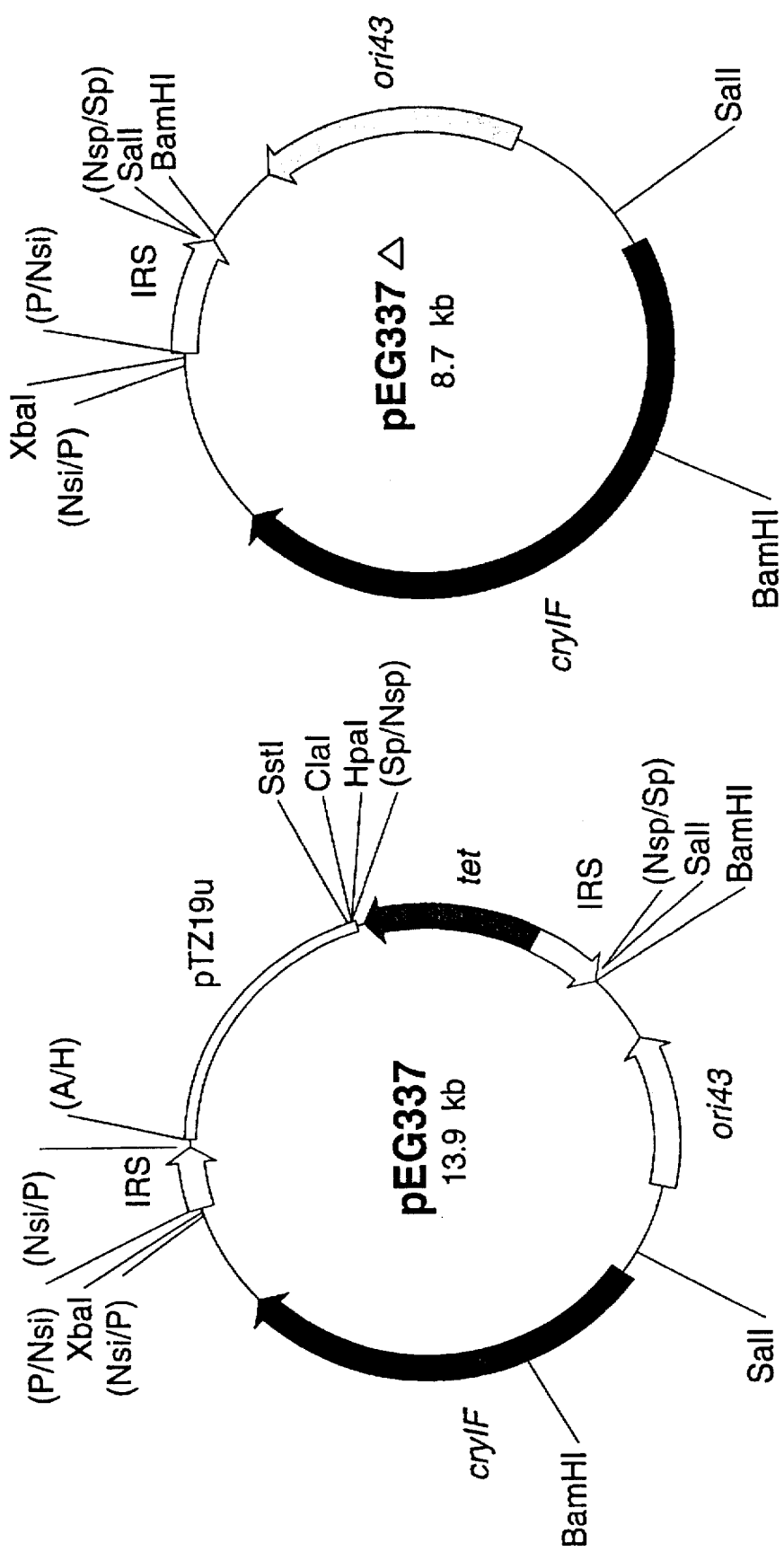
FIG. 13 shows circular structural maps of the recombinant plasmid shuttle vector pEG337 of this invention, which is 13.9 kb in size and of its derivative plasmid from a site-specific recombination event, plasmid pEG337Δ which is 8.7 kb in size. The plasmid shuttle vector pEG337 is similar to plasmid shuttle vector pEG931 shown in FIG. 11 except that the cryIC gene and its accompanying transcription terminator (ter) of plasmid pEG931 have been replaced with a lepidopteran toxin cryIF gene (solid long arrow). Other symbols and abbreviations for both plasmid pEG337 and plasmid pEG337Δ are as described for FIGS. 4 and 11.

The fourth *B.t.* construct was a lepidopteran-toxic *B.t.* construct which used *B.t.* strain EG10324 as the host strain and plasmid shuttle vector pEG337 whose circular structural map is shown in FIG. 13. Host *B.t.* strain EG10324 is a phage-resistant derivative of *B.t.* strain EG2348, described in U.S. Pat. No. 5,080,897 issued to González, Jr. et al. on Jan. 14, 1992. Plasmid shuttle vector pEG337 is similar to plasmid pEG931 (shown in FIG. 11) except that a DNA fragment with a lepidopteran toxin cryIF gene (described in U.S. Pat. No. 5,188,960 issued to Payne et al. on Feb. 23, 1993 and in PCT International Patent Publication No. WO 91/16434 of Ecogen Inc. dated Oct. 31, 1991) replaces the cryIC gene and accompanying transcription terminator of pEG931. The resulting recombinant *B.t.* construct contained plasmid pEG337Δ, whose circular structural map is also shown in FIG. 13, and was designated *B.t.* strain EG7826. The presence of the cryIF gene in this recombinant *B.t.* construct, complementing the cryIA-type genes of host *B.t.* strain EG10324, is designed to provide a wider spectrum of insecticidal activity against lepidopteran insects, as compared with host *B.t.* strain EG10324.

Figure 14:
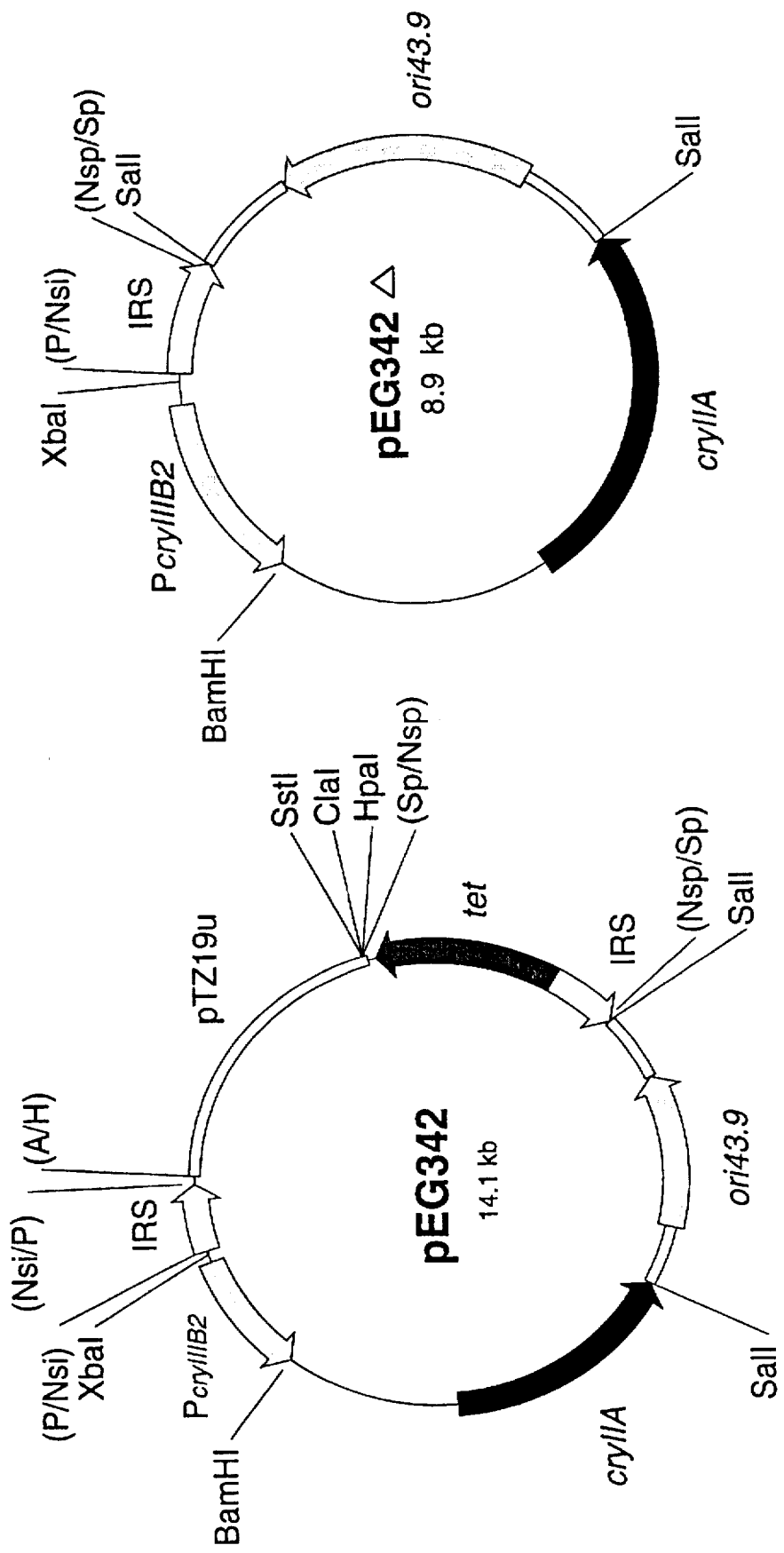
FIG. 14 shows circular structural maps of the recombinant plasmid shuttle vector pEG342 of this invention, which is 14.1 kb in size and of its derivative plasmid from a site-specific recombination event, plasmid pEG342Δ which is 8.9 kb in size. The plasmid shuttle vector pEG342 is similar to plasmid shuttle vector pEG930.9 shown in FIG. 10 except that a cryIIA gene (solid long arrow) replaces the cryIIIB2 gene and accompanying transcription terminator of pEG930.9. P_cryIIIB2 is the cryIIIB2 promoter region. Other symbols and abbreviations for both plasmid pEG342 and plasmid pEG342Δ are as described for FIGS. 4 and 10.

The fifth *B.t.* construct was a lepidopteran-toxic *B.t.* construct which used *B.t.* strain EG7584 as the host strain and plasmid shuttle vector pEG342 whose circular structural map is shown in FIG. 14. Host *B.t.* strain EG7584 is a plasmid-cured derivative of *B.t.* strain HD-263 that is crystal negative, i.e., it contains no toxin plasmids. Plasmid shuttle vector pEG342 is similar to plasmid pEG930.9 (shown in FIG. 10) except that a DNA fragment with a cryIIA gene (described in U.S. Pat. No. 5,196,342 issued to Donovan on Mar. 23, 1993) replaces the cryIIIB2 gene and accompanying transcription terminator of pEG930.9. The resulting recombinant *B.t.* construct contained plasmid pEG342Δ, whose circular structural map is also shown in FIG. 14, and was designated *B.t.* strain EG7856. The presence of the cryIIA gene in this recombinant *B.t.* construct is designed to provide a high level of production of lepidopteran-toxic CryIIA protein during fermentation of this *B.t.* strain.

The sixth *B.t.* construct was a lepidopteran-toxic *B.t.* construct which used a novel *B.t.* strain containing native cryIAc genes, designated EG4923-4, as the host strain and plasmid shuttle vector pEG935 whose circular structural map is shown in FIG. 12. This sixth *B.t.* construct was very similar to *B.t.* strain EG7841, described above as the third construct, except that a different *B.t.* host strain, EG4923-4, was used for this sixth construct. *B.t.* strain EG4923-4 is a spontaneous variant of *B.t.* strain EG4923 in which a large cryptic plasmid has been deleted that is otherwise present in EG4923; this results in higher levels of protein production in derivative *B.t.* strain EG4923-4 from its native cryIAc genes. Plasmid shuttle vector pEG935 is discussed above in connection with *B.t.* strain EG7841. The resulting recombinant *B.t.* construct contained plasmid pEG935Δ, whose circular structural map is also shown in FIG. 12, and was designated *B.t.* strain EG11621. The presence of the cryIc gene in this recombinant *B.t.* construct, complementing the crylAc genes of host *B.t.* strain EG4923-4, is designed to provide a wider spectrum of insecticidal activity against lepidopteran insects, as compared with host *B.t.* strain EG4923-4.

Figure 15:
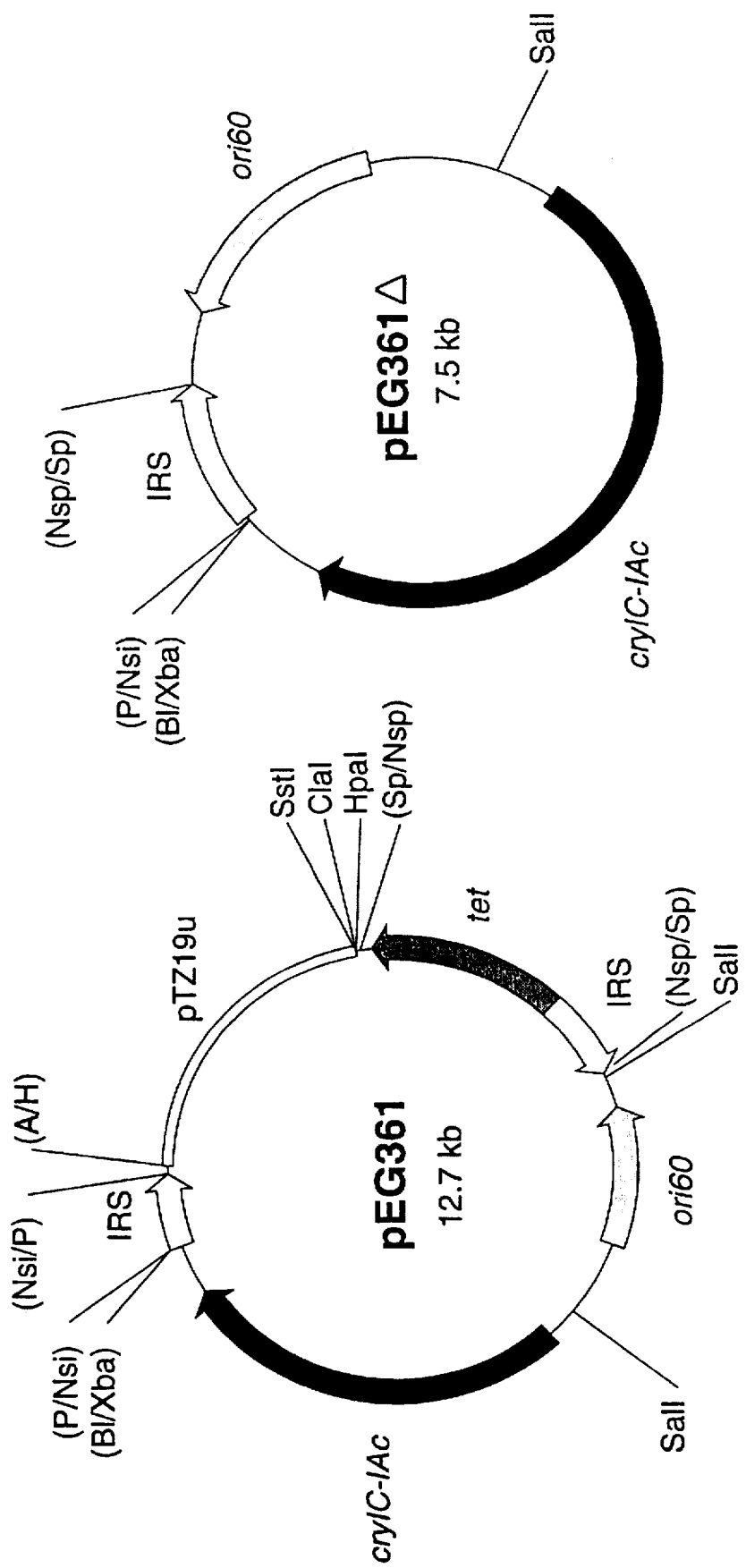
FIG. 15 shows circular structural maps of the recombinant plasmid shuttle vector pEG361 of this invention which is 12.7 kb in size and of its derivative plasmid pEG361Δ which is 7.5 kb in size. The plasmid shuttle vector pEG361 is similar to plasmid shuttle vector pEG928.9 shown in FIG. 4 except that the B.t. plasmid replication origin ori43.9 has been replaced with ori60 (light shaded arrow). Other symbols and abbreviations for both plasmid pEG361 and plasmid pEG361Δ are as described for FIG. 4.

The seventh *B.t.* construct was a lepidopteran-toxic *B.t.* construct which used the novel *B.t.* strain EG4923-4, described above for the sixth *B.t.* construct, as the host strain and plasmid shuttle vector pEG361 whose circular structural map is shown in FIG. 15. Plasmid shuttle vector pEG361 is similar to plasmid shuttle vector pEG928.9 (shown in FIG. 4) except that the *B.t.* plasmid replication origin ori43.9 has been replaced with ori60. The cryIC-crylAc ("cryIC-IAc") fusion gene of pEG361 is the same as that of pEG928.9. The resulting recombinant *B.t.* construct contained plasmid pEG361Δ, whose circular structural map is also shown in FIG. 15, and was designated *B.t.* strain EG11622. The chimeric gene cryIC-crylAc of plasmid pEG361 encodes a fusion protein containing amino acids 1–733 from CryIC and amino acids 727–1178 from CrylAc. The presence of the cryIC-IAc fusion gene in this recombinant *B.t.* construct, complementing the crylAc genes of host *B.t.* strain EG4923-4, is designed to provide a wider spectrum of insecticidal activity against lepidopteran insects, as compared with host *B.t.* strain EG4923-4.

Figure 16:
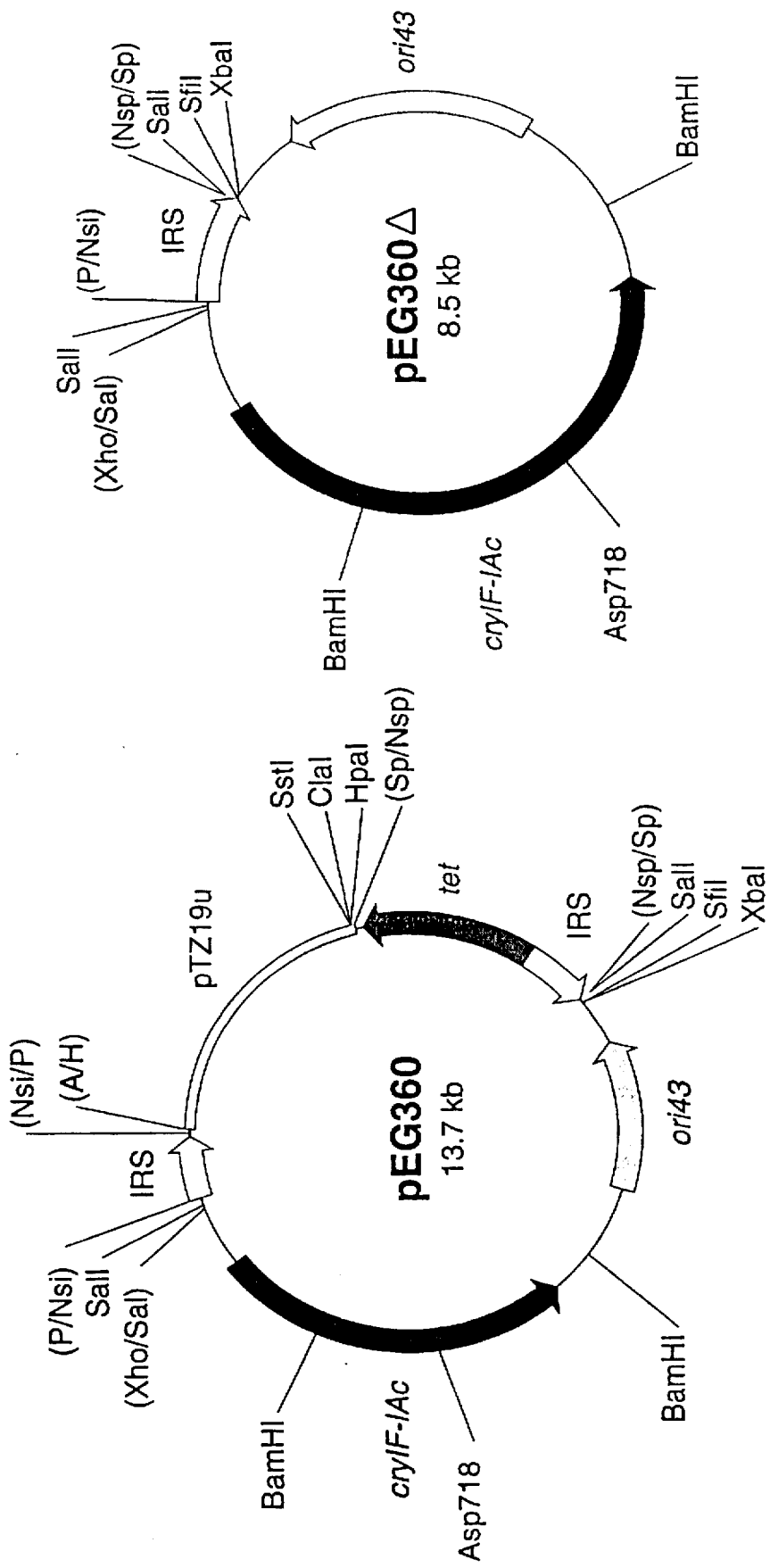
FIG. 16 shows circular structural maps of the recombinant plasmid shuttle vector pEG360 of this invention which is 13.7 kb in size and of its derivative plasmid pEG360Δ which is 8.5 kb in size. The plasmid shuttle vector pEG360 is similar to plasmid shuttle vector pEG337 shown in FIG. 13 except that the cryIF-type gene of plasmid pEG337 has been replaced with a lepidopteran toxin cryIF-cryIAc fusion gene in the opposite orientation. Other symbols and abbreviations for both plasmid pEG360 and plasmid pEG360Δ are as described for FIG. 4 and FIG. 13. Additional abbreviations shown in FIG. 16 for other restriction endonuclease cleavage sites are as follows: SfiI=SfiI, XbaI=XbaI.

The eighth *B.t.* construct was a lepidopteran-toxic *B.t.* construct which used *B.t.* strain EG10324, described above in connection with *B.t.* strain EG7674, as the host strain and plasmid shuttle vector pEG360 whose circular structural map is shown in FIG. 16. Plasmid shuttle vector pEG360 is similar to plasmid shuttle vector pEG337 shown in FIG. 13 except that the cryIF-type gene of plasmid pEG337 has been replaced with a lepidopteran toxin cryIF-crylAc ("cryIF- IAc") fusion gene. The chimeric gene cryIF-IAc encodes a fusion protein containing amino acids 1–718 from CryIF and amino acids 727–1178 from CrylAc. The resulting recombinant *B.t.* construct contained plasmid pEG360Δ, whose circular structural may is also shown in FIG. 16, and was designated *B.t.* strain EG11724. The presence of the cryIF-IAc fusion gene in this recombinant *B.t.* construct, complementing the crylA-type genes of host *B.t.* strain EG10324, is designed to provide a wider spectrum of insecticidal activity against lepidopteran insects, as compared with host *B.t.* strain EG10324.

Figure 17:
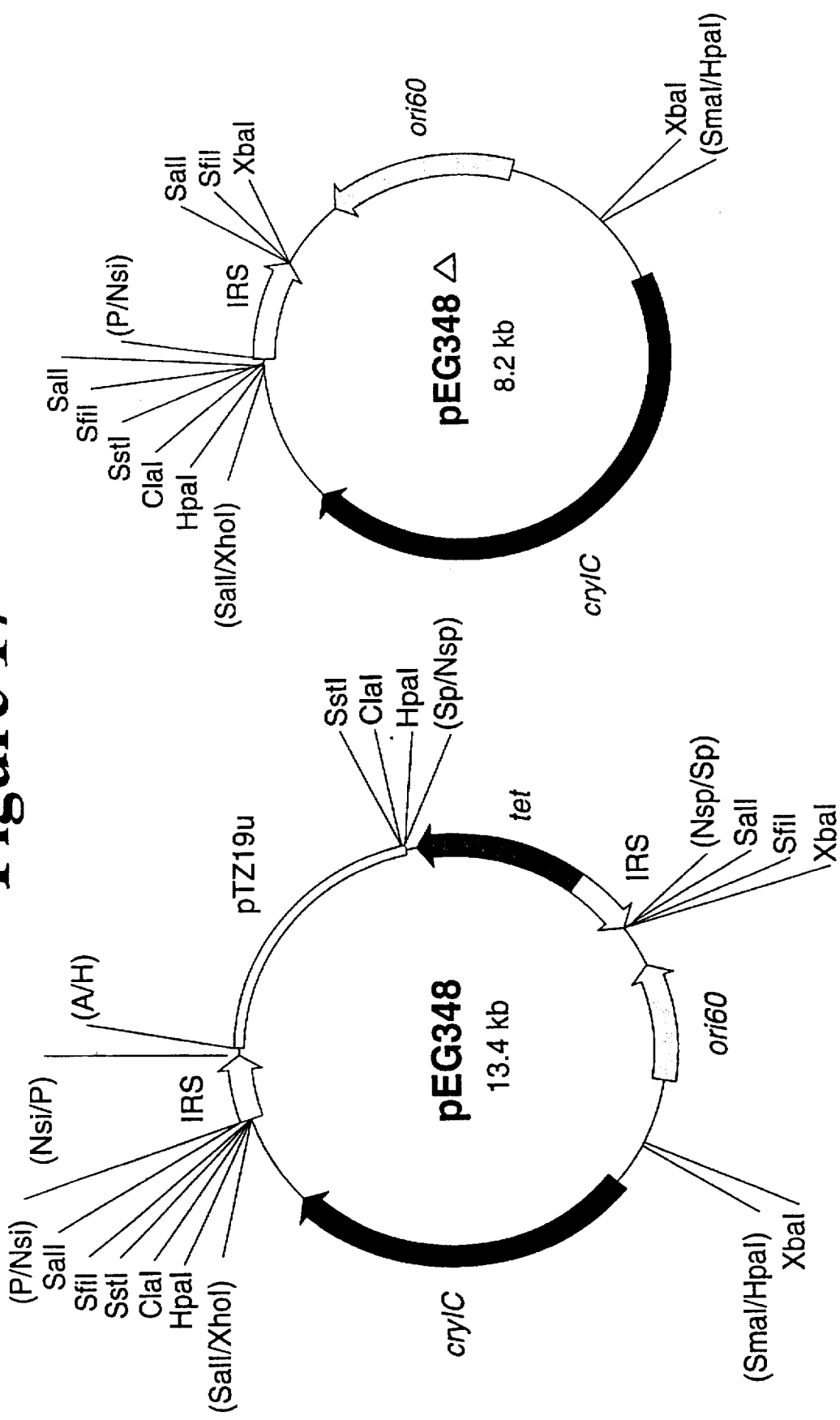
FIG. 17 shows circular restriction maps of the recombinant plasmid shuttle vector pEG348 of this invention which is ~13.4 kb in size and of its derivative plasmid pEG348Δ which is ~8.2 kb in size. The plasmid shuttle vector pEG348 is nearly identical to the plasmid shuttle vector pEG935 shown in FIG. 12 with the exception that the cryIF transcription terminator fragment has been removed and a different cryIC gene was used on plasmid pEG348. Other symbols and abbreviations for both plasmid pEG348 and pEG348Δ are as described for FIG. 4, FIG. 12, and FIG. 16.

The ninth *B.t.* construct was a lepidopteran-toxic *B.t.* construct which used the novel *B.t.* strain EG4923-4, described above for the sixth construct, as the host strain and plasmid shuttle vector pEG348 whose circular structural map is shown in FIG. 17. As described above, plasmid shuttle vector pEG348 is similar to plasmid pEG935 (shown in FIG. 12) except that a different cryIC gene was used and the cryIF transcription terminator region was removed. The cryIC gene used in plasmid pEG348 was identical to the cryIC of *B.t. aizawai* 7-29, described in European Patent Application Publication No. 0 295 156 and in the PCT International Patent Publication No. WO 88/09812, both of Institut Pasteur et al. The resulting recombinant *B.t.* construct contained plasmid pEG348Δ, whose circular structural map is also shown in FIG. 17, and was designated *B.t.* strain EG7841-1. The presence of the cryIC gene in this recombinant *B.t.* construct, complementing the crylAc genes of host *B.t.* strain EG4923-4, is designed to provide a wider spectrum of insecticidal activity against lepidopteran insects, as compared with host *B.t.* strain EG4923-4.

What is claimed is:

1. A recombinant *Bacillus thuringiensis* bacterium designated as *B.t.* strain EG7841, deposited with the NRRL and having Accession No. NRRL B-21250.

2. A recombinant *Bacillus thuringiensis* bacterium designated as *B.t.* strain EG7826, deposited with the NRRL and having Accession No. NRRL B-21249.

3. A recombinant *Bacillus thuringiensis* bacterium designated as *B.t.* strain EG7856, deposited with the NRRL and having Accession No. NRRL B-21251.

4. A recombinant *Bacillus thuringiensis* bacterium designated as *B.t.* strain EG11621, deposited with the NRRL and having Accession No. NRRL B-21506.

5. A recombinant *Bacillus thuringiensis* bacterium designated as *B.t.* strain EG11622, deposited with the NRRL and having Accession No. NRRL B-21507.

6. A recombinant *Bacillus thuringiensis* bacterium designated as *B.t.* strain EG11724, deposited with the NRRL and having Accession No. NRRL B-21508.

7. A recombinant *Bacillus thuringiensis* bacterium designated as *B.t.* strain EG7841-1, deposited with the NRRL and having Accession No. NRRL B-21578.

8. An insecticidal composition comprising the *Bacillus thuringiensis* bacterium of claim 1 and an agriculturally acceptable adjuvant.

9. An insecticidal composition comprising the *Bacillus thuringiensis* bacterium of claim 2 and an agriculturally acceptable adjuvant.

10. An insecticidal composition comprising the *Bacillus thuringiensis* bacterium of claim 3 and an agriculturally acceptable adjuvant.

11. An insecticidal composition comprising the *Bacillus thuringiensis* bacterium of claim 4 and an agriculturally acceptable adjuvant.

12. An insecticidal composition comprising the *Bacillus thuringiensis* bacterium of claim 5 and an agriculturally acceptable adjuvant.

13. An insecticidal composition comprising the *Bacillus thuringiensis* bacterium of claim 6 and an agriculturally acceptable adjuvant.

14. An insecticidal composition comprising the *Bacillus thuringiensis* bacterium of claim 7 and an agriculturally acceptable adjuvant.

15. A method of controlling insect pests comprising applying to a host plant for such insect pests an insecticidally effective amount of the insecticide of claim 8.

16. A method of controlling insect pests comprising applying to a host plant for such insect pests an insecticidally effective amount of the insecticide of claim 9.

17. A method of controlling insect pests comprising applying to a host plant for such insect pests an insecticidally effective amount of the insecticide of claim 10.

18. A method of controlling insect pests comprising applying to a host plant for such insect pests an insecticidally effective amount of the insecticide of claim 11.

19. A method of controlling insect pests comprising applying to a host plant for such insect pests an insecticidally effective amount of the insecticide of claim 12.

20. A method of controlling insect pests comprising applying to a host plant for such insect pests an insecticidally effective amount of the insecticide of claim 13.

21. A method of controlling insect pests comprising applying to a host plant for such insect pests an insecticidally effective amount of the insecticide of claim 14.

* * * * *